United States Patent
Bonnet et al.

(10) Patent No.: US 9,814,661 B2
(45) Date of Patent: Nov. 14, 2017

(54) FRAGRANCE COMPOSITIONS

(71) Applicant: The Procter & Gamble Company, Cincinnati, OH (US)

(72) Inventors: Christelle Marie Sandrine Bonnet, Caillouet-Orgeville (FR); Lynette Anne Makins Holland, Abbots Langley (GB); Fabienne Pastor, Meriel (FR); Jose Maria Velazquez Mendoza, Ascot (GB); Jonathan Richard Stonehouse, Windlesham (GB); William Eoghan Staite, Englefield Green (GB); David Thomas Stanton, Hamilton, OH (US); Oreste Todini, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/567,192

(22) Filed: Dec. 11, 2014

(65) Prior Publication Data

US 2015/0164764 A1    Jun. 18, 2015

Related U.S. Application Data

(60) Provisional application No. 61/915,514, filed on Dec. 13, 2013, provisional application No. 62/009,923, filed on Jun. 10, 2014.

(51) Int. Cl.
| | |
|---|---|
| *A61K 8/60* | (2006.01) |
| *C11B 9/00* | (2006.01) |
| *A61K 8/34* | (2006.01) |
| *A61K 8/37* | (2006.01) |
| *A61Q 15/00* | (2006.01) |

(Continued)

(52) U.S. Cl.
CPC .............. *A61K 8/602* (2013.01); *A61K 8/342* (2013.01); *A61K 8/37* (2013.01); *A61K 8/608* (2013.01); *A61Q 15/00* (2013.01); *A61Q 19/00* (2013.01); *A61Q 19/10* (2013.01); *C11B 9/00* (2013.01); *A61Q 13/00* (2013.01); *A61Q 19/007* (2013.01)

(58) Field of Classification Search
CPC ...................................................... A61K 8/602
See application file for complete search history.

(56) References Cited

U.S. PATENT DOCUMENTS

| | | |
|---|---|---|
| 4,264,478 A | 4/1981 | Seldner |
| 4,324,703 A | 4/1982 | Seldner |

(Continued)

FOREIGN PATENT DOCUMENTS

| | | |
|---|---|---|
| WO | 2011/154926 A1 | 12/2011 |
| WO | 2013/060691 A2 | 5/2013 |

(Continued)

OTHER PUBLICATIONS

Moshel et al., Perfumer & Flavorist, vol. 7, 1982, pp. 41-47.

(Continued)

*Primary Examiner* — Benjamin Packard

(57) ABSTRACT

A fragrance composition having improved intensity and/or longevity of the fragrance profile, including less than about 30 wt % of low volatile fragrance materials (i.e., base notes) having a vapor pressure less than 0.001 Torr at 25° C., and at least one non-odorous fragrance modulator form from an alkoxylated glucoside.

17 Claims, 9 Drawing Sheets

(51) Int. Cl.
*A61Q 19/10* (2006.01)
*A61Q 13/00* (2006.01)
*A61Q 19/00* (2006.01)

(56) References Cited

U.S. PATENT DOCUMENTS

| | | | | |
|---|---|---|---|---|
| 4,374,052 A | * | 2/1983 | Fujikura | C11B 9/0042 510/105 |
| 5,928,631 A | * | 7/1999 | Lucas | A61K 8/19 422/5 |
| 6,126,930 A | * | 10/2000 | Dubois | A61K 8/046 424/401 |

FOREIGN PATENT DOCUMENTS

| | | |
|---|---|---|
| WO | 2013/064412 A2 | 5/2013 |
| WO | WO 2014/093807 A1 | 6/2014 |

OTHER PUBLICATIONS

U.S. Appl. No. 61/988,912, filed May 6, 2014, Lynette Anne Makins Holland et al.

International Search Report and Written Opinion of the International Searching Authority dated Mar. 20, 2015, PCT/US2014/069654, 11 pages.

\* cited by examiner

FRAGRANCE COMPOSITIONS

FIELD OF THE INVENTION

The present application relates to the field of perfumery. In particular, the compositions can have improved intensity and/or longevity of the fragrance profile.

BACKGROUND OF THE INVENTION

It has been a long tradition that highly skilled perfumers carefully select fragrance materials to blend into a composition with the goal of achieving an overall specific fragrance profile of strength and character. In so doing, they need to bear in mind differences in the individual character and volatility of the fragrance materials that are the components of the full fragrance. Conventional perfuming compositions have fragrance profile characterized by a high amount of the low volatile fragrance materials and lower amounts of the volatile fragrance materials. The low volatile fragrance materials are known as "base notes", while the volatile fragrance materials can be further divided into high volatile fragrance materials, identified as "top or head notes", and medium volatile fragrance materials, identified as "middle or heart notes".

The top notes tend to smell citrusy, green, light, fresh, and comprise typically from about 0.1 wt % to 40 wt % relative to the total weight of the perfume formulation. Top notes tend to evaporate quickly due to their high volatility and are characterized by vapor pressure >0.1 Torr at 25° C. (Calculated using Advanced Chemistry Development (ACD/Labs) Software V11.02 (© 1994-2013 ACD/Labs)). Typically, perfumers use top notes to deliver the initial impression of the composition but do not rely on them to contribute much to its overall fragrance profile over time after application.

Middle or heart notes make up from about 0.1 wt % to about 40 wt % relative to the total weight of the perfume formulation. Generally, they become dominant to the untrained nose from several minutes after application and can last up to a few hours afterwards. Middle notes are associated with floral aromas (e.g., jasmin, rose), fruity, marine or spicy aromas and have an intermediate volatility in the vapor pressure range of 0.001 to 0.1 Torr at 25° C.

Base or bottom notes can exist at >30 wt % relative to the total weight of the perfume formulation. They are characterized as animalic, woody, sweet, amber or musky, not being very volatile and having a vapor pressure <0.001 Torr at 25° C. Typically, they are not perceived as dominant until several hours after the application of the perfume or during "dry-down". Base notes are relied upon to improve the strength of the overall fragrance profile over time and replace the heart notes when these are declining, The consequence of using base notes at high levels is that they impart particular odour characters, such as for example, musky, woody, ambery, warm and sweet, which overpower and dominate the fragrance character over time. Some of these base notes have become such common materials (e.g., hedione, galaxolide, etc.) that many fragrance dry-downs appear repetitive, boring, non-memorable and un-interesting to consumers. However, if base notes are reduced or excluded then the fragrance strength weakens over time and does not last for a sufficient duration.

To date, due to the volatility of the fragrance materials, the possible types of fragrance profiles or characters have been somewhat limited. A common complaint by consumers is that middle notes tend to fade too quickly after application of the composition and that the character of the middle notes are undesirably altered by the presence of large amounts of the base notes during the period known as the "dry-down" phase.

Thus, it is desirable to have a composition which retains a significant portion of its initial fragrance character over time, hence, the floral, fruity or spicy characters of the 'heart notes' are perceived for many hours It is also desirable that the fragrance strength of the composition remains noticeable to the consumer over longer periods of time. It is further desirable to be able to create new to the world fragrance profiles wherein one, or several, well-recognized heart note characters, are maintained over time.

It is therefore a challenge to formulate a composition having improved longevity of the fragrance character, without having the fragrance character substantially altered over time by the presence of the base notes in the composition. One approach for addressing the challenge has been to formulate with higher proportions of perfume raw materials with a low volatility and which are therefore more substantive on the substrate. However, as discussed above, this restricts the type of fragrance profile that can be achieved over time.

Another approach, as disclosed in U.S. Pat. No. 4,264,478 (Amerchol Corp.), has been to use a non-odorous material, such as an alkoxylated methyl glucoside, as a modulator to extend the longevity of the perfume raw materials, which are normally too volatile to last for very long. However, U.S. Pat. No. '478 simply teaches the addition of the modulator to an existing fragrance composition with a traditional construction of high levels of base note materials. As such, the resultant overall effect on the fragrance profile of the composition would be to make the whole fragrance weaker because the impact of the modulator on the more volatile fragrance materials cannot be noticed due to the presence of excessive levels of the base notes in the composition.

Similarly, Moshel, et al., *Perfumer & Flavorist*, Vol. 7, pp. 41-47, 1982, teaches that alkoxylated methyl glucosides function as a "fixative" and bind to individual perfume raw materials for improving the longevity of a particular perfume raw material. Moshel, et al., shows that the fixative's ability to improve the longevity for any particular perfume raw material will depend on its boiling point. However, Moshel, et al., does not disclose or suggest how to formulate with the fixative for a full fragrance composition, which incorporates multiple perfume raw materials, so that the fragrance strength is maintained and the character of the middle notes is perceived as dominant after many hours.

As such the prior art teachings still have limitations, and do not adequately teach how to provide a composition wherein the prolonged fragrance profile has sufficient strength to be noticeable and remains distinctive in character over time. Therefore, there remains a need for a composition that is perceived by the consumer over long duration after application. There is also a need for a composition which exhibits enhanced intensity of the fragrance profile over time, so that the volatile fragrance materials remains significantly consistent from its initial impression to the end. It is desirable that the compositions are relevant to fragrances derived from volatile fragrance materials having a vapor pressure ≥0.001 Torr at 25° C.

SUMMARY OF THE INVENTION

In one example, a composition comprises: (i) a fragrance component present in an amount of about 0.04 wt % to about 30 wt %, relative to the total weight of the composition; and wherein: (a) the fragrance component comprises at least one low volatile fragrance material having a vapor pressure less than 0.001 Torr at 25° C.; and (b) the low volatile fragrance material is present in an amount of from about 0.1 wt % to about 30 wt %, relative to the total weight of the fragrance component; and (ii) at least one alkoxylated glucoside non-odorous fragrance modulator in an amount of about 0.1 wt % to about 20 wt %, relative to the total weight of the composition.

These and other features of the present invention will become apparent to one skilled in the art upon review of the following detailed description and the appended claims.

BRIEF DESCRIPTION OF THE DRAWINGS

While the specification concludes with claims particularly pointing out and distinctly claiming the invention, it is believed that the invention will be better understood from the following description of the accompanying figures wherein:

DETAILED DESCRIPTION OF THE INVENTION

Definitions

Figure 1:
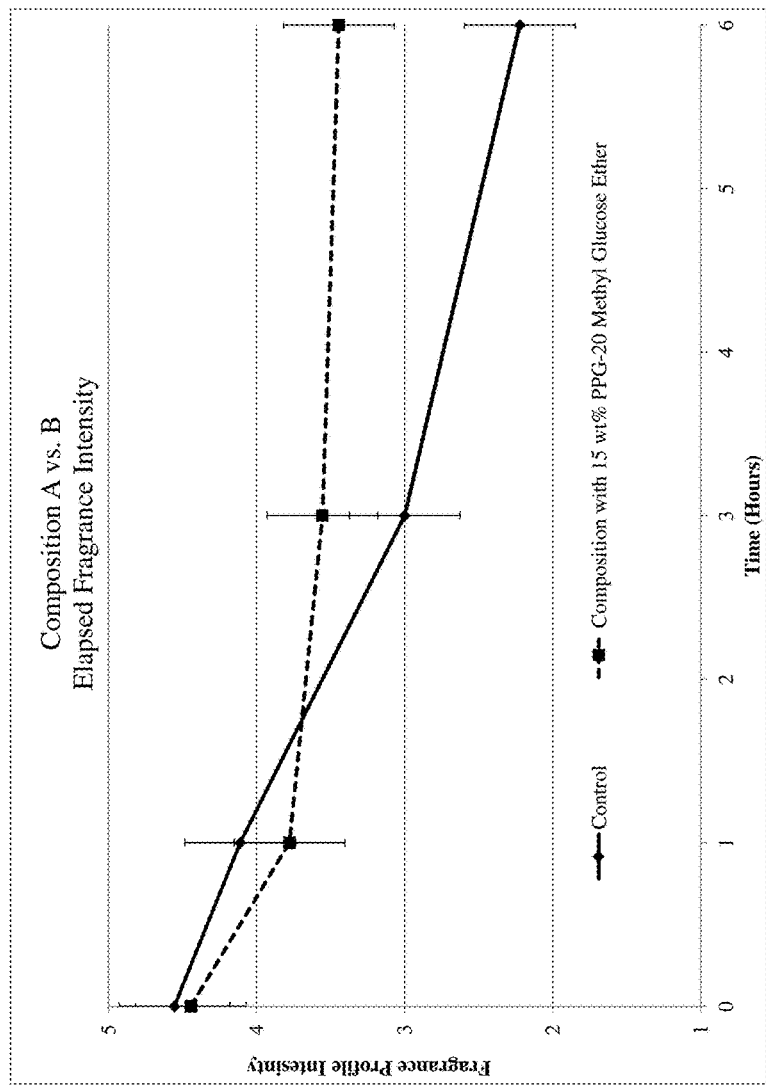
FIG. 1 provides the panel test results of perceived fragrance profile, particularly fragrance intensity, of exemplary "Composition A" comprising 8.00 wt % of low volatile fragrance materials as compared to "Composition B", a control absent of a fragrance modulator (PPG-20 Methyl Glucose Ether), and as a function of time elapsed since application of the composition.

As used herein, articles such as "a" and "an" when used in a claim, are understood to mean one or more of what is claimed or described.

As used herein, the terms "include", "includes" and "including" are meant to be non-limiting.

As used herein, the term "composition" includes a fine fragrance composition intended for application to a body surface, such as for example, skin or hair, i.e., to impart a pleasant odour thereto, or cover a malodour thereof. They are generally in the form of perfume concentrates, perfumes, eau de parfums, eau de toilettes, aftershaves, colognes, body splashes, or body sprays. The fine fragrance compositions may be ethanol based compositions. The term "composition" may also include a cosmetic composition, which comprises a fragrance material for the purposes of delivering a pleasant smell to drive consumer acceptance of the cosmetic composition. The term "composition" may also include cleaning compositions, such as fabric care composition or home care compositions, including air care compositions, for use on clothing or other substrates such as hard surfaces (e.g., dishes, floors, countertops). Additional non-limiting examples of "composition" may also include facial or body powder, foundation, body/facial oil, mousse, creams (e.g., cold creams), waxes, sunscreens and blocks, bath and shower gels, lip balms, self-tanning compositions, masks and patches.

As used herein, the term "consumer" means both the user of the composition and the observer nearby or around the user.

As used herein, the term "fragrance material" and "fragrance materials" relates to a perfume raw material, or a mixture of perfume raw materials, that are used to impart an overall pleasant odour or fragrance profile to a composition. "Fragrance materials" can encompass any suitable perfume raw materials for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also know for use as "fragrance materials". The individual perfume raw materials which comprise a known natural oil can be found by reference to Journals commonly used by those skilled in the art such as "Perfume and Flavourist" or "Journal of Essential Oil Research", or listed in reference texts such as the book by S. Arctander, *Perfume and Flavor Chemicals*, 1969, Montclair, N.J., USA and more recently re-published by Allured Publishing Corporation Illinois (1994). Additionally, some perfume raw materials are supplied by the fragrance houses (Firmenich, International Flavors & Fragrances, Givaudan, Symrise) as mixtures in the form of proprietary specialty accords. Non-limiting examples of the fragrance materials useful herein include pro-fragrances such as acetal pro-fragrances, ketal pro-fragrances, ester pro-fragrances, hydrolyzable inorganic-organic pro-fragrances, and mixtures thereof. The fragrance materials may be released from the pro-fragrances in a number of ways. For example, the fragrance may be released as a result of simple hydrolysis, or by a shift in an equilibrium reaction, or by a pH-change, or by enzymatic release.

As used herein, the term "fragrance profile" means the description of how the fragrance perceived by the human nose evolves over time from when it is first applied. It is a result of the combination of the top, middle and base notes, if present, of a fragrance. A fragrance profile is composed of 2 characteristics: 'intensity' and 'character'. The 'intensity' relates to the perceived strength whilst 'character' refers to the odour impression or quality of the perfume, i.e., fruity, floral, woody, etc.

As used herein, the terms "perfume" and "fragrance" are used interchangeably to designate the component in the composition that is formed of fragrance materials, i.e., ingredients capable of imparting or modifying the odour of skin or hair or other substrate.

As used herein, the terms "modulator" and "fixative" are used interchangeably to designate an agent having the capacity to affect the fragrance profile by impacting the fragrance materials' evaporation rate. By incorporating the modulator, it is desired that the fragrance profile, like the volatile fragrance materials components, of the composition can be perceived by an observer or user thereof, over a longer period of time, as compared to the same perception in the absence of the modulator. In particular, alkoxylated glucoside, like PPG-20 Methyl Glucose Ether (Glucam™ P-20 available from Lubrizol (USA)), is a modulator of the perceived tenacity of the compositions, i.e., it is used to prolong the perceived intensity of the fragrance profile over time, as compared to the perception when PPG-20 Methyl Glucose Ether is not used in the composition. However, simply adding modulators to a traditionally constructed fragrance composition will not ensure an improved or enhanced fragrance profile over time. Instead, when the modulators are added in the presence of reduce levels of low volatile fragrance materials the intensity of the fragrance profile, like the volatile fragrance materials, can be perceived for longer periods as compared to control composition absent the modulators and low levels of low volatile fragrance materials.

As used herein, the term "co-modulator" means an agent that is added to the composition in addition to the modulators and has the similar function of impacting the evaporation rate and intensity of the fragrance materials, so as to improve or prolong the perception of the fragrance profile by the consumer. An example of a co-modulator is isocetyl alcohol (CERAPHYL® ICA; see PCT Publication No. WO2013/64412 (Firmenich)).

As used herein, the term "non-odorous" means an agent that does not impart an odour of its own when added into an exemplary composition. For example, a "non-odorous modulator" such as PPG-20 Methyl Glucose Ether does not impart a new odour that alters the character of the composition to which it is added.

As used herein, the term "vapor pressure" means the partial pressure in air at a defined temperature for a given chemical species. It defines a chemical species' desire to be in the gas phase rather than the liquid or solid state. The higher the vapour pressure the greater the proportion of the material that will, at equilibrium, be found in a closed headspace. It is also related to the rate of evaporation of a fragrance material which is defined in an open environment where material is leaving the system. The vapor pressure is determined according to the reference program Advanced Chemistry Development (ACD/Labs) Software Version 11.02, (© 1994-2013).

It is understood that the test methods that are disclosed in the Test Methods Section of the present application are to be used to determine the respective values of the parameters of as described and claimed herein.

All percentages are by weight of the total composition unless specifically stated otherwise. All ratios are weight ratios, unless specifically stated otherwise, and all measurements are made at 25° C., unless otherwise designated.

Compositions

A composition can comprise a fragrance component present in an amount of from about 0.04 wt % to 30 wt %, relative to the total weight of the composition. The fragrance component may also be less than about 25 wt %, less than about 20 wt %, less than about 15 wt %, less than about 10 wt % or less than about 8 wt %, relative to the total weight of the composition. The fragrance component may be present in an amount of from about 0.04 wt %, 0.3 wt %, 1 wt %, 8 wt % or 10 wt %, to about 15 wt %, 20 wt %, 25 wt % or 30 wt %, relative to the total weight of the composition.

Further, the fragrance component comprises at least one low volatile fragrance material having a vapor pressure <0.001 Torr at 25° C. For example, a composition comprises at least 5 low volatile fragrance materials. A composition comprises low, very low, or even negligible, levels of the low volatile fragrance materials than would traditionally be present in a fragrance composition. As such, compositions can comprise low levels of the volatile fragrance material present in an amount of from about 0.01 wt % to about 30 wt %, less than about 25%, less than about 20 wt %, less than about 12 wt %, less than about 10 wt %, less than about 8 wt %, less than about 5 wt %, less than about 2 wt %, less than about 1 wt %, or combinations thereof, relative to the total weight of the fragrance component. Alternatively, the low volatile fragrance material is present in an amount of from about 0.01 wt %, 1 wt %, 2 wt %, 5 wt %, 8 wt %, 10 wt %, 12 wt %, 15 wt %, 20 wt %, 25 wt % or 30 wt %, relative to the total weight of the fragrance component. If there is more than one low volatile fragrance materials, then the ranges provided hereinabove cover the total of all of the low volatile fragrance materials.

The composition further comprises at least one non-odorous fragrance modulator formed from an alkoxylated glucoside. The non-odorous fragrance modulator can be selected, for example, from the group consisting of methyl glucoside polyol, ethyl glucoside polyol, and propyl glucoside polyol. In one example, the alkoxylated glucoside is PPG-20 Methyl Glucose Ether (GLUCAM™ P-20 available from Lubrizol, USA). The alkoxylated glucoside is present in an amount of from about 0.1 wt % to about 20 wt %, from about 0.5 wt % to about 18 wt %, from about 2.5 wt % to about 15 wt %, or combinations thereof, relative to the total weight of the composition. The alkoxylated glucoside is present in an amount of from about 0.1 wt %, 0.5 wt % or 2.5 wt %, to about 15 wt %, 18 wt % or 20 wt %, relative to the total weight of the composition. If there is more than one non-odorous fragrance modulators, then the ranges provided hereinabove cover the total of all of the non-odorous fragrance modulators.

The non-odorous modulator can be a liquid at temperatures lower than 100° C., even at ambient temperature. In one example, non-odorous modulators are fully miscible with the PRMs to form a single phase liquid. However, if the PRMs are not entirely miscible, or are immiscible, then co-solvents (e.g., dipropylene glycol (DPG), triethyl citrate, or others as well known to those skilled in the art) can be added to aid in the solubility of the PRMs.

It has been surprisingly discovered that by reducing the levels of the low volatile fragrance materials (i.e., base notes) in a composition, the effect of the non-odorous modulator on the fragrance profile, particularly the portion of the fragrance profile which is derived from volatile fragrance materials (i.e., top and middle notes), can be improved. By "improved" it is meant that the fragrance character of the composition, particular the components contributed by the volatile fragrance materials, can be perceived by the consumer at later time points such as, for example, 2 hours, 4 hours, 6 hours, 8 hours, 10 hours, and possibly all the way up to 24 hrs after application as compared to controls, i.e., compositions containing normal or large levels of the low volatile fragrance materials and the non-odorous modulator or compositions containing reduced levels of low volatility fragrance materials and no non-odorous modulator.

Alternatively, by "improved" it can mean that the perception of the components contributed by the volatile fragrance materials, by the consumer, is markedly increased or enhanced as compared to the controls. "Increased" or "enhanced" perception of the fragrance profile means that the consumer perceives the fragrance profile of a composition as not changing from its initial impression or the changes are minimal from when the composition was first applied to when it dissipates.

Typically, it has been very difficult to formulate fragrance profile with an accord, particularly a floral accord characteristic of the middle notes, which can last for very long periods, especially throughout the life of the composition after its application, without giving way to the stronger odours of the base notes. Reducing levels of the low volatile fragrance materials (i.e., base notes) with the modulators will allow perfumers to increase the perception of the volatile perfume materials, particularly the middle notes, to create new characters and address a re-occurring consumer issue that particular fragrance profiles, particularly the floral aromas, do not last long enough.

Such a solution as presented herein provides enhanced longevity of the fragrance profile, particularly amongst those composition formulated from volatile fragrance materials having medium to high vapor pressure ranges (≥0.001 Torr at 25° C.), without having to rely on the presence or significant amounts of the low volatile fragrance materials, which has a tendency to overpower and alter the overall character of a fragrance. This provides the perfumer options to formulate accords having new fragrance profiles.

The fragrance component can further comprise one or more volatile fragrance materials having a vapor pressure ≥0.001 Torr at 25° C. The volatile fragrance material is present in an amount of from about 70 wt % to about 99.9 wt %, greater than about 80 wt %, or greater than 88 wt %, or combinations thereof, relative to the total weight of the fragrance component. In addition, the volatile fragrance material can be present in an amount of from about 70 wt %, 75 wt %, 80 wt %, 85 wt %, 88 wt %, to about 90 wt %, 92 wt %, 95 wt %, 98 wt % or 99.9 wt %, relative to the total weight of the fragrance component. The compositions can comprise at least 5, at least 10, at least 15 or at least 20, volatile fragrance materials. If there is more than one volatile fragrance materials, then the ranges provided hereinabove cover the total weight of all of the volatile fragrance materials.

Volatile fragrance materials can be divided into: (i) a high volatile fragrance material having a vapor pressure >0.1 Torr at 25° C. and (ii) a medium volatile fragrance material having a vapor pressure in the range of from 0.001 Torr at 25° C. to 0.1 Torr at 25° C. While the further classification of the volatile fragrance materials into high and medium volatile fragrance materials is provided to help illustrate the fragrance characters of the perfume raw materials and is useful for when it comes to formulating new fragrance profiles, it should not be construed as limiting on what qualifies as a volatile fragrance material.

The low volatile fragrance material can be selected, for example, from ingredients listed in Table 1 hereinafter.

A composition may further comprise one or more non-odorous fragrance co-modulators selected from the group consisting of:

(i) Isocetyl alcohol (CERAPHYL® ICA);
(ii) PPG-3 myristyl ether (like Tegosoft™ APM and/or Varonic® APM);
(iii) Neopentyl glycol diethylhexanoate (like Schercemol™ NGDO); and
(iv) a mixture thereof;

wherein the fragrance co-modulators are present in an amount of from about 0.05 wt % to about 10 wt %, from about 0.5 wt % to about 6 wt %, from about 0.05 wt % or 0.5 wt % to about 6 wt % or 10 wt %, or combinations thereof, relative to the total weight of the composition. If there is more than one non-odorous fragrance co-modulator, then the ranges provided hereinabove cover all of the non-odorous fragrance co-modulators.

The non-odorous fragrance modulators are formed, for example, of at least 50 wt % of a non-odorous fragrance modulator, relative to the total weight of the non-odorous modulators and the non-odorous co-modulators present in the composition.

A composition may also comprise:
(i) from about 50 wt % to about 80 wt % of ethanol;
(ii) from about 0.1 wt % to about 20 wt % of at least one non-odorous fragrance modulator formed of an alkoxylated glucoside selected from the group consisting of methyl glucoside polyol, ethyl glucoside polyol, and propyl glucoside polyol; and
(iii) a fragrance component;
and wherein wt % of the non-odorous fragrance modulator is greater than the fragrance component.

Entrapment Materials

The composition may also comprise an entrapment material at a level such that the weight ratio of the entrapment material to the fragrance materials is in the range of from about 1:20 to about 20:1. The composition may comprise an entrapment material in the amount of from about 0.001 wt % to about 40 wt %, from about 0.1 wt % to about 25 wt %, from about 0.3 wt % to about 20 wt %, from about 0.5 wt % to about 10 wt %, or from about 0.75 wt % to about 5 wt %, relative to the total weight of the composition.

Suitable entrapment materials for use herein are selected from polymers; capsules, microcapsules and nanocapsules;

liposomes, absorbents; cyclic oligosaccharides and mixtures thereof. Cyclic oligosaccharides can include PCT Publication Nos. WO2000/67721 (Procter & Gamble); and WO2000/67720 (Procter & Gamble); and U.S. Pat. No. 6,893,647 (Procter & Gamble)).

As used herein, the term "cyclic oligosaccharide" means a cyclic structure comprising six or more saccharide units. In one example, cyclic oligosaccharides have six, seven, or eight saccharide units. It is common in the art to abbreviate six, seven and eight membered cyclic oligosaccharides to α, β and γ respectively.

The cyclic oligosaccharide of the compositions may comprise any suitable saccharide or mixtures of saccharides. Examples of suitable saccharides include, but are not limited to, glucose, fructose, mannose, galactose, maltose and mixtures thereof. A cyclic oligosaccharide comprises glucose. The cyclic oligosaccharides for use herein can include α-cyclodextrins or β-cyclodextrins, or mixtures thereof.

The cyclic oligosaccharide, or mixture of cyclic oligosaccharides, for use herein may be substituted by any suitable substituent or mixture of substituents. Herein the use of the term "mixture of substituents" means that two or more different suitable substituents can be substituted onto one cyclic oligosaccharide. The derivatives of cyclodextrins consist mainly of molecules wherein some of the OH groups have been substituted. Suitable substituents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino) propyl ether; quaternary ammonium groups; anionic cyclodextrins such as carboxyalkyl groups, sulphobutylether groups, sulphate groups, and succinylates; amphoteric cyclodextrins; and mixtures thereof.

The substituents may be saturated or unsaturated, straight or branched chain. Substituents can include, for example, saturated and straight chain alkyl groups, hydroxyalkyl groups and mixtures thereof. Alkyl and hydroxyalkyl substituents can be selected from $C_1$-$C_8$ alkyl or hydroxyalkyl groups or mixtures thereof, alkyl and hydroxyalkyl substituents can be selected from $C_1$-$C_6$ alkyl or hydroxyalkyl groups or mixtures thereof, alkyl and hydroxyalkyl substituents can be selected from $C_1$-$C_4$ alkyl or hydroxyalkyl groups, and mixtures thereof. Exemplary alkyl and hydroxyalkyl substituents include propyl, ethyl, methyl, for example hydroxypropyl and methyl.

Exemplary cyclic oligosaccharides are unsubstituted, or are substituted by only saturated straight chain alkyl, or hydroxyalkyl substituents. Therefore, examples of cyclic oligosaccharides for use herein are α-cyclodextrin, β-cyclodextrin, methyl-α-cyclodextrin, methyl-β-cyclodextrin, hydroxypropyl-α-cyclodextrin and hydroxypropyl-β-cyclodextrin. These are available from Wacker-Chemie GmbH Hanns-Seidel-Platz 4, Munchen, DE under the tradename Alpha W6 M and Beta W7 M respectively.

The cyclic oligosaccharides of the compositions can be soluble in water, ethanol, or both water and ethanol. As used herein, "soluble" means at least about 0.1 g of solute dissolves in 100 mL of solvent, at 25° C. and 1 atm of pressure. Cyclic oligosaccharides for use herein can have a solubility of at least about 1 g/100 mL, at 25° C. and 1 atm of pressure. In one example, cyclic oligosaccharides are only present at levels up to their solubility limits in a given composition at room temperature. A person skilled in the art will recognize that the levels of cyclic oligosaccharides will also be dependent on the components of the composition and their levels, for example the solvents used or the exact fragrance oils, or combination of fragrance oils, present in the composition.

The compositions disclosed herein may comprise from 0.001 wt % to 40%, from 0.1 wt % to 25 wt %, from 0.3 wt % to 20 wt %, from 0.5 wt % to 10 wt % or from 0.75 wt % to 5 wt %, relative to the total weight of the composition, of a cyclic oligosaccharide.

Volatile Solvents

Fine fragrance compositions commonly contain high levels of ethanol or other alcohols (e.g., methanol, propanol, isopropanol, butanol, and mixtures thereof) commonly found in commercial fine fragrance products. Accordingly, ethanol may be present in the compositions, and more specifically, it can form from about 10 wt % to about 80 wt %, or even from about 25 wt % to about 75 wt % of the composition, relative to the total weight of the composition. Any acceptable quality of ethanol, compatible and safe for the specific intended use of the composition such as, for example, topical applications of fine fragrance or cosmetic compositions, and is convenient for use in the compositions herein.

Non-Volatile Solvents

The composition may comprise a non-volatile solvent or a mixture of non-volatile solvents. Non-limiting examples of non-volatile solvents include benzyl benzoate, diethyl phthalate, isopropyl myristate, propylene glycol, dipropylene glycol, triethyl citrate, and mixtures thereof. These solvents often are introduced to the product via the perfume oil as many perfume raw materials may be purchased as a dilution in one of these solvents. Where non-volatile solvents are present, introduced either with the perfume materials or separately, then for the purposes of calculating the proportion of fragrance component having a vapour pressure of <0.001 Torr at 25° C. the total fragrance components does not include non-volatile solvents. In addition if present with cyclic oligosaccharides, the non-volatile solvent may be included at a weight ratio of the non-volatile solvent to the cyclic oligosaccharide of less than 1:1, less than 1:2, less than 1:10, or less than 1:100.

Water

Water may be present in the composition, at a level of about 40 wt % or less, about 20 wt % or less, or about 10 wt % or less, relative to the total weight of the composition. Water may be present in an amount of from about 10 wt % or 20 wt %, to about 40 wt %, relative to the total weight of the composition. When the composition is a cosmetic composition the level of water should not be so high that the product becomes cloudy thus negatively impacting the product aesthetics, where clarity is desired. It is understood that the amount of water present in the composition may be from the water present in the ethanol used in the composition, as the case may be.

Propellants

The compositions described herein may include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1diflouroethane). The propellant may have a concentration from about 15%, 25%, 30%, 32%, 34%, 35%, 36%, 38%, 40%, or 42%, to about 70%, 65%, 60%, 54%, 52%, 50%, 48%, 46%, 44%, or 42%, by weight of the total fill of materials stored within a container.

Antiperspirant Active

The compositions described herein may be free of, substantially free of, or may include an antiperspirant active (i.e., any substance, mixture, or other material having antiperspirant activity). Examples of antiperspirant actives include astringent metallic salts, like the inorganic and organic salts of aluminum, zirconium and zinc, as well as mixtures thereof. Such antiperspirant actives include, for example, the aluminum and zirconium salts, such as aluminum halides, aluminum hydroxyhalides, zirconyl oxyhalides, zirconyl hydroxyhalides, and mixtures thereof.

Other Ingredients

In yet another aspect, the composition consists essentially of the recited ingredients but may contain small amounts (not more than about 10 wt %, no more than 5 wt %, or no more than 2 wt % thereof, relative to the total weight of the composition) of other ingredients that do not impact the fragrance profile, particularly the evaporation rate and release of the fragrance materials. For example, a fine fragrance composition may comprise stabilizing or antioxidant agents, UV filters or quenchers, or colouring agents, commonly used in perfumery. There are a number of other examples of additional ingredients that are suitable for inclusion in the present compositions, particularly in compositions for cosmetic use. These include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, and propyl paraben; dyes; pH adjusting agents such as lactic acid, citric acid, sodium citrate, succinic acid, phosphoric acid, sodium hydroxide, and sodium carbonate; deodorants and anti-microbials such as farnesol and zinc phenolsulphonate; humectants such as glycerine; oils; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; silicones; solvents such as hexylene glycol; hair-hold polymers such as those described in PCT Publication WO94/08557 (Procter & Gamble); salts in general, such as potassium acetate and sodium chloride and mixtures thereof.

The composition may be a mixture of fragrance materials possibly together with other ingredients such as, for example, perfume carriers. By the term "perfume carrier", it is meant to include materials which are practically neutral from a perfumery point of view, i.e., which does not significantly alter the organoleptic properties of perfuming components. The perfume carrier may be compatible liquid or solid fillers, diluents, extenders and the like. The term "compatible", as used herein, means that the components of the compositions are capable of being combined with the primary actives, and with each other, in a manner such that there is no interaction which would substantially reduce the efficacy of the composition under ordinary use situations. The type of carrier utilized depends on the type of product desired and may comprise, but are not limited to, solutions, aerosols, emulsions (including oil-in-water or water-in-oil), gels, and liposomes. In one example, the carrier is a liquid and will be a solvent such as, for example, dipropyleneglycol, diethyl phthalate, isopropyl myristate, benzyl benzoate, 2-(2-ethoxyethoxy)-1-ethanol, or ethyl citrate (triethyl citrate).

The compositions may take any form suitable for use, like for perfumery or cosmetic use. These include, but are not limited to, vapour sprays, aerosols, emulsions, lotions, liquids, creams, gels, sticks, ointments, pastes, mousses, powders, granular products, substrates, cosmetics (e.g. semisolid or liquid makeup, including foundations) and the like. In one example, the compositions take the form of a vapour spray. Compositions can be further added as an ingredient to other compositions, like fine fragrance or cosmetic compositions, in which they are compatible. As such they can be used within solid composition or applied to substrates etc.

In one example, a composition comprises:
(i) a fragrance component present in the amount of from about 1.0 wt % to about 30 wt % relative to the total weight of the composition, and wherein the fragrance component comprises:
  (a) at least one low volatile fragrance material having a vapor pressure <0.001 Torr at 25° C., present in the amount of from about 0.1 wt % to about 30 wt %, relative to the total weight of the fragrance component; and
  (b) at least one volatile fragrance material having a vapor pressure ≥0.001 Torr at 25° C., present in the amount of from about 70 wt % to about 99.9 wt %, relative to the total weight of the fragrance component; and
(ii) at least one non-odorous fragrance modulator formed of an alkoxylated glucoside, like PPG-20 Methyl Glucose Ether, in the amount of from about 2.5 wt % to about 20 wt %, relative to the total weight of the composition.

The composition can further comprise one or more non-odorous fragrance co-modulators, for example, selected from the group consisting of isocetyl alcohol (CERAPHYL® ICA), PPG-3 myristyl ether (like Tegosoft™ APM and/or Varonic® APM), neopentyl glycol diethylhexanoate (like Schercemol™ NGDO), and a mixture thereof, present in an amount of from about 0.5 wt % to about 10 wt %, relative to the total weight of the composition.

The compositions described herein can encompass any of the ingredients cited herein, in any embodiment wherein each such ingredient is independently present in any appropriate amount as defined herein. Many such compositions, than what is specifically set out herein, can be encompassed.

Article of Manufacture

The composition may be included in an article of manufacture comprising a spray dispenser. The spray dispenser may comprise a vessel for containing the composition to be dispensed. The spray dispenser may comprise an aerosolized composition (i.e. a composition comprising a propellant) within the vessel as well. Other non-limiting examples of spray dispensers include non-aerosol dispensers (e.g. vapor sprays), manually activated dispensers, pump-spray dispensers, or any other suitable spray dispenser available in the art.

Methods of Using the Compositions

The composition described herein is a useful perfuming composition, which can be advantageously used as consumer products intended to perfume any suitable substrate.

As used herein, the term "substrate" means any surface to which the composition may be applied to without causing any undue adverse effect. For example, this can include a wide range of surfaces including human or animal skin or hair, paper (fragranced paper), air in a room (air freshner or aromatherapy composition), fabric, furnishings, dishes, hard surfaces and related materials. Substrates can include body surfaces such as, for example, hair and skin.

The composition may be used in a conventional manner for fragrancing a substrate. An effective amount of the composition, typically from about 1 µL to about 10,000 µL, from about 10 µL to about 1,000 µL, from about 25 µL to about 500 µL, or from about 50 µL to about 100 µL, is applied to the suitable substrate. For example, an effective amount of the composition can be from about 1 µL, 10 µL, 25 µL or 50 µL, to about 100 µL, 500 µL, 1,000 µL or 10,000 µL. The composition may be applied by hand or applied utilizing a delivery apparatus such as, for example, a vaporizer or atomizer. The composition can be allowed to dry after its application to the substrate. Application could be the result of one or more distinct applications of the composition or the continuous release of a composition via a vaporizer or other type of atomizer.

The composition can be a fine fragrance composition in the form of a perfume, an eau de toilette, an eau de parfum, a cologne, a body splash, or a body spray, for example. Therefore, a method of modifying or enhancing the odour properties of a body surface, like hair or skin, can comprise contacting or treating the body surface with a composition as described herein.

In another example, composition may be used as consumer products or articles selected from the group consisting of a fabric care product, an air care product, or a home care product. Therefore, a method of modifying or enhancing the odour properties of a substrate, like fabric, furnishings, dishes, hard surfaces and related materials, can comprise contacting or treating the substrate with a composition as described herein.

Another method can include a method of enhancing the fragrance profile of a composition, by improving, for example, the longevity of an aroma of the composition. The method comprises bringing into contact or mixing at least one non-odorous fragrance modulator with at least one low volatile fragrance material. The aroma can be derived from the volatile fragrance materials in the composition and characterized by a floral aroma. Non-limiting examples of floral aroma include lavender-type note, a rose-type note, a lily of the valley-type note, a muguet-type note, a jasmine-type note, a *magnolia*-type note, a cyclamen-type note, a hyacinth-type note, a lilac-type note, an orange blossom-type note, a cherry blossom-type note, a peony-type note, a lotus-type note, a linden blossom-type note, an osmanthus-type note, a lilac-type note, a heliotrope-type note, a violet-type note, an orris-type note, a tiare-type note and the like.

The fragrance profile or aroma of the composition can be detectable by a consumer at later time points such as, for example, 2 hours, 4 hours, 6 hours, 8 hours, 10 hours, and possibly all the way up to 24 hours after application of the composition to a substrate as compared to controls.

Fragrance Materials

The "fragrance materials" have been classified by their vapour pressure, as determined according to the reference program Advanced Chemistry Development (ACD/Labs) Software Version 11.02, (1994-2013). For the purpose of clarity, when the fragrance materials refer to a single individual compound, its vapor pressure should be determined according to the reference program cited above. In the case that the fragrance materials are a natural oil, extract or absolute, which comprises a mixture of several compounds, the vapor pressure of the complete oil should be treated as a mixture of the individual perfume raw material components using the reference program cited above. The individual components and their level, in any given natural oil or extract, can be determined by direct injection of the oil into a GC-MS column for analysis as known by one skilled in the art. In the scenario that the fragrance materials are a proprietary specialty accord, so called 'bases', the vapor pressure, using the reference program cited above, should preferably be obtained from the supplier. However, it is understood by one skilled in the art that they can physically analyze the composition of a full fragrance oil available commercially to identity the fragrance raw materials and their levels using standard GC-MS techniques. This would be irrespective of whether they had been added to the fragrance oil as individual chemicals, as components of naturals or from proprietary bases. Although proprietary bases and and naturals are included in our examples, when analyzing a commercially available fragrance via GC-MS one could simply identify the components of the base or natural oil as part of the overall fragrance mixture and their levels, without being able to identify which proprietary base or natural oil the fragrance had come from.

The nature and type of fragrance materials in the compositions can be selected by the skilled person, on the basis of its general knowledge together with the teachings contained herein, with reference to the intended use or application of the composition and the desired fragrance profile effect. Examples of suitable fragrance materials are disclosed in U.S. Pat. Nos. 4,145,184, 4,209,417, 4,515,705, and 4,152,272, provided that the composition comprises low volatile fragrance materials at levels in an amount of from about 0.1 wt % to about 30 wt %, relative to the total weight of the fragrance component.

Examples of fragrance materials having a vapor pressure <0.001 Torr at 25° C. (according to the reference program Advanced Chemistry Development (ACD/Labs) Software Version 11.02, (© 1994-2013)) to form the at most about 30 wt % of the low volatile fragrance materials are listed in Table 1 hereinafter.

TABLE 1

Low Volatile Fragrance Materials for Use in the Compositions

| CAS Number | Chemical name | Common Name** | Vapor Pressure (Torr at 25° C.)* |
|---|---|---|---|
| 1211-29-6 | Cyclopentaneacetic acid, 3-oxo-2-(2Z)-2-penten-1-yl-, methyl ester, (1R,2R)- | Methyl jasmonate | 0.00096500 |
| 28219-60-5 | 2-Buten-1-ol, 2-methyl-4-(2,2,3-trimethyl-3-cyclopenten-1-yl)- | Hindinol | 0.00096100 |

TABLE 1-continued

Low Volatile Fragrance Materials for Use in the Compositions

| CAS Number | Chemical name | Common Name** | Vapor Pressure (Torr at 25° C.)* |
|---|---|---|---|
| 93-08-3 | Ethanone, 1-(2-naphthalenyl)- | Methyl beta-naphthyl ketone | 0.00095700 |
| 67633-95-8 | 3-Decanone, 1-hydroxy- | Methyl Lavender Ketone | 0.00095100 |
| 198404-98-7 | Cyclopropanemethanol, 1-methyl-2-[(1,2,2-trimethylbicyclo[3.1.0]hex-3-yl)methyl]- | Javanol ® | 0.00090200 |
| 121-32-4 | Benzaldehyde, 3-ethoxy-4-hydroxy- | Ethyl vanillin | 0.00088400 |
| 28940-11-6 | 2H-1,5-Benzodioxepin-3(4H)-one, 7-methyl- | Oxalone ® | 0.00083100 |
| 139504-68-0 | 2-Butanol, 1-[[2-(1,1-dimethylethyl)cyclohexyl]oxy]- | Amber core | 0.00080300 |
| 502847-01-0 | Spiro[5.5]undec-8-en-1-one, 2,2,7,9-tetramethyl- | Spiro[5.5]undec-8-en-1-one, 2,2,7,9-tetramethyl- | 0.00073100 |
| 2570-03-8 | Cyclopentaneacetic acid, 3-oxo-2-pentyl-, methyl ester, (1R,2R)-rel- | trans-Hedione | 0.00071000 |
| 24851-98-7 | Cyclopentaneacetic acid, 3-oxo-2-pentyl-, methyl ester | Methyl dihydrojasmonate | 0.00071000 |
| 101-86-0 | Octanal, 2-(phenylmethylene)- | Hexyl cinnamic aldehyde | 0.00069700 |
| 37172-53-5 | Cyclopentanecarboxylic acid, 2-hexyl-3-oxo-, methyl ester | Dihydro Iso Jasmonate | 0.00067500 |
| 65113-99-7 | 3-Cyclopentene-1-butanol, α,β,2,2,3-pentamethyl- | Sandalore ® | 0.00062500 |
| 68133-79-9 | Cyclopentanone, 2-(3,7-dimethyl-2,6-octadien-1-yl)- | Apritone | 0.00062000 |
| 7212-44-4 | 1,6,10-Dodecatrien-3-ol, 3,7,11-trimethyl- | Nerolidol | 0.00061600 |
| 53243-59-7 | 2-Pentenenitrile, 3-methyl-5-phenyl-, (2Z)- | Citronitril | 0.00061500 |
| 134123-93-6 | Benzenepropanenitrile, 4-ethyl-α,α-dimethyl- | Fleuranil | 0.00057600 |
| 77-53-2 | 1H-3a,7-Methanoazulen-6-ol, octahydro-3,6,8,8-tetramethyl-, (3R,3aS,6R,7R,8aS)- | Cedrol Crude | 0.00056900 |
| 54464-57-2 | Ethanone, 1-(1,2,3,4,5,6,7,8-octahydro-2,3,8,8-tetramethyl-2-naphthalenyl)- | Iso-E Super ® | 0.00053800 |
| 20665-85-4 | Propanoic acid, 2-methyl-, 4-formyl-2-methoxyphenyl ester | Vanillin isobutyrate | 0.00051200 |
| 79-78-7 | 1,6-Heptadien-3-one, 1-(2,6,6-trimethyl-2-cyclohexen-1-yl)- | Hexalon | 0.00049800 |
| 6259-76-3 | Benzoic acid, 2-hydroxy-, hexyl ester | Hexyl Salicylate | 0.00049100 |
| 93-99-2 | Benzoic acid, phenyl ester | Phenyl Benzoate | 0.00047900 |
| 153859-23-5 | Cyclohexanepropanol, 2,2,6-trimethyl-α-propyl-, (1R,6S)- | Norlimbanol | 0.00046900 |
| 70788-30-6 | Cyclohexanepropanol, 2,2,6-trimethyl-α-propyl- | Timberol | 0.00046900 |
| 68555-58-8 | Benzoic acid, 2-hydroxy-, 3-methyl-2-buten-1-yl ester | Prenyl Salicylate | 0.00045700 |
| 950919-28-5 | 2H-1,5-Benzodioxepin-3(4H)-one, 7-(1-methylethyl)- | Cascalone | 0.00045500 |
| 30168-23-1 | Butanal, 4-(octahydro-4,7-methano-5H-inden-5-ylidene)- | Dupical | 0.00044100 |
| 1222-05-5 | Cyclopenta[g]-2-benzopyran, 1,3,4,6,7,8-hexahydro-4,6,6,7,8,8-hexamethyl- | Galaxolide | 0.00041400 |
| 1222-05-5 | Cyclopentanone, 2-[2-(4-methyl-3-cyclohexen-1-yl)propyl]- | Nectaryl | 0.00036700 |
| 4674-50-4 | 2(3H)-Naphthalenone, 4,4a,5,6,7,8-hexahydro-4,4a-dimethyl-6-(1-methylethenyl)-, (4R,4aS,6R)- | Nootkatone | 0.00035800 |
| 3487-99-8 | 2-Propenoic acid, 3-phenyl-, pentyl ester | Amyl Cinnamate | 0.00035200 |
| 118-71-8 | 4H-Pyran-4-one, 3-hydroxy-2-methyl- | Maltol | 0.00033700 |

TABLE 1-continued

Low Volatile Fragrance Materials for Use in the Compositions

| CAS Number | Chemical name | Common Name** | Vapor Pressure (Torr at 25° C.)* |
|---|---|---|---|
| 128119-70-0 | 1-Propanol, 2-methyl-3-[(1,7,7-trimethylbicyclo[2.2.1]hept-2-yl)oxy]- | Bornafix | 0.00033400 |
| 103614-86-4 | 1-Naphthalenol, 1,2,3,4,4a,5,8,8a-octahydro-2,2,6,8-tetramethyl- | Octalynol | 0.00033200 |
| 7785-33-3 | 2-Butenoic acid, 2-methyl-, (2E)-3,7-dimethyl-2,6-octadien-1-yl ester, (2E)- | Geranyl Tiglate | 0.00033200 |
| 117933-89-8 | 1,3-Dioxane, 2-(2,4-dimethyl-3-cyclohexen-1-yl)-5-methyl-5-(1-methylpropyl)- | Karanal | 0.00033100 |
| 629-92-5 | Nonadecane | Nonadecane | 0.00032500 |
| 67801-20-1 | 4-Penten-2-ol, 3-methyl-5-(2,2,3-trimethyl-3-cyclopenten-1-yl)- | Ebanol | 0.00028100 |
| 65416-14-0 | Propanoic acid, 2-methyl-, 2-methyl-4-oxo-4H-pyran-3-yl ester | Maltol Isobutyrate | 0.00028000 |
| 28219-61-6 | 2-Buten-1-ol, 2-ethyl-4-(2,2,3-trimethyl-3-cyclopenten-1-yl)- | Laevo Trisandol | 0.00028000 |
| 5986-55-0 | 1,6-Methanonaphthalen-1(2H)-ol, octahydro-4,8a,9,9-tetramethyl-, (1R,4S,4aS,6R,8aS)- | Healingwood | 0.00027800 |
| 195251-91-3 | 2H-1,5-Benzodioxepin-3(4H)-one,7-(1,1-dimethylethyl)- | Transluzone | 0.00026500 |
| 120-51-4 | Benzoic acid, phenylmethyl ester | Benzyl Benzoate | 0.00025400 |
| 3100-36-5 | 8-Cyclohexadecen-1-one | Cyclohexadecenone | 0.00025300 |
| 65405-77-8 | Benzoic acid, 2-hydroxy-, (3Z)-3-hexen-1-yl ester | cis-3-Hexenyl salicylate | 0.00024600 |
| 4940-11-8 | 4H-Pyran-4-one, 2-ethyl-3-hydroxy- | Ethyl Maltol | 0.00022800 |
| 541-91-3 | Cyclopentadecanone, 3-methyl- | Muskone | 0.00017600 |
| 118-58-1 | Benzoic acid, 2-hydroxy-, phenylmethyl ester | Benzyl salicylate | 0.00017500 |
| 81783-01-9 | 6,8-Nonadien-3-one, 2,4,4,7-tetramethyl-, oxime | Labienoxime | 0.00017300 |
| 25485-88-5 | Benzoic acid, 2-hydroxy-, cyclohexyl ester | Cyclohexyl Salicylate | 0.00017300 |
| 91-87-2 | Benzene, [2-(dimethoxymethyl)-1-hepten-1-yl]- | Amyl Cinnamic Aldehyde Dimethyl Acetal | 0.00016300 |
| 104864-90-6 | 3-Cyclopentene-1-butanol, β,2,2,3-tetramethyl-δ-methylene- | Firsantol | 0.00016000 |
| 224031-70-3 | 4-Penten-1-one, 1-spiro[4.5]dec-7-en-7-yl- | Spirogalbanone | 0.00015300 |
| 236391-76-7 | Acetic acid, 2-(1-oxopropoxy)-, 1-(3,3-dimethylcyclohexyl)ethyl ester | Romandolide ® | 0.00012400 |
| 115-71-9 | 2-Penten-1-ol, 5-[(1R,3R,6S)-2,3-dimethyltricyclo[2.2.1.02,6]hept-3-yl]-2-methyl-, (2Z)- | cis-alpha-Santalol | 0.00011800 |
| 107898-54-4 | 4-Penten-2-ol, 3,3-dimethyl-5-(2,2,3-trimethyl-3-cyclopenten-1-yl)- | Polysantol ® | 0.00011700 |
| 107898-54-4 | 5,8-Methano-2H-1-benzopyran-2-one, 6-ethylideneoctahydro- | Florex | 0.00011000 |
| 69486-14-2 | 4-Cyclopentadecen-1-one, (4Z)- | Exaltenone | 0.00009640 |
| 32388-55-9 | Ethanone, 1-[(3R,3aR,7R,8aS)-2,3,4,7,8,8a-hexahydro-3,6,8,8-tetramethyl-1H-3a,7-methanoazulen-5-yl]- | Vertofix ® | 0.00008490 |
| 131812-67-4 | 1,3-Dioxolane, 2,4-dimethyl-2-(5,6,7,8-tetrahydro-5,5,8,8-tetramethyl-2-naphthalenyl)- | Okoumal ® | 0.00007600 |
| 106-02-5 | Oxacyclohexadecan-2-one | Exaltolide ® | 0.00006430 |
| 141773-73-1 | 1-Propanol, 2-[1-(3,3-dimethylcyclohexyl)ethoxy]-2-methyl-, 1-propanoate | Helvetolide ® | 0.00005790 |
| 63314-79-4 | 5-Cyclopentadecen-1-one, 3-methyl- | Delta Muscenone | 0.00005650 |
| 77-42-9 | 2-Penten-1-ol, 2-methyl-5-[(1S,2R,4R)-2-methyl-3-methylenebicyclo[2.2.1]hept-2-yl]-, (2Z)- | cis-beta-Santalol | 0.00004810 |

TABLE 1-continued

Low Volatile Fragrance Materials for Use in the Compositions

| CAS Number | Chemical name | Common Name** | Vapor Pressure (Torr at 25° C.)* |
|---|---|---|---|
| 362467-67-2 | 2H-1,5-Benzodioxepin-3(4H)-one, 7-(3-methylbutyl)- | Azurone | 0.00004770 |
| 28371-99-5 | Ethanone, 1-(2,6,10-trimethyl-2,5,9-cyclododecatrien-1-yl)- | Trimofix O | 0.00004580 |
| 16223-63-5 | 1H-3a,6-Methanoazulene-3-methanol, octahydro-7,7-dimethyl-8-methylene-, (3S,3aR,6R,8aS)- | Khusimol | 0.00004400 |
| 10461-98-0 | Benzeneacetonitrile, α-cyclohexylidene- | Peonile | 0.00004290 |
| 50607-64-2 | Benzoic acid, 2-[(2-methylpentylidene)amino]-, methyl ester | Mevantraal | 0.00004070 |
| 94-47-3 | Benzoic acid, 2-phenylethyl ester | Phenyl Ethyl Benzoate | 0.00003480 |
| 3100-36-5 | Cyclohexadec-8-en-1-one | Globanone ® | 0.00003310 |
| 66072-32-0 | Cyclohexanol, 4-(1,7,7-trimethylbicyclo[2.2.1]hept-2-yl)- | Iso Bornyl Cyclohexanol | 0.00003010 |
| 31906-04-4 | 3-Cyclohexene-1-carboxaldehyde, 4-(4-hydroxy-4-methylpentyl)- | Lyral ® | 0.00002940 |
| 21145-77-7 | Ethanone, 1-(5,6,7,8-tetrahydro-3,5,5,6,8,8-hexamethyl-2-naphthalenyl)- | Musk Plus | 0.00002860 |
| 21145-77-7 | Ethanone, 1-(5,6,7,8-tetrahydro-3,5,5,6,8,8-hexamethyl-2-naphthalenyl)- | Fixolide | 0.00002860 |
| 22442-01-9 | 2-Cyclopentadecen-1-one, 3-methyl- | Muscenone | 0.00002770 |
| 109-29-5 | Oxacycloheptadecan-2-one | Silvanone Ci | 0.00002600 |
| 101-94-0 | Benzeneacetic acid, 4-methylphenyl ester | Para Cresyl Phenyl Acetate | 0.00002330 |
| 102-20-5 | Benzeneacetic acid, 2-phenylethyl ester | Phenyl Ethyl Phenyl Acetate | 0.00002300 |
| 118562-73-5 | Cyclododecaneethanol, β-methyl- | Hydroxyambran | 0.00001800 |
| 103-41-3 | 2-Propenoic acid, 3-phenyl-, phenylmethyl ester | Benzyl Cinnamate | 0.00001050 |
| 4707-47-5 | Benzoic acid, 2,4-dihydroxy-3,6-dimethyl-, methyl ester | Veramoss | 0.00001050 |
| 183551-83-9 | Naphtho[2,1-b]furan-6(7H)-one, 8,9-dihydro-1,5,8-trimethyl-, (8R)- | Myrrhone | 0.00000977 |
| 102-17-0 | Benzeneacetic acid, (4-methoxyphenyl)methyl ester | Para Anisyl Phenyl Acetate | 0.00000813 |
| 120-11-6 | Benzene, 2-methoxy-1-(phenylmethoxy)-4-(1-propen-1-yl)- | Benzyl Iso Eugenol | 0.00000676 |
| 102-22-7 | Benzeneacetic acid, (2E)-3,7-dimethyl-2,6-octadien-1-yl ester | Geranyl Phenylacetate | 0.00000645 |
| 111879-80-2 | Oxacyclohexadec-12-en-2-one, (12E)- | Habanolide 100% | 0.00000431 |
| 87-22-9 | Benzoic acid, 2-hydroxy-, 2-phenylethyl ester | Phenyl Ethyl Salicylate | 0.00000299 |
| 78-37-5 | 2-Propenoic acid, 3-phenyl-, 1-ethenyl-1,5-dimethyl-4-hexen-1-yl ester | Linalyl Cinnamate | 0.00000174 |
| 28645-51-4 | Oxacycloheptadec-10-en-2-one | Ambrettolide | 0.00000139 |
| 123-69-3 | Oxacycloheptadec-8-en-2-one, (8Z)- | Ambrettolide | 0.00000136 |
| 3391-83-1 | 1,7-Dioxacycloheptadecan-8-one | Musk RI | 0.00000057 |
| 68527-79-7 | 7-Octen-2-ol, 8-(1H-indol-1-yl)-2,6-dimethyl- | Indolene | 0.000000445 |
| 54982-83-1 | 1,4-Dioxacyclohexadecane-5,16-dione | Zenolide | 0.00000000834 |
| 105-95-3 | 1,4-Dioxacycloheptadecane-5,17-dione | Ethylene Brassylate | 0.00000000313 |

TABLE 1-continued

Low Volatile Fragrance Materials for Use in the Compositions

| CAS Number | Chemical name | Common Name** | Vapor Pressure (Torr at 25° C.)* |
|---|---|---|---|
| 4159-29-9 | Phenol, 4-[3-(benzoyloxy)-1-propen-1-yl]-2-methoxy- | Coniferyl benzoate | 0.00000000170 |
| 144761-91-1 | Benzoic acid, 2-[(1-hydroxy-3-phenylbutyl)amino]-, methyl ester | Trifone DIPG | 0.00000000093 |

*Vapor Pressures were acquired from Scifinder, which utilizes the ACD Software V.11.02, as described in the Test Methods Section.
**Origin: The low volatile fragrance materials may be obtained from one or more of the following companies: Firmenich (Geneva, Switzerland), Symrise AG (Holzminden, Germany), Givaudan (Argenteuil, France), IFF (Hazlet, New Jersey), Bedoukian (Danbury, Connecticut), Sigma Aldrich (St. Louis, Missouri), Millennium Speciality Chemicals (Olympia Fields, Illinois), Polarone International (Jersey City, New Jersey), and Aroma & Flavor Specialities (Danbury, Connecticut).

In one example, the composition can comprise low volatile fragrance materials comprising at most about 30 wt %, relative to the total weight of the fragrance component. Exemplary low volatile fragrance materials can be selected from the group consisting of the ingredients mentioned in Table 1. However, it is understood by one skilled in the art that other low volatile fragrance materials, not recited in Table 1, would also fall within the scope, so long as they have a vapor pressure <0.001 Torr at 25° C.

Compositions can further comprise one or more volatile fragrance materials having a vapor pressure ≥0.001 Torr at 25° C. (according to the reference program Advanced Chemistry Development (ACD/Labs) Software Version 11.02, (© 1994-2013)). Examples of volatile fragrance materials are listed in the Table 2 hereinafter.

TABLE 2

Volatile Fragrance Materials for Use in the Compositions

| CAS Number | Chemical name | Common Name** | Vapor Pressure (Torr at 25° C.)* |
|---|---|---|---|
| 107-31-3 | Formic acid, methyl ester | Methyl Formate | 732.00000000 |
| 75-18-3 | Methane, 1,1'-thiobis- | Dimethyl Sulfide 1.0% In DEP | 647.00000000 |
| 141-78-6 | Acetic acid ethyl ester | Ethyl Acetate | 112.00000000 |
| 105-37-3 | Propanoic acid, ethyl ester | Ethyl Propionate | 44.50000000 |
| 110-19-0 | Acetic acid, 2-methylpropyl ester | Isobutyl Acetate | 18.00000000 |
| 105-54-4 | Butanoic acid, ethyl ester | Ethyl Butyrate | 13.90000000 |
| 14765-30-1 | 1-Butanol | Butyl Alcohol | 8.52000000 |
| 7452-79-1 | Butanoic acid, 2-methyl-, ethyl ester | Ethyl-2-Methyl Butyrate | 7.85000000 |
| 123-92-2 | 1-Butanol, 3-methyl-, 1-acetate | Iso Amyl Acetate | 5.68000000 |
| 66576-71-4 | Butanoic acid, 2-methyl-, 1-methylethyl ester | Iso Propyl 2-Methylbutyrate | 5.10000000 |
| 110-43-0 | 2-Heptanone | Methyl Amyl Ketone | 4.73000000 |
| 6728-26-3 | 2-Hexenal, (2E)- | Trans-2 Hexenal | 4.62000000 |
| 123-51-3 | 1-Butanol, 3-methyl- | Isoamyl Alcohol | 4.16000000 |
| 1191-16-8 | 2-Buten-1-ol, 3-methyl-, 1-acetate | Prenyl acetate | 3.99000000 |
| 57366-77-5 | 1,3-Dioxolane-2-methanamine, N-methyl- | Methyl Dioxolan | 3.88000000 |
| 7785-70-8 | Bicyclo[3.1.1]hept-2-ene, 2,6,6-trimethyl-, (1R,5R)- | Alpha Pinene | 3.49000000 |
| 79-92-5 | Bicyclo[2.2.1]heptane, 2,2-dimethyl-3-methylene- | Camphene | 3.38000000 |
| 94087-83-9 | 2-Butanethiol, 4-methoxy-2-methyl- | 4-Methoxy-2-Methyl-2-Butanenthiol | 3.31000000 |
| 39255-32-8 | Pentanoic acid, 2-methyl-, ethyl ester | Manzanate | 2.91000000 |
| 3387-41-5 | Bicyclo[3.1.0]hexane, 4-methylene-1-(1-methylethyl)- | Sabinene | 2.63000000 |
| 127-91-3 | Bicyclo[3.1.1]heptane, 6,6-dimethyl-2-methylene- | Beta Pinene | 2.40000000 |
| 105-68-0 | 1-Butanol, 3-methyl-, 1-propanoate | Amyl Propionate | 2.36000000 |
| 123-35-3 | 1,6-Octadiene, 7-methyl-3-methylene- | Myrcene | 2.29000000 |
| 124-13-0 | Octanal | Octyl Aldehyde | 2.07000000 |
| 7392-19-0 | 2H-Pyran, 2-ethenyltetrahydro-2,6,6-trimethyl- | Limetol | 1.90000000 |
| 111-13-7 | 2-Octanone | Methyl Hexyl Ketone | 1.72000000 |

TABLE 2-continued

Volatile Fragrance Materials for Use in the Compositions

| CAS Number | Chemical name | Common Name** | Vapor Pressure (Torr at 25° C.)* |
|---|---|---|---|
| 123-66-0 | Hexanoic acid, ethyl ester | Ethyl Caproate | 1.66000000 |
| 470-82-6 | 2-Oxabicyclo[2.2.2]octane, 1,3,3-trimethyl- | Eucalyptol | 1.65000000 |
| 99-87-6 | Benzene, 1-methyl-4-(1-methylethyl)- | Para Cymene | 1.65000000 |
| 104-93-8 | Benzene, 1-methoxy-4-methyl- | Para Cresyl Methyl Ether | 1.65000000 |
| 13877-91-3 | 1,3,6-Octatriene, 3,7-dimethyl- | Ocimene | 1.56000000 |
| 138-86-3 | Cyclohexene, 1-methyl-4-(1-methylethenyl)- | dl-Limonene | 1.54000000 |
| 5989-27-5 | Cyclohexene, 1-methyl-4-(1-methylethenyl)-, (4R)- | d-limonene | 1.54000000 |
| 106-68-3 | 3-Octanone | Ethyl Amyl Ketone | 1.50000000 |
| 110-41-8 | Undecanal, 2-methyl- | Methyl Nonyl Acetaldehyde | 1.43000000 |
| 142-92-7 | Acetic acid, hexyl ester | Hexyl acetate | 1.39000000 |
| 110-93-0 | 5-Hepten-2-one, 6-methyl- | Methyl Heptenone | 1.28000000 |
| 81925-81-7 | 2-Hepten-4-one, 5-methyl- | Filbertone 1% in TEC | 1.25000000 |
| 3681-71-8 | 3-Hexen-1-ol, 1-acetate, (3Z)- | cis-3-Hexenyl acetate | 1.22000000 |
| 97-64-3 | Propanoic acid, 2-hydroxy-, ethyl ester | Ethyl Lactate | 1.16000000 |
| 586-62-9 | Cyclohexene, 1-methyl-4-(1-methylethylidene)- | Terpineolene | 1.13000000 |
| 51115-64-1 | Butanoic acid, 2-methylbutyl ester | Amyl butyrate | 1.09000000 |
| 106-27-4 | Butanoic acid, 3-methylbutyl ester | Amyl Butyrate | 1.09000000 |
| 99-85-4 | 1,4-Cyclohexadiene, 1-methyl-4-(1-methylethyl)- | Gamma Terpinene | 1.08000000 |
| 18640-74-9 | Thiazole, 2-(2-methylpropyl)- | 2-Isobutylthiazole | 1.07000000 |
| 928-96-1 | 3-Hexen-1-ol, (3Z)- | cis-3-Hexenol | 1.04000000 |
| 100-52-7 | Benzaldehyde | Benzaldehyde | 0.97400000 |
| 141-97-9 | Butanoic acid, 3-oxo-, ethyl ester | Ethyl Acetoacetate | 0.89000000 |
| 928-95-0 | 2-Hexen-1-ol, (2E)- | Trans-2-Hexenol | 0.87300000 |
| 928-94-9 | 2-Hexen-1-ol, (2Z)- | Beta Gamma Hexenol | 0.87300000 |
| 24691-15-4 | Cyclohexane, 3-ethoxy-1,1,5-trimethyl-, cis- (9CI) | Herbavert | 0.85200000 |
| 19872-52-7 | 2-Pentanone, 4-mercapto-4-methyl- | 4-Methyl-4-Mercaptopentan-2-one 1 ppm TEC | 0.84300000 |
| 3016-19-1 | 2,4,6-Octatriene, 2,6-dimethyl-, (4E,6E)- | Allo-Ocimene | 0.81600000 |
| 69103-20-4 | Oxirane, 2,2-dimethyl-3-(3-methyl-2,4-pentadien-1-yl)- | Myroxide | 0.80600000 |
| 189440-77-5 | 4,7-Octadienoic acid, methyl ester, (4E)- | Anapear | 0.77700000 |
| 67633-96-9 | Carbonic acid, (3Z)-3-hexen-1-yl methyl ester | Liffarome ™ | 0.72100000 |
| 123-68-2 | Hexanoic acid, 2-propen-1-yl ester | Allyl Caproate | 0.67800000 |
| 106-72-9 | 5-Heptenal, 2,6-dimethyl- | Melonal | 0.62200000 |
| 106-30-9 | Heptanoic acid, ethyl ester | Ethyl Oenanthate | 0.60200000 |
| 68039-49-6 | 3-Cyclohexene-1-carboxaldehyde, 2,4-dimethyl- | Ligustral or Triplal | 0.57800000 |
| 101-48-4 | Benzene, (2,2-dimethoxyethyl)- | Phenyl Acetaldehyde Dimethyl Acetal | 0.55600000 |
| 16409-43-1 | 2H-Pyran, tetrahydro-4-methyl-2-(2-methyl-1-propen-1-yl)- | Rose Oxide | 0.55100000 |
| 925-78-0 | 3-Nonanone | Ethyl Hexyl Ketone | 0.55100000 |
| 100-47-0 | Benzonitrile | Benzyl Nitrile | 0.52400000 |
| 589-98-0 | 3-Octanol | Octanol-3 | 0.51200000 |
| 58430-94-7 | 1-Hexanol, 3,5,5-trimethyl-, 1-acetate | Iso Nonyl Acetate | 0.47000000 |
| 10250-45-0 | 4-Heptanol, 2,6-dimethyl-, 4-acetate | Alicate | 0.45400000 |
| 105-79-3 | Hexanoic acid, 2-methylpropyl ester | Iso Butyl Caproate | 0.41300000 |
| 2349-07-7 | Propanoic acid, 2-methyl-, hexyl ester | Hexyl isobutyrate | 0.41300000 |
| 23250-42-2 | Cyclohexanecarboxylic acid, 1,4-dimethyl-, methyl ester, trans- | Cyprissate | 0.40500000 |
| 122-78-1 | Benzeneacetaldehyde | Phenyl acetaldehyde | 0.36800000 |

TABLE 2-continued

Volatile Fragrance Materials for Use in the Compositions

| CAS Number | Chemical name | Common Name** | Vapor Pressure (Torr at 25° C.)* |
|---|---|---|---|
| 5405-41-4 | Butanoic acid, 3-hydroxy-, ethyl ester | Ethyl-3-Hydroxy Butyrate | 0.36200000 |
| 105-53-3 | Propanedioic acid, 1,3-diethyl ester | Diethyl Malonate | 0.34400000 |
| 93-58-3 | Benzoic acid, methyl ester | Methyl Benzoate | 0.34000000 |
| 16356-11-9 | 1,3,5-Undecatriene | Undecatriene | 0.33600000 |
| 65405-70-1 | 4-Decenal, (4E)- | Decenal (Trans-4) | 0.33100000 |
| 54546-26-8 | 1,3-Dioxane, 2-butyl-4,4,6-trimethyl- | Herboxane | 0.33000000 |
| 13254-34-7 | 2-Heptanol, 2,6-dimethyl- | Dimethyl-2 6-Heptan-2-ol | 0.33000000 |
| 98-86-2 | Ethanone, 1-phenyl- | Acetophenone | 0.29900000 |
| 93-53-8 | Benzeneacetaldehyde, α-methyl- | Hydratropic aldehyde | 0.29400000 |
| 80118-06-5 | Propanoic acid, 2-methyl-, 1, 3-dimethyl-3-buten-1-yl ester | Iso Pentyrate | 0.28500000 |
| 557-48-2 | 2,6-Nonadienal, (2E,6Z)- | E Z-2,6-Nonadien-1-al | 0.28000000 |
| 24683-00-9 | Pyrazine, 2-methoxy-3-(2-methylpropyl)- | 2-Methoxy-3-Isobutyl Pyrazine | 0.27300000 |
| 104-57-4 | Formic acid, phenylmethyl ester | Benzyl Formate | 0.27300000 |
| 104-45-0 | Benzene, 1-methoxy-4-propyl- | Dihydroanethole | 0.26600000 |
| 491-07-6 | Cyclohexanone, 5-methyl-2-(1-methylethyl)-, (2R,5R)-rel- | Iso Menthone | 0.25600000 |
| 89-80-5 | Cyclohexanone, 5-methyl-2-(1-methylethyl)-, (2R,5S)-rel- | Menthone Racemic | 0.25600000 |
| 2463-53-8 | 2-Nonenal | 2 Nonen-1-al | 0.25600000 |
| 55739-89-4 | Cyclohexanone, 2-ethyl-4,4-dimethyl- | Thuyacetone | 0.25000000 |
| 150-78-7 | Benzene, 1,4-dimethoxy- | Hydroquinone Dimethyl Ether | 0.25000000 |
| 64988-06-3 | Benzene, 1-(ethoxymethyl)-2-methoxy- | Rosacene | 0.24600000 |
| 76-22-2 | Bicyclo[2.2.1]heptan-2-one, 1,7,7-trimethyl- | Camphor gum | 0.22500000 |
| 67674-46-8 | 2-Hexene, 6,6-dimethoxy-2, 5,5-trimethyl- | Methyl pamplemousse | 0.21400000 |
| 112-31-2 | Decanal | Decyl Aldehyde | 0.20700000 |
| 16251-77-7 | Benzenepropanal, β-methyl- | Trifernal | 0.20600000 |
| 93-92-5 | Benzenemethanol, α-methyl-, 1-acetate | Methylphenylcarbinol acetate | 0.20300000 |
| 143-13-5 | Acetic acid, nonyl ester | Nonyl Acetate | 0.19700000 |
| 122-00-9 | Ethanone, 1-(4-methylphenyl)- | Para Methyl Acetophenone | 0.18700000 |
| 24237-00-1 | 2H-Pyran, 6-butyl-3,6-dihydro-2,4-dimethyl- | Gyrane | 0.18600000 |
| 41519-23-7 | Propanoic acid, 2-methyl-, (3Z)-3-hexen-1-yl ester | Hexenyl isobutyrate | 0.18200000 |
| 93-89-0 | Benzoic acid, ethyl ester | Ethyl Benzoate | 0.18000000 |
| 20780-48-7 | 3-Octanol, 3,7-dimethyl-, 3-acetate | Tetrahydro Linalyl Acetate | 0.18000000 |
| 40853-55-2 | 1-Hexanol, 5-methyl-2-(1-methylethyl)-, 1-acetate | Tetrahydro Lavandulyl Acetate | 0.17300000 |
| 933-48-2 | Cyclohexanol, 3,3,5-trimethyl-, (1R,5R)-rel- | Trimethylcyclohexanol | 0.17300000 |
| 35158-25-9 | 2-Hexenal, 5-methyl-2-(1-methylethyl)- | Lactone of Cis Jasmone | 0.17200000 |
| 18479-58-8 | 7-Octen-2-ol, 2,6-dimethyl- | Dihydromyrcenol | 0.16600000 |
| 140-11-4 | Acetic acid, phenylmethyl ester | Benzyl acetate | 0.16400000 |
| 14765-30-1 | Cyclohexanone, 2-(1-methylpropyl)- | 2-sec-Butyl Cyclo Hexanone | 0.16300000 |
| 20125-84-2 | 3-Octen-1-ol, (3Z)- | Octenol | 0.16000000 |
| 142-19-8 | Heptanoic acid, 2-propen-1-yl ester | Allyl Heptoate | 0.16000000 |
| 100-51-6 | Benzenemethanol | Benzyl Alcohol | 0.15800000 |
| 10032-15-2 | Butanoic acid, 2-methyl-, hexyl ester | Hexyl-2-Methyl Butyrate | 0.15800000 |
| 695-06-7 | 2(3H)-Furanone. 5-ethyldihydro- | Gamma Hexalactone | 0.15200000 |
| 21722-83-8 | Cyclohexaneethanol, 1-acetate | Cyclohexyl Ethyl Acetate | 0.15200000 |

TABLE 2-continued

Volatile Fragrance Materials for Use in the Compositions

| CAS Number | Chemical name | Common Name** | Vapor Pressure (Torr at 25° C.)* |
|---|---|---|---|
| 111-79-5 | 2-Nonenoic acid, methyl ester | Methyl-2-Nonenoate | 0.14600000 |
| 16491-36-4 | Butanoic acid, (3Z)-3-hexen-1-yl ester | Cis 3 Hexenyl Butyrate | 0.13500000 |
| 111-12-6 | 2-Octynoic acid, methyl ester | Methyl Heptine Carbonate | 0.12500000 |
| 59323-76-1 | 1,3-Oxathiane, 2-methyl-4-propyl-, (2R,4S)-rel- | Oxane | 0.12300000 |
| 62439-41-2 | Heptanal, 6-methoxy-2,6-dimethyl- | Methoxy Melonal | 0.11900000 |
| 13851-11-1 | Bicyclo[2.2.1]heptan-2-ol, 1,3,3-trimethyl-, 2-acetate | Fenchyl Acetate | 0.11700000 |
| 115-95-7 | 1,6-Octadien-3-ol, 3,7-dimethyl-, 3-acetate | Linalyl acetate | 0.11600000 |
| 18479-57-7 | 2-Octanol, 2,6-dimethyl- | Tetra-Hydro Myrcenol | 0.11500000 |
| 111-87-5 | 1-Octanol | Octyl Alcohol | 0.11400000 |
| 71159-90-5 | 3-Cyclohexene-1-methanethiol, α,α,4-trimethyl- | Grapefruit mercaptan | 0.10500000 |
| 80-25-1 | Cyclohexanemethanol, α,α,4-trimethyl-, 1-acetate | Menthanyl Acetate | 0.10300000 |
| 88-41-5 | Cyclohexanol, 2-(1,1-dimethylethyl)-, 1-acetate | Verdox ™ | 0.10300000 |
| 32210-23-4 | Cyclohexanol, 4-(1,1-dimethylethyl)-, 1-acetate | Vertenex | 0.10300000 |
| 24168-70-5 | Pyrazine, 2-methoxy-3-(1-methylpropyl)- | Methoxyisobutylpyrazine | 0.09950000 |
| 89-79-2 | Cyclohexanol, 5-methyl-2-(1-methylethenyl)-, (1R,2S,5R)- | Iso-Pulegol | 0.09930000 |
| 112-12-9 | 2-Undecanone | Methyl Nonyl Ketone | 0.09780000 |
| 103-05-9 | Benzenepropanol, α,α-dimethyl- | Phenyl Ethyl Dimethyl Carbinol | 0.09770000 |
| 125-12-2 | Bicyclo[2.2.1]heptan-2-ol, 1,7,7-trimethyl-, 2-acetate, (1R,2R,4R)-rel- | Iso Bornyl Acetate | 0.09590000 |
| 78-70-6 | 1,6-Octadien-3-ol, 3,7-dimethyl- | Linalool | 0.09050000 |
| 101-97-3 | Benzeneacetic acid, ethyl ester | Ethyl Phenyl Acetate | 0.08970000 |
| 100-86-7 | Benzeneethanol, α,α-dimethyl- | Dimethyl Benzyl Carbinol | 0.08880000 |
| 188570-78-7 | Cyclopropanecarboxylic acid, (3Z)-3-hexen-1-yl ester | Montaverdi | 0.08640000 |
| 67634-25-7 | 3-Cyclohexene-1-methanol, 3,5-dimethyl-, 1-acetate | Floralate | 0.08500000 |
| 112-44-7 | Undecanal | Undecyl Aldehyde | 0.08320000 |
| 32669-00-4 | Ethanone, 1-(3-cycloocten-1-yl)- | Tanaisone ® | 0.08150000 |
| 98-53-3 | Cyclohexanone, 4-(1,1-dimethylethyl)- | Patchi | 0.07780000 |
| 35854-86-5 | 6-Nonen-1-ol, (6Z)- | cis-6-None-1-ol | 0.07770000 |
| 5331-14-6 | Benzene, (2-butoxyethyl)- | Butyl phenethyl ether | 0.07760000 |
| 80-57-9 | Bicyclo[3.1.1]hept-3-en-2-one, 4,6,6-trimethyl- | Verbenone | 0.07730000 |
| 22471-55-2 | Cyclohexanecarboxylic acid, 2,2,6-trimethyl-, ethyl ester, (1R,6S)-rel- | Thesaron | 0.07670000 |
| 60-12-8 | Benzeneethanol | Phenethyl alcohol | 0.07410000 |
| 106-26-3 | 2,6-Octadienal, 3,7-dimethyl-, (2Z)- | Neral | 0.07120000 |
| 5392-40-5 | 2,6-Octadienal, 3,7-dimethyl- | Citral | 0.07120000 |
| 89-48-5 | Cyclohexanol, 5-methyl-2-(1-methylethyl)-, 1-acetate, (1R,2S,5R)-rel- | Menthyl Acetate | 0.07070000 |
| 119-36-8 | Benzoic acid, 2-hydroxy-, methyl ester | Methyl salicylate | 0.07000000 |
| 4180-23-8 | Benzene, 1-methoxy-4-(1E)-1-propen-1-yl- | Anethol | 0.06870000 |
| 7549-37-3 | 2,6-Octadiene, 1,1-dimethoxy-3,7-dimethyl- | Citral Dimethyl Acetal | 0.06780000 |
| 25225-08-5 | Cyclohexanemethanol, α,3,3-trimethyl-, 1-formate | Aphermate | 0.06780000 |
| 3913-81-3 | 2-Decenal, (2E)- | 2-Decene-1-al | 0.06740000 |

TABLE 2-continued

Volatile Fragrance Materials for Use in the Compositions

| CAS Number | Chemical name | Common Name** | Vapor Pressure (Torr at 25° C.)* |
|---|---|---|---|
| 15373-31-6 | 3-Cyclopentene-1-acetonitrile, 2,2,3-trimethyl- | Cantryl ® | 0.06700000 |
| 6485-40-1 | 2-Cyclohexen-1-one, 2-methyl-5-(1-methylethenyl)-, (5R)- | Laevo carvone | 0.06560000 |
| 16587-71-6 | Cyclohexanone, 4-(1,1-dimethylpropyl)- | Orivone | 0.06490000 |
| 62406-73-9 | 6,10-Dioxaspiro[4.5]decane, 8,8-dimethyl-7-(1-methylethyl)- | Opalal CI | 0.06290000 |
| 3720-16-9 | 2-Cyclohexen-1-one, 3-methyl-5-propyl- | Livescone | 0.06270000 |
| 13816-33-6 | Benzonitrile, 4-(1-methylethyl)- | Cumin Nitrile | 0.06230000 |
| 67019-89-0 | 2,6-Nonadienenitrile | Violet Nitrile | 0.06200000 |
| 53398-85-9 | Butanoic acid, 2-methyl-, (3Z)-3-hexen-1-yl ester | cis-3-Hexenyl Alpha Methyl Butyrate | 0.06130000 |
| 16510-27-3 | Benzene, 1-(cyclopropylmethyl)-4-methoxy- | Toscanol | 0.05870000 |
| 111-80-8 | 2-Nonynoic acid, methyl ester | Methyl Octine Carbonate | 0.05680000 |
| 103-45-7 | Acetic acid, 2-phenylethyl ester | Phenyl Ethyl Acetate | 0.05640000 |
| 13491-79-7 | Cyclohexanol, 2-(1,1-dimethylethyl)- | Verdol | 0.05430000 |
| 7786-44-9 | 2,6-Nonadien-1-ol | 2,6-Nonadien-1-ol | 0.05370000 |
| 103-28-6 | Propanoic acid, 2-methyl-, phenylmethyl ester | Benzyl Iso Butyrate | 0.05130000 |
| 28462-85-3 | Bicyclo[2.2.1]heptan-2-ol, 1,2,3,3-tetramethyl-, (1R,2R,4S)-rel- | Humus Ether | 0.04870000 |
| 122-03-2 | Benzaldehyde, 4-(1-methylethyl)- | Cuminic Aldehyde | 0.04820000 |
| 358331-95-0 | 2,5-Octadien-4-one, 5,6,7-trimethyl-, (2E)- | Pomarose | 0.04810000 |
| 562-74-3 | 3-Cyclohexen-1-ol, 4-methyl-1-(1-methylethyl)- | Terpinenol-4 | 0.04780000 |
| 68527-77-5 | 3-Cyclohexene-1-methanol, 2,4,6-trimethyl- | Isocyclogeraniol | 0.04640000 |
| 35852-46-1 | Pentanoic acid, (3Z)-3-hexen-1-yl ester | Cis-3-Hexenyl Valerate | 0.04580000 |
| 2756-56-1 | Bicyclo[2.2.1]heptan-2-ol, 1,7,7-trimethyl-, 2-propanoate, (1R,2R,4R)-rel- | Iso Bornyl Propionate | 0.04540000 |
| 14374-92-6 | Benzene, 1-methyl-4-(1-methylethyl)-2-(1-propen-1-yl)- | Verdoracine | 0.04460000 |
| 6784-13-0 | 3-Cyclohexene-1-propanal, β,4-dimethyl- | Limonenal | 0.04380000 |
| 41884-28-0 | 1-Hexanol, 5-methyl-2-(1-methylethyl)-, (2R)- | Tetrahydro Lavandulol | 0.04230000 |
| 22457-23-4 | 3-Heptanone, 5-methyl-, oxime | Stemone ® | 0.04140000 |
| 104-50-7 | 2(3H)-Furanone, 5-butyldihydro- | Gamma Octalactone | 0.04080000 |
| 143-08-8 | 1-Nonanol | Nonyl Alcohol | 0.04070000 |
| 67634-00-8 | Acetic acid, 2-(3-methylbutoxy)-, 2-propen-1-yl ester | Allyl Amyl Glycolate | 0.04000000 |
| 464-45-9 | Bicyclo[2.2.1]heptan-2-ol, 1,7,7-trimethyl-, (1S,2R,4S)- | 1-Borneol | 0.03980000 |
| 124-76-5 | Bicyclo[2.2.1]heptan-2-ol, 1,7,7-trimethyl-, (1R,2R,4R)-rel- | 1.7.7-Trimethyl-Bicyclo-1.2.2-Heptanol-2 | 0.03980000 |
| 67874-72-0 | Cyclohexanol, 2-(1,1-dimethylpropyl)-, 1-acetate | Coniferan | 0.03980000 |
| 80-26-2 | 3-Cyclohexene-1-methanol, α,α,4-trimethyl-, 1-acetate | Terpinyl Acetate | 0.03920000 |
| 498-81-7 | Cyclohexanemethanol, α,α,4-trimethyl- | Dihydro Terpineol | 0.03920000 |
| 112-45-8 | 10-Undecenal | Undecylenic aldehyde | 0.03900000 |
| 35044-57-6 | 2,4-Cyclohexadiene-1-carboxylic acid, 2,6,6-trimethyl-, ethyl ester | Ethyl Safranate | 0.03880000 |

TABLE 2-continued

Volatile Fragrance Materials for Use in the Compositions

| CAS Number | Chemical name | Common Name** | Vapor Pressure (Torr at 25° C.)* |
|---|---|---|---|
| 106-21-8 | 1-Octanol, 3,7-dimethyl- | Dimethyl Octanol | 0.03860000 |
| 82461-14-1 | Furan, tetrahydro-2,4-dimethyl-4-phenyl- | Rhubafuran ® | 0.03780000 |
| 56011-02-0 | Benzene, [2-(3-methylbutoxy)ethyl]- | Phenyl Ethyl Isoamyl Ether | 0.03690000 |
| 103-37-7 | Butanoic acid, phenylmethyl ester | Benzyl Butyrate | 0.03660000 |
| 118-61-6 | Benzoic acid, 2-hydroxy-, ethyl ester | Ethyl salicylate | 0.03480000 |
| 98-52-2 | Cyclohexanol, 4-(1,1-dimethylethyl)- | Patchon | 0.03480000 |
| 115-99-1 | 1,6-Octadien-3-ol, 3,7-dimethyl-, 3-formate | Linalyl Formate | 0.03440000 |
| 112-54-9 | Dodecanal | Laurie aldehyde | 0.03440000 |
| 53046-97-2 | 3,6-Nonadien-1-ol, (3Z,6Z)- | 3,6 Nonadien-1-ol | 0.03360000 |
| 76649-25-7 | 3,6-Nonadien-1-ol | 3,6-Nonadien-1-ol | 0.03360000 |
| 1975-78-6 | Decanenitrile | Decanonitrile | 0.03250000 |
| 2216-51-5 | Cyclohexanol, 5-methyl-2-(1-methylethyl)-, (1R,2S,5R)- | L-Menthol | 0.03230000 |
| 103-93-5 | Propanoic acid, 2-methyl-, 4-methylphenyl ester | Para Cresyl iso-Butyrate | 0.03120000 |
| 24717-86-0 | Propanoic acid, 2-methyl-, (1R,2S,4R)-1,7,7-trimethylbicyclo[2.2.1]hept-2-yl ester, rel- | Abierate | 0.03110000 |
| 67845-46-9 | Acetaldehyde, 2-(4-methylphenoxy)- | Aldehyde XI | 0.03090000 |
| 67883-79-8 | 2-Butenoic acid, 2-methyl-, (3Z)-3-hexen-1-yl ester, (2E)- | Cis-3-Hexenyl Tiglate | 0.03060000 |
| 33885-51-7 | Bicyclo[3.1.1]hept-2-ene-2-propanal, 6,6-dimethyl- | Pino Acetaldehyde | 0.03040000 |
| 70214-77-6 | 2-Nonanol, 6,8-dimethyl- | Nonadyl | 0.03010000 |
| 215231-33-7 | Cyclohexanol, 1-methyl-3-(2-methylpropyl)- | Rossitol | 0.02990000 |
| 120-72-9 | 1H-Indole | Indole | 0.02980000 |
| 2463-77-6 | 2-Undecenal | 2-Undecene-1-al | 0.02970000 |
| 675-09-2 | 2H-Pyran-2-one, 4,6-dimethyl- | Levistamel | 0.02940000 |
| 98-55-5 | 3-Cyclohexene-1-methanol, α,α,4-trimethyl- | alpha-Terpineol | 0.02830000 |
| 81786-73-4 | 3-Hepten-2-one, 3,4,5,6,6-pentamethyl-, (3Z)- | Koavone | 0.02750000 |
| 39212-23-2 | 2(3H)-Furanone, 5-butyldihydro-4-methyl- | Methyl Octalactone | 0.02700000 |
| 53767-93-4 | 7-Octen-2-ol, 2,6-dimethyl-, 2-acetate | Dihydro Terpinyl Acetate | 0.02690000 |
| 104-55-2 | 2-Propenal, 3-phenyl- | Cinnamic Aldehyde | 0.02650000 |
| 144-39-8 | 1,6-Octadien-3-ol, 3,7-dimethyl-, 3-propanoate | Linalyl Propionate | 0.02630000 |
| 61931-80-4 | 1,6-Nonadien-3-ol, 3,7-dimethyl-, 3-acetate | 3,7-Dimethyl-1,6-nonadien-3-yl acetate | 0.02630000 |
| 65443-14-3 | Cyclopentanone, 2,2,5-trimethyl-5-pentyl- | veloutone | 0.02610000 |
| 141-12-8 | 2,6-Octadien-1-ol, 3,7-dimethyl-, 1-acetate, (2Z)- | Neryl Acetate | 0.02560000 |
| 105-87-3 | 2,6-Octadien-1-ol, 3,7-dimethyl-, 1-acetate, (2E)- | Geranyl acetate | 0.02560000 |
| 68141-17-3 | Undecane, 1,1-dimethoxy-2-methyl- | Methyl Nonyl Acetaldehyde Dimethyl Acetal | 0.02550000 |
| 2206-94-2 | Benzenemethanol, α-methylene-, 1-acetate | Indocolore | 0.02550000 |
| 123-11-5 | Benzaldehyde, 4-methoxy- | Anisic aldehyde | 0.02490000 |
| 57576-09-7 | Cyclohexanol, 5-methyl-2-(1-methylethenyl)-, 1-acetate, (1R,2S,5R)- | Iso Pulegol Acetate | 0.02480000 |
| 51566-62-2 | 6-Octenenitrile, 3,7-dimethyl- | Citronellyl Nitrile | 0.02470000 |
| 30385-25-2 | 6-Octen-2-ol, 2,6-dimethyl- | Dihydromyrcenol | 0.02440000 |
| 101-84-8 | Benzene, 1,1'-oxybis- | Diphenyl Oxide | 0.02230000 |
| 136-60-7 | Benzoic acid, butyl ester | 136-60-7 | 0.02170000 |
| 93939-86-7 | 5,8-Methano-2H-1-benzopyran, 6-ethylideneoctahydro- | Rhuboflor | 0.02120000 |
| 83926-73-2 | Cyclohexanepropanol, α,α-dimethyl- | Coranol | 0.02100000 |

TABLE 2-continued

Volatile Fragrance Materials for Use in the Compositions

| CAS Number | Chemical name | Common Name** | Vapor Pressure (Torr at 25° C.)* |
|---|---|---|---|
| 125109-85-5 | Benzenepropanal, β-methyl-3-(1-methylethyl)- | Florhydral | 0.02070000 |
| 104-21-2 | Benzenemethanol, 4-methoxy-, 1-acetate | Anisyl Acetate | 0.02050000 |
| 2563-07-7 | Phenol, 2-ethoxy-4-methyl- | Ultravanil | 0.02030000 |
| 7493-57-4 | Benzene, [2-(1-propoxyethoxy)ethyl]- | Acetaldehyde | 0.01990000 |
| 141-25-3 | 7-Octen-1-ol, 3,7-dimethyl- | Rhodinol | 0.01970000 |
| 216970-21-7 | Bicyclo[4.3.1]decane, 3-methoxy-7,7-dimethyl-10-methylene- | 3-Methoxy-7,7-dimethyl-10-methylenebicyclo [4.3.1] decane | 0.01960000 |
| 319002-92-1 | Propanoic acid, 2-(1,1-dimethylpropoxy)-, propyl ester, (2S)- | Sclareolate ® | 0.01960000 |
| 85-91-6 | Benzoic acid, 2-(methylamino)-, methyl ester | Dimethyl anthranilate | 0.01930000 |
| 7540-51-4 | 6-Octen-1-ol, 3,7-dimethyl-, (3S)- | L-Citronellol | 0.01830000 |
| 543-39-5 | 7-Octen-2-ol, 2-methyl-6-methylene- | Myrcenol | 0.01820000 |
| 18479-54-4 | 4,6-Octadien-3-ol, 3,7-dimethyl- | Muguol | 0.01800000 |
| 1209-61-6 | 5-Oxatricyclo[8.2.0.04,6] dodecane, 4,9,12,12-tetramethyl- | Tobacarol | 0.01730000 |
| 57934-97-1 | 2-Cyclohexene-1-carboxylic acid, 2-ethyl-6,6-dimethyl-, ethyl ester | Givescone | 0.01710000 |
| 79-77-6 | 3-Buten-2-one, 4-(2,6,6-trimethyl-1-cyclohexen-1-yl)-, (3E)- | beta-Ionone | 0.01690000 |
| 64001-15-6 | 4,7-Methano-1H-inden-5-ol, octahydro-, 5-acetate | Dihydro Cyclacet | 0.01630000 |
| 134-20-3 | Benzoic acid, 2-amino-, methyl ester | Methyl anthranilate | 0.01580000 |
| 154171-77-4 | Spiro[1,3-dioxolane-2 , 8'(5'H)-[2H-2,4a] methanonaphthalene], hexahydro-1',1',5',5'-tetramethyl-, (2'S,4'aS,8'aS)-(9CI) | Ysamber K ® | 0.01470000 |
| 154171-76-3 | Spiro[1,3-dioxolane-2,8'(5'H)-[2H-2,4a]methanonaphthalene], hexahydro-1',1',5',5'-tetramethyl- | Ysamber | 0.01470000 |
| 127-41-3 | 3-Buten-2-one, 4-(2,6,6-trimethyl-2-cyclohexen-1-yl)-, (3E)- | alpha-Ionone | 0.01440000 |
| 151-05-3 | Benzeneethanol, α,α-dimethyl-, 1-acetate | Dimethyl Benzyl Carbinyl Acetate | 0.01390000 |
| 2500-83-6 | 4,7-Methano-1H-inden-5-ol, 3a,4,5,6,7,7a-hexahydro-, 5-acetate | Flor Acetate | 0.01370000 |
| 150-84-5 | 6-Octen-1-ol, 3,7-dimethyl-, 1-acetate | Citronellyl acetate | 0.01370000 |
| 30310-41-9 | 2H-Pyran, tetrahydro-2-methyl-4-methylene-6-phenyl- | Pelargene | 0.01350000 |
| 68845-00-1 | Bicyclo[3.3.1]nonane, 2-ethoxy-2,6,6-trimethyl-9-methylene- | Boisiris | 0.01350000 |
| 106-24-1 | 2,6-Octadien-1-ol, 3,7-dimethyl-, (2E)- | Geraniol | 0.01330000 |
| 75975-83-6 | Bicyclo[7.2.0]undec-4-ene, 4,11,11-trimethyl-8-methylene-, (1R,4E,9S)- | Vetyvenal | 0.01280000 |
| 19870-74-7 | 1H-3a,7-Methanoazulene, octahydro-6-methoxy-3,6,8,8-tetramethyl-, (3R,3aS,6S,7R,8aS)- | Cedryl methyl ether | 0.01280000 |
| 87-44-5 | Bicyclo[7.2.0]undec-4-ene, 4,11,11-trimethyl-8-methylene-, (1R,4E,9S)- | Caryophyllene Extra | 0.01280000 |

TABLE 2-continued

Volatile Fragrance Materials for Use in the Compositions

| CAS Number | Chemical name | Common Name** | Vapor Pressure (Torr at 25° C.)* |
|---|---|---|---|
| 54440-17-4 | 1H-Inden-1-one, 2,3-dihydro-2,3,3-trimethyl- | Safraleine | 0.01260000 |
| 110-98-5 | 2-Propanol, 1,1'-oxybis- | Ambrocenide | 0.01250000 |
| 41890-92-0 | 2-Octanol, 7-methoxy-3,7-dimethyl- | Osyrol ® | 0.01250000 |
| 71077-31-1 | 4,9-Decadienal, 4,8-dimethyl- | Floral Super | 0.01230000 |
| 65-85-0 | Benzoic Acid | Benzoic Acid | 0.01220000 |
| 61444-38-0 | 3-Hexenoic acid, (3Z)-3-hexen-1-yl ester, (3Z)- | cis-3-hexenyl-cis-3-hexenoate | 0.01220000 |
| 116044-44-1 | Bicyclo[2.2.1]hept-5-ene-2-carboxylic acid, 3-(1-methylethyl)-, ethyl ester, (1R,2S,3S,4S)-rel- | Herbanate | 0.01210000 |
| 104-54-1 | 2-Propen-1-ol, 3-phenyl- | Cinnamic alcohol | 0.01170000 |
| 78-35-3 | Propanoic acid, 2-methyl-, 1-ethenyl-1,5-dimethyl-4-hexen-1-yl ester | Linalyl isobutyrate | 0.01170000 |
| 23495-12-7 | Ethanol, 2-phenoxy-, 1-propanoate | Phenoxy Ethyl Propionate | 0.01130000 |
| 103-26-4 | 2-Propenoic acid, 3-phenyl-, methyl ester | Methyl Cinnamate | 0.01120000 |
| 67634-14-4 | Benzenepropanal, 2-ethyl-$\alpha$,$\alpha$-dimethyl- | Florazon (ortho-isomer) | 0.01110000 |
| 5454-19-3 | Propanoic acid, decyl ester | N-Decyl Propionate | 0.01100000 |
| 93-16-3 | Benzene, 1,2-dimethoxy-4-(1-propen-1-yl)- | Methyl Iso Eugenol | 0.01100000 |
| 81782-77-6 | 3-Decen-5-ol, 4-methyl- | 4-Methyl-3-decen-5-ol | 0.01070000 |
| 97-53-0 | Phenol, 2-methoxy-4-(2-propen-1-yl)- | Eugenol | 0.01040000 |
| 120-57-0 | 1,3-Benzodioxole-5-carboxaldehyde | Heliotropin | 0.01040000 |
| 4826-62-4 | 2-Dodecenal | 2 Dodecene-1-al | 0.01020000 |
| 20407-84-5 | 2-Dodecenal, (2E)- | Aldehyde Mandarin | 0.01020000 |
| 5462-06-6 | Benzenepropanal, 4-methoxy-$\alpha$-methyl- | Canthoxal | 0.01020000 |
| 94-60-0 | 1,4-Cyclohexanedicarboxylic acid, 1,4-dimethyl ester | Dimethyl 1,4-cyclohexanedicarboxylate | 0.01020000 |
| 57378-68-4 | 2-Buten-1-one, 1-(2,6,6-trimethyl-3-cyclohexen-1-yl)- | delta-damascone | 0.01020000 |
| 17283-81-7 | 2-Butanone, 4-(2,6,6-trimethyl-1-cyclohexen-1-yl)- | Dihydro Beta Ionone | 0.01020000 |
| 1885-38-7 | 2-Propenenitrile, 3-phenyl-, (2E)- | Cinnamalva | 0.01010000 |
| 103-48-0 | Propanoic acid, 2-methyl-, 2-phenylethyl ester | Phenyl Ethyl Iso Butyrate | 0.00994000 |
| 488-10-8 | 2-Cyclopenten-1-one, 3-methyl-2-(2Z)-2-penten-1-yl- | Cis Jasmone | 0.00982000 |
| 7492-67-3 | Acetaldehyde, 2-[(3,7-dimethyl-6-octen-1-yl)oxy]- | Citronellyloxyacetaldehyde | 0.00967000 |
| 68683-20-5 | 1-Cyclohexene-1-ethanol, 4-(1-methylethyl)-, 1-formate | Iso Bergamate | 0.00965000 |
| 3025-30-7 | 2,4-Decadienoic acid, ethyl ester, (2E,4Z)- | Ethyl 2,4-Decadienoate | 0.00954000 |
| 103-54-8 | 2-Propen-1-ol, 3-phenyl-, 1-acetate | Cinnamyl Acetate | 0.00940000 |
| 6790-58-5 | Naphtho[2,1-b]furan, dodecahydro-3a,6,6,9a-tetramethyl-, (3aR,5aS,9aS,9bR)- | Synambran | 0.00934000 |
| 18127-01-0 | Benzenepropanal, 4-(1,1-dimethylethyl)- | Bourgeonal | 0.00934000 |
| 3738-00-9 | Naphtho[2,1-b]furan, dodecahydro-3a,6,6,9a-tetramethyl- | Ambroxan | 0.00934000 |
| 51519-65-4 | 1,4-Methanonaphthalen-5(1H)-one, 4,4a,6,7,8,8a-hexahydro- | Tamisone | 0.00932000 |
| 148-05-1 | Dodecanoic acid, 12-hydroxy-, $\lambda$-lactone (6CI, 7CI); 1,12- | Dodecalactone | 0.00931000 |
| 2705-87-5 | Cyclohexanepropanoic acid, 2-propen-1-yl ester | Allyl Cyclohexane Propionate | 0.00925000 |

TABLE 2-continued

Volatile Fragrance Materials for Use in the Compositions

| CAS Number | Chemical name | Common Name** | Vapor Pressure (Torr at 25° C.)* |
|---|---|---|---|
| 7011-83-8 | 2(3H)-Furanone, 5-hexyldihydro-5-methyl- | Lactojasmone ® | 0.00885000 |
| 61792-11-8 | 2,6-Nonadienenitrile, 3,7-dimethyl- | Lemonile ® | 0.00884000 |
| 692-86-4 | 10-Undecenoic acid, ethyl ester | Ethyl Undecylenate | 0.00882000 |
| 103-95-7 | Benzenepropanal, α-methyl-4-(1-methylethyl)- | Cymal | 0.00881000 |
| 94201-19-1 | 1-Oxaspiro[4.5]decan-2-one, 8-methyl- | Methyl Laitone 10% TEC | 0.00872000 |
| 104-61-0 | 2(3H)-Furanone, dihydro-5-pentyl- | γ-Nonalactone | 0.00858000 |
| 706-14-9 | 2(3H)-Furanone, 5-hexyldihydro- | γ-Decalactone | 0.00852000 |
| 24720-09-0 | 2-Buten-1-one, 1-(2,6,6-trimethyl-2-cyclohexen-1-yl)-, (2E)- | α-Damascone | 0.00830000 |
| 39872-57-6 | 2-Buten-1-one, 1-(2,4,4-trimethyl-2-cyclohexen-1-yl)-, (2E)- | Isodamascone | 0.00830000 |
| 705-86-2 | 2H-Pyran-2-one, tetrahydro-6-pentyl- | Decalactone | 0.00825000 |
| 67634-15-5 | Benzenepropanal, 4-ethyl-α,α-dimethyl- | Floralozone | 0.00808000 |
| 40527-42-2 | 1,3-Benzodioxole, 5-(diethoxymethyl)- | Heliotropin Diethyl Acetal | 0.00796000 |
| 56973-85-4 | 4-Penten-1-one, 1-(5,5-dimethyl-1-cyclohexen-1-yl)- | Neobutenone α | 0.00763000 |
| 128-51-8 | Bicyclo[3.1.1]hept-2-ene-2-ethanol, 6,6-dimethyl-, 2-acetate | Nopyl Acetate | 0.00751000 |
| 103-36-6 | 2-Propenoic acid, 3-phenyl-, ethyl ester | Ethyl Cinnamate | 0.00729000 |
| 5182-36-5 | 1,3-Dioxane, 2,4,6-trimethyl-4-phenyl- | Floropal ® | 0.00709000 |
| 42604-12-6 | Cyclododecane, (methoxymethoxy)- | Boisambrene | 0.00686000 |
| 33885-52-8 | Bicyclo[3.1.1]hept-2-ene-2-propanal, α,α,6,6-tetramethyl- | Pinyl Iso Butyrate Alpha | 0.00685000 |
| 3288-99-1 | Benzeneacetonitrile, 4-(1,1-dimethylethyl)- | Marenil CI | 0.00665000 |
| 35044-68-9 | 2-Buten-1-one, 1-(2,6,6-trimethyl-1-cyclohexen-1-yl)- | beta-Damascone | 0.00655000 |
| 41724-19-0 | 1,4-Methanonaphthalen-6(2H)-one, octahydro-7-methyl- | Plicatone | 0.00652000 |
| 75147-23-8 | Bicyclo[3.2.1]octan-8-one, 1,5-dimethyl-, oxime | Buccoxime ® | 0.00647000 |
| 495-62-5 | Cyclohexene, 4-(1,5-dimethyl-4-hexen-1-ylidene)-1-methyl- | Bisabolene | 0.00630000 |
| 2785-87-7 | Phenol, 2-methoxy-4-propyl- | Dihydro Eugenol | 0.00624000 |
| 87-19-4 | Benzoic acid, 2-hydroxy-, 2-methylpropyl ester | Iso Butyl Salicylate | 0.00613000 |
| 4430-31-3 | 2H-1-Benzopyran-2-one, octahydro- | Octahydro Coumarin | 0.00586000 |
| 38462-22-5 | Cyclohexanone, 2-(1-mercapto-1-methylethyl)-5-methyl- | Ringonol 50 TEC | 0.00585000 |
| 77-83-8 | 2-Oxiranecarboxylic acid, 3-methyl-3-phenyl-, ethyl ester | Ethylmethylphenylglycidate | 0.00571000 |
| 37677-14-8 | 3-Cyclohexene-1-carboxaldehyde, 4-(4-methyl-3-penten-1-yl)- | Iso Hexenyl Cyclohexenyl Carboxaldehyde | 0.00565000 |
| 103-60-6 | Propanoic acid, 2-methyl-, 2-phenoxyethyl ester | Phenoxy Ethyl iso-Butyrate | 0.00562000 |
| 18096-62-3 | Indeno[1,2-d]-1,3-dioxin, 4,4a,5,9b-tetrahydro- | Indoflor ® | 0.00557000 |
| 63500-71-0 | 2H-Pyran-4-ol, tetrahydro-4-methyl-2-(2-methylpropyl)- | Florosa Q | 0.00557000 |
| 65405-84-7 | Cyclohexanebutanal, α,2,6,6-tetramethyl- | Cetonal ® | 0.00533000 |
| 10339-55-6 | 1,6-Nonadien-3-ol, 3,7-dimethyl- | Ethyl linalool | 0.00520000 |

TABLE 2-continued

Volatile Fragrance Materials for Use in the Compositions

| CAS Number | Chemical name | Common Name** | Vapor Pressure (Torr at 25° C.)* |
|---|---|---|---|
| 23267-57-4 | 3-Buten-2-one, 4-(2,2,6-trimethyl-7-oxabicyclo[4.1.0]hept-1-yl)- | Ionone Epoxide Beta | 0.00520000 |
| 97-54-1 | Phenol, 2-methoxy-4-(1-propen-1-yl)- | Isoeugenol | 0.00519000 |
| 67663-01-8 | 2(3H)-Furanone, 5-hexyldihydro-4-methyl- | Peacholide | 0.00512000 |
| 33885-52-8 | Bicyclo[3.1.1]hept-2-ene-2-propanal, α,α,6,6-tetramethyl- | Pinyl Iso Butyrate Alpha | 0.00512000 |
| 23696-85-7 | 2-Buten-1-one, 1-(2,6,6-trimethyl-1,3-cyclohexadien-1-yl)- | Damascenone | 0.00503000 |
| 80-71-7 | 2-Cyclopenten-1-one, 2-hydroxy-3-methyl- | Maple Lactone | 0.00484000 |
| 67662-96-8 | Propanoic acid, 2,2-dimethyl-, 2-phenylethyl ester | Pivarose Q | 0.00484000 |
| 2437-25-4 | Dodecanenitrile | Clonal | 0.00480000 |
| 141-14-0 | 6-Octen-1-ol, 3,7-dimethyl-, 1-propanoate | Citronellyl Propionate | 0.00469000 |
| 55066-49-4 | Benzenepentanal, β-methyl- | Mefranal | 0.00455000 |
| 7493-74-5 | Acetic acid, 2-phenoxy-, 2-propen-1-yl ester | Allyl Phenoxy Acetate | 0.00454000 |
| 80-54-6 | Benzenepropanal, 4-(1,1-dimethylethyl)-α-methyl- | Lilial ® | 0.00444000 |
| 86803-90-9 | 4,7-Methano-1H-indene-2-carboxaldehyde, octahydro-5-methoxy- | Scentenal ® | 0.00439000 |
| 18871-14-2 | Pentitol, 1,5-anhydro-2,4-dideoxy-2-pentyl-, 3-acetate | Jasmal | 0.00434000 |
| 58567-11-6 | Cyclododecane, (ethoxymethoxy)- | Boisambren Forte | 0.00433000 |
| 94400-98-3 | Naphth[2,3-b]oxirene, 1a,2,3,4,5,6,7,7a-octahydro-1a,3,3,4,6,6-hexamethyl-, (1aR,4S,7aS)-rel- | Molaxone | 0.00425000 |
| 79-69-6 | 3-Buten-2-one, 4-(2,5,6,6-tetramethyl-2-cyclohexen-1-yl)- | alpha-Irone | 0.00419000 |
| 65442-31-1 | Quinoline, 6-(1-methylpropyl)- | Iso Butyl Quinoline | 0.00408000 |
| 87731-18-8 | Carbonic acid, 4-cycloocten-1-yl methyl ester | Violiff | 0.00401000 |
| 173445-65-3 | 1H-Indene-5-propanal, 2,3-dihydro-3,3-dimethyl- | Hivernal (A-isomer) | 0.00392000 |
| 23911-56-0 | Ethanone, 1-(3-methyl-2-benzofuranyl)- | Nerolione | 0.00383000 |
| 52474-60-9 | 3-Cyclohexene-1-carboxaldehyde, 1-methyl-3-(4-methyl-3-penten-1-yl)- | Precyclemone B | 0.00381000 |
| 139539-66-5 | 6-Oxabicyclo[3.2.1]octane, 5-methyl-1-(2,2,3-trimethyl-3-cyclopenten-1-yl)- | Cassifix | 0.00381000 |
| 32764-98-0 | 2H-Pyran-2-one, tetrahydro-6-(3-penten-1-yl)- | Jasmolactone | 0.00355000 |
| 78417-28-4 | 2,4,7-Decatrienoic acid, ethyl ester | Ethyl 2,4,7-decatrienoate | 0.00353000 |
| 140-26-1 | Butanoic acid, 3-methyl-, 2-phenylethyl ester | Beta Phenyl Ethyl Isovalerate | 0.00347000 |
| 41816-03-9 | Spiro[1,4-methanonaphthalene-2(1H),2'-oxirane], 3,4,4a,5,8,8a-hexahydro-3',7-dimethyl- | Rhubofix ® | 0.00332000 |
| 7070-15-7 | Ethanol, 2-[[(1R,2R,4R)-1,7,7-trimethylbicyclo[2.2.1]hept-2-yl]oxy]-, rel- | Arbanol | 0.00326000 |
| 93-29-8 | Phenol, 2-methoxy-4-(1-propen-1-yl)-, 1-acetate | Iso Eugenol Acetate | 0.00324000 |
| 476332-65-7 | 2H-Indeno[4,5-b]furan, decahydro-2,2,6,6,7,8,8-heptamethyl- | Amber Xtreme Compound 1 | 0.00323000 |
| 68901-15-5 | Acetic acid, 2-(cyclohexyloxy)-, 2-propen-1-yl ester | Cyclogalbanate | 0.00323000 |

TABLE 2-continued

Volatile Fragrance Materials for Use in the Compositions

| CAS Number | Chemical name | Common Name** | Vapor Pressure (Torr at 25° C.)* |
|---|---|---|---|
| 107-75-5 | Octanal, 7-hydroxy-3,7-dimethyl- | Hydroxycitronellal | 0.00318000 |
| 217816-75-6 | Naphtho[2,1-b]furan, 9b-ethyldodecahydro-3a,7,7-trimethyl- | Grisalva | 0.00305000 |
| 313973-37-4 | 1,6-Heptadien-3-one, 2-cyclohexyl- | Pharaone | 0.00298000 |
| 137-00-8 | 5-Thiazoleethanol, 4-methyl- | Sulfurol | 0.00297000 |
| 7779-30-8 | 1-Penten-3-one, 1-(2,6,6-trimethyl-2-cyclohexen-1-yl)- | Methyl Ionone | 0.00286000 |
| 127-51-5 | 3-Buten-2-one, 3-methyl-4-(2,6,6-trimethyl-2-cyclohexen-1-yl)- | Isoraldeine Pure | 0.00282000 |
| 72903-27-6 | 1,4-Cyclohexanedicarboxylic acid, 1,4-diethyl ester | Fructalate | 0.00274000 |
| 104-67-6 | 2(3H)-Furanone, 5-heptyldihydro- | gamma-Undecalactone (racemic) | 0.00271000 |
| 1205-17-0 | 1,3-Benzodioxole-5-propanal, α-methyl- | Helional | 0.00270000 |
| 33704-61-9 | 4H-Inden-4-one, 1,2,3,5,6,7-hexahydro-1,1,2,3,3-pentamethyl- | Cashmeran | 0.00269000 |
| 36306-87-3 | Cyclohexanone, 4-(1-ethoxyethenyl)-3,3,5,5-tetramethyl- | Kephalis | 0.00269000 |
| 97384-48-0 | Benzenepropanenitrile, α-ethenyl-α-methyl- | Citrowanil ® B | 0.00265000 |
| 141-13-9 | 9-Undecenal, 2,6,10-trimethyl- | Adoxal | 0.00257000 |
| 2110-18-1 | Pyridine, 2-(3-phenylpropyl)- | Corps Racine VS | 0.00257000 |
| 27606-09-3 | Indeno[1,2-d]-1,3-dioxin, 4,4a,5,9b-tetrahydro-2,4-dimethyl- | Magnolan | 0.00251000 |
| 67634-20-2 | Propanoic acid, 2-methyl-, 3a,4,5,6,7,7a-hexahydro-4,7-methano-1H-inden-5-yl ester | Cyclabute | 0.00244000 |
| 65405-72-3 | 1-Naphthalenol, 1,2,3,4,4a,7,8,8a-octahydro-2,4a,5,8a-tetramethyl-, 1-formate | Oxyoctaline Formate | 0.00236000 |
| 103694-68-4 | Benzenepropanol, β,β,3-trimethyl- | Majantol | 0.00224000 |
| 13215-88-8 | 2-Cyclohexen-1-one, 4-(2-buten-1-ylidene)-3,5,5-trimethyl- | Tabanone Coeur | 0.00223000 |
| 25152-85-6 | 3-Hexen-1-ol, 1-benzoate, (3Z)- | Cis-3-Hexenyl Benzoate | 0.00203000 |
| 121-33-5 | Benzaldehyde, 4-hydroxy-3-methoxy- | Vanillin | 0.00194000 |
| 77-54-3 | 1H-3a,7-Methanoazulen-6-ol, octahydro-3, 6,8,8-tetramethyl-, 6-acetate, (3R, 3aS,6R,7R,8aS)- | Cedac | 0.00192000 |
| 76842-49-4 | 4,7-Methano-1H-inden-6-ol, 3a,4,5,6,7,7a-hexahydro-8,8-dimethyl-, 6-propanoate | Frutene | 0.00184000 |
| 121-39-1 | 2-Oxiranecarboxylic acid, 3-phenyl-, ethyl ester | Ethyl Phenyl Glycidate | 0.00184000 |
| 211299-54-6 | 4H-4a,9-Methanoazuleno[5,6-d]-1,3-dioxole, octahydro-2,2,5,8,8,9a-hexamethyl-, (4aR,5R,7aS,9R)- | Ambrocenide | 0.00182000 |
| 10094-34-5 | Butanoic acid, 1,1-dimethyl-2-phenylethyl ester | Dimethyl benzyl carbinyl butyrate | 0.00168000 |
| 40785-62-4 | Cyclododeca[c]furan, 1,3,3a,4,5,6,7,8,9,10,11,13a-dodecahydro- | Muscogene | 0.00163000 |
| 75490-39-0 | Benzenebutanenitrile, α,α,γ-trimethyl- | Khusinil | 0.00162000 |
| 55418-52-5 | 2-Butanone, 4-(1,3-benzodioxol-5-yl)- | Dulcinyl | 0.00161000 |

TABLE 2-continued

Volatile Fragrance Materials for Use in the Compositions

| CAS Number | Chemical name | Common Name** | Vapor Pressure (Torr at 25° C.)* |
|---|---|---|---|
| 3943-74-6 | Benzoic acid, 4-hydroxy-3-methoxy-, methyl ester | Carnaline | 0.00157000 |
| 72089-08-8 | 3-Cyclopentene-1-butanol, β,2,2,3-tetramethyl-2-Methyl-4-(2,2,3-trimethyl-3-cyclopenten-1-yl)butanol | Brahmanol | 0.00154000 |
| 3155-71-3 | 2-Butenal, 2-methyl-4-(2,6,6-trimethyl-1-cyclohexen-1-yl)- | Boronal | 0.00147000 |
| 41199-20-6 | 2-Naphthalenol, decahydro-2,5,5-trimethyl- | Ambrinol | 0.00140000 |
| 107-74-4 | 1,7-Octanediol, 3,7-dimethyl- | Hydroxyol | 0.00139000 |
| 91-64-5 | 2H-1-Benzopyran-2-one | Coumarin | 0.00130000 |
| 68901-32-6 | 1,3-Dioxolane, 2-[6-methyl-8-(1-methylethyl)bicyclo[2.2.2]oct-5-en-2-yl]- | Glycolierral | 0.00121000 |
| 68039-44-1 | Propanoic acid, 2,2-dimethyl-, 3a,4,5,6,7,7a-hexahydro-4,7-methano-1H-inden-6-yl ester | Pivacyclene | 0.00119000 |
| 106-29-6 | Butanoic acid, (2E)-3,7-dimethyl-2,6-octadien-1-yl ester | Geranyl Butyrate | 0.00116000 |
| 5471-51-2 | 2-Butanone, 4-(4-hydroxyphenyl)- | Raspberry ketone | 0.00106000 |
| 109-42-2 | 10-Undecenoic acid, butyl ester | Butyl Undecylenate | 0.00104000 |

*Vapor Pressures were acquired from Scifinder, which utilizes the ACD Software V.11.02, as described in the Test Methods Section.
**Origin: The low volatile fragrance materials may be obtained from one or more of the following companies: Firmenich (Geneva, Switzerland), Symrise AG (Holzminden, Germany), Givaudan (Argenteuil, France), IFF (Hazlet, New Jersey), Bedoukian (Danbury, Connecticut), Sigma Aldrich (St. Louis, Missouri), Millennium Speciality Chemicals (Olympia Fields, Illinois), Polarone International (Jersey City, New Jersey) and Aroma & Flavor Specialities (Danbury, Connecticut).

Other volatile fragrance materials, not recited in Table 2, would also fall within the scope, so long as they have a vapor pressure of ≥0.001 Torr at 25° C.

Modulators & Co-Modulators

Compositions can comprise at least one non-odorous alkoxylated glucoside modulator. The non-odorous alkoxylated glucoside modulator can be selected from the non-limiting group consisting of methyl glucoside polyol, ethyl glucoside polyol, and propyl glucoside polyol. The modulator can be a compound of formula (I):

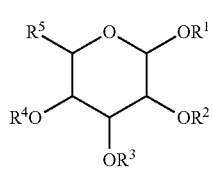

(I)

wherein:

$R^1$ is hydrogen, alkyl, alkenyl or alkynyl;

$R^2$ is selected from hydrogen, alkyl, alkenyl, alkynyl, —[$R^6R^7(R^8)O]_wR^9$, wherein w is from 1 to 10, or 2 to 9;

$R^3$ is selected from hydrogen, alkyl, alkenyl, alkynyl, —[$R^6R^7(R^8)O]_yR^9$, wherein y is from 1 to 10, or 2 to 9;

$R^4$ is selected from hydrogen, alkyl, alkenyl, alkynyl, —[$R^6R^7(R^8)O]_xR^9$, wherein x is from 1 to 10, or 2 to 9;

$R^5$ is selected from hydrogen, alkyl, alkenyl, alkynyl, —$R^6OR^9$, —$R^6O[R^6R^7(R^8)O]_zR^9$, wherein z is from 1 to 10, or 2 to 9;

each $R^6$ and $R^7$ are independently selected from alkylene, alkenylene, or alkynylene; and each $R^8$ and $R^9$ is independently selected from hydrogen or alkyl, In an embodiment of formula (I), wherein the sum of w, y, x and z is equal to 4 to 40, 8 to 36, 10 to 32, or 10 to 28.

In one example, the modulator is Undecyl Glucoside and is available under the tradename Simulsol® SL 11 W from SEPPIC, France.

In another example of formula (I), the modulator is a compound of formula (Ia):

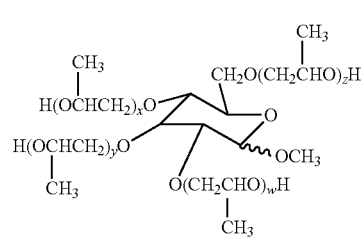

(Ia)

In an embodiment of formula (Ia), wherein w+x+y+z is equal to 4 to 40, 8 to 36, 10 to 32, or 10 to 28, or combinations thereof. The modulator ican be, for example, a PPG-10 Methyl Glucose Ether available under the tradename Glucam™ P-10 or Ethoxylated Methyl Glucose Ether and is available under the tradename Glucam™ E-20, respectively, from Lubrizol (USA).

In another example, the modulator is a compound of formula (II):

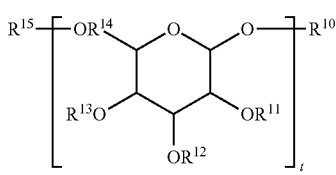

wherein:

$R^{10}$ is hydrogen, alkyl, alkenyl or alkynyl;

each $R^{11}$ is independently selected from hydrogen, alkyl, alkenyl, alkynyl;

each $R^{12}$ is independently selected from hydrogen, alkyl, alkenyl, or alkynyl;

each $R^{13}$ is independently selected from hydrogen, alkyl, alkenyl, or alkynyl;

each $R^{14}$ is selected from alkylene, alkenylene, or alkynylene; and $R^{15}$ is hydrogen, alkyl, alkenyl or alkynyl;

wherein t is 5 or less, for example 1, 2 or 3.

The modulator of formula (II) can be, for example, Caprylyl/Capryl Glucoside and is available under the tradename Plantacare® 810 UP from BASF, Ludwigshafen, Germany.

Without being limited by theory, it is believed that the alkoxylated glucoside acts as a modulator of the perceived intensity and/or longevity of the fragrance profile of the composition when low levels of the low volatile fragrance materials are used. For example, the modulators act to prolong the duration during which the fragrance profile can be perceived as compared to a control composition in the absence of the modulators. As another example, the modulators can improve the intensity of the fragrance profile such that it remains significantly the same from initial impression to the end as compared to a control composition.

While not wishing to be bound by theory, it is believed that the modulators associate to the fragrance materials and retard evaporation.

In another aspect, compositions can further comprise one or more non-odorous fragrance co-modulators. The fragrance co-modulators consist of substances capable of increasing the intensity and/or longevity of the fragrance profile, and therefore of the composition, as compared to control composition absent the co-modulators. For example, the non-odorous fragrance co-modulators are selected from the group consisting of:
(i) Isocetyl alcohol (CERAPHYL® ICA);
(ii) PPG-3 myristyl ether (like Tegosoft™ APM and/or Varonic® APM);
(iii) Neopentyl glycol diethylhexanoate (like Schercemol™ NGDO); and
(iv) a mixture thereof, like with isocetyl alcohol (CERAPHYL® ICA). PPG-3 myristyl ether is commercialized by various suppliers including:
(i) Evonik-Goldschmidt under the tradename Tegosoft™ APM;
(ii) Degussa under the tradename Varonic® APM;
(iii) International Specialty Products as a mixture of PPG-3 myristyl ether with isocetyl alcohol;
(iv) Lubrizol Advanced Materials (USA) as a mixture of PPG-3 myristyl ether with neopentyl glycol diethylhexanoate under the tradename Schercemol™ NGDO ester; and
(v) combinations thereof.

However, any such commercial forms of PPG-3 myristyl ether and mixtures thereof, are appropriate for use as co-modulators in the compositions.

The composition comprises non-odorous fragrance co-modulators in an amount of, for example, from about 0.05 wt % to about 10 wt %, from about 0.5 wt % to about 6 wt %, or combinations thereof, relative to the total weight of the composition. In additional examples, non-odorous fragrance co-modulators can be present in an amount of from about 0.05 wt %, or 0.5 wt %, to about 6 wt %, or 10 wt %, relative to the total weight of the composition. The non-odorous fragrance co-modulator can exist, for example, as mixtures of PPG-3 myristyl ether together with CERAPHYL® ICA and Schercemol™ NGDO ester, wherein the PPG-3 myristyl ether is 50 wt % and the other two components thereof are present in equal wt % in the mixture, wherein the wt % is the total weight of all the co-modulators in the composition. In one example, mixtures of PPG-3 myristyl ether with CERAPHYL® ICA, in a 1:1 weight ratio, can be used (PCT Publication No. WO2013/064412 (Firmenich)).

Co-modulators can also be mixtures of Neopentyl Glycol Diethylhexanoate together with CERAPHYL® ICA, wherein the Neopentyl Glycol Diethylhexanoate is 50 wt % and CERAPHYL® ICA is 50 wt %. Similarly, compositions can contain at least 50 wt % of Schercemol™ NGDO ester together with Tegosoft™ APM also proved to be useful to prolong the perception of the fragrance profile from the substrate on which it has been applied, as compared to control compositions (PCT Publication No. WO2013/060691 (Firmenich)).

The addition of the co-modulators is intended to further improve the intensity and/or longevity of the fragrance profile of the composition above the improvement already provided for by the modulators. In one example, at least 50 wt % of the non-odorous fragrance modulator is PPG-20 Methyl Glucose Ether, with the remainder to 100 wt % possibly being one or more other modulators or co-modulators.

In yet another aspect, compositions can comprise one or more non-odorous fragrance co-modulators selected from the group consisting of:
(v) Isocetyl alcohol (CERAPHYL® ICA);
(vi) PPG-3 myristyl ether (like Tegosoft™ APM and/or Varonic® APM);
(vii) Neopentyl glycol diethylhexanoate (like Schercemol™ NGDO); and
(viii) a mixture thereof, like with isocetyl alcohol (CERAPHYL® ICA);
and being essentially free of non-odorous modulators formed from an alkoxylated glucoside selected from the group consisting of methyl glucoside polyol, ethyl glucoside polyol and propyl glucoside polyol. As used herein, the term "essentially free" means that the composition is free of that ingredient or no ingredient is intended to be added to the composition.

In one example, a composition comprises:
(i) a fragrance component present in an amount of from about 0.04 wt % to about 30 wt %, 1 wt % to about 30 wt %, less than about 25 wt %, less than about 20 wt %, less than about 15 wt %, less than about 10 wt %, or less than 8 wt %, relative to the total weight of the composition; and wherein:
(a) the fragrance component comprises at least one low volatile fragrance material having a vapor pressure <0.001 Torr at 25° C.; and
(b) the low volatile fragrance material is present in an amount of from about 0.1 wt % to about 30 wt %, less than about 28 wt %, less than about 25 wt %, less than about 22 wt %, less than 20 wt %, less than 18 wt %, or less than 15 wt %, relative to the total weight of the fragrance component; and (ii) one or more non-odorous fragrance co-modulators selected from the group consisting of:
(a) Isocetyl alcohol;
(b) PPG-3 myristyl ether;
(c) Neopentyl glycol diethylhexanoate; and
(d) a mixture thereof;
wherein the co-modulators are present in an amount of from about 0.05 wt % or 0.5 wt % to about 6 wt % or 10 wt %, relative to the total weight of the composition

TEST METHODS

Test Method 1: Determining Vapor Pressure

In order to determine the vapor pressure for the fragrance materials, go to the website https://scifinder.cas.org/scifinder/view/scifinder/scifinderExplorejsf and follow these steps to acquire the vapor pressure.

1. Input the CAS registry number for the particular fragrance material.
2. Select the vapor pressure from the search results.
3. Record the vapor pressure (given in Torr at 25° C.).

SciFinder uses Advanced Chemistry Development (ACD/Labs) Software Version 11.02. (© 1994-2013). If the CAS number for the particular fragrance material is unknown or does not exist, you can utilize the ACD/Labs reference program to directly determine the vapor pressure.

Test Method 2: Olfactory Tests

In order to show the effect of the modulators/co-modulators and low volatile fragrance materials on the perception of fragrance profile in a composition, test compositions are made, as described in the Example section, and given to panelists to evaluate.

At the testing facility, 50 μL samples of the compositions or the controls are applied to glass slides and placed on a hot plate at 32° C. to represent skin temperature for varying durations. The panelists are asked to evaluate the perceived fragrance profile (intensity and/or character) from each pair of samples, i.e., that of the test composition vs. the corresponding control, at time 0 and later time points (1, 2, 3 4 and 6 hours post application) as the fragrance profile evolves. Their assessments are recorded. Panelists are selected from individuals who are either trained to evaluate fragrances according to the scales below or who have experience of fragrance evaluation in the industry.

(a) Fragrance Intensity:

The panelists are asked to give a score on a scale of 1 to 5 for perceived fragrance intensity according to the odour intensity scale set out in Table 3 herein below.

TABLE 3

Odour Intensity Scale

| Score | Fragrance Intensity |
|---|---|
| 1 | Very Poor |
| 2 | Poor |
| 3 | Good |
| 4 | Very Good |
| 5 | Excellent |

(b) Fragrance Character:

The panelists are asked to assess the fragrance character in one of 2 ways:
i) a score on a scale of 0 to 3 for the dominance of particular characters that are relevant to that particular fragrance, e.g.: floral, rose, muguet, fruity, apple, berry, citrus, woody, musk just to name a few, according to the odour grading scale set out in Table 4i herein below;
ii) a score on a scale of 1 to 5 for changes in the perceived fragrance character change for the test compositions versus the controls according to the odour grading scale set out in Table 4ii herein below.

TABLE 4i

Character Dominance Odour Grading Scale

| Score | Fragrance Character Dominance |
|---|---|
| 0 | Not noticeable |
| 1 | Slight presence of the character |
| 2 | Moderate presence of the character |
| 3 | Dominance of the character |

TABLE 4ii

Character Difference Odour Grading Scale

| Score | Fragrance Character Change |
|---|---|
| 1 | Perfume character is unchanged, i.e., no difference between the sample vs. the control. |
| 2 | Slight perfume character change when compared directly with the control. |
| 3 | Moderate perfume change but similar character to the control, |
| 4 | Large difference in perfume character from the control. |
| 5 | Total difference in the perfume character from the control. |

The results of the panelists are averaged and then analysed using Analysis of Variance methods. The model treats the subject as a random effect and looks at the impact of product, time and the interaction between product and time. From the analysis the least square means for the product and time interaction are obtained. These means (as well as their confidence intervals) are then plotted to enable comparisons between products at each time point. It should be noted that the confidence levels plotted are intended as a guide, and not as a statistical comparison, as they do not take into account that multiple testing has been performed. As well as a graphical assessment, statistical comparisons between the two products at each of the time points are performed with a Sidak correction for multiple comparisons. The p-values for the product differences were obtained, with p-values <0.05 indicating a statistical difference between the two products at 5% significance (or 95% confidence).

EXAMPLES

The following examples are provided for further illustration and are not to be construed as limiting, as many variations are possible without departing from its spirit or scope.

Examples 1 to 6

Fragrances

Examples 1a to 5 are non-limiting examples of formulations of fragrance materials intended to form a fragrance component of a composition. The exemplary formulations of the fragrance materials span the range from "simple accords" (<10 fragrance materials) to "complex fragrances" (>30 fragrance materials). Typically, full bodied fragrance compositions do not comprise less than about 30 fragrance materials. Examples 1b and 6 are examples of a comparative formulation of fragrance materials intended to form a fragrance component. The following fragrance formulations are made by mixing the listed ingredients in the listed proportions (wt %) at room temperature, wherein the wt % is relative to the total weight of the fragrance component.

TABLE 5

| Ingredients | CAS Number | Vapor Pressure (Torr at 25° C.) | Parts (wt %) |
|---|---|---|---|
| Example 1a - Fresh Floral Accord (Fragrance I - 8.00 wt % Low Volatile Fragrance Materials) | | | |
| Benzyl acetate | 140-11-4 | 0.1640 | 11.0 |
| Linalool | 78-70-6 | 0.0905 | 10.0 |
| Phenethyl alcohol | 60-12-8 | 0.0741 | 16.0 |
| Indole | 120-72-9 | 0.0298 | 1.0 |
| α-Terpineol | 98-55-5 | 0.0283 | 3.0 |
| Geranyl acetate | 105-87-3 | 0.0256 | 5.0 |
| Cymal | 103-95-7 | 0.00881 | 6.0 |
| Hydroxycitronellal | 107-75-5 | 0.00318 | 23.0 |
| Majantol | 103694-68-4 | 0.00224 | 17.0 |
| Hexyl cinnamic aldehyde | 101-86-0 | 0.000697 | 8.0 |
| Example 1b - Traditional Floral Accord (Fragrance VII - 54.00 wt % Low Volatile Fragrance Materials) | | | |
| Benzyl acetate | 140-11-4 | 0.1640 | 5.5 |
| Linalool | 78-70-6 | 0.0905 | 5.0 |
| Phenethyl alcohol | 60-12-8 | 0.0741 | 8.0 |
| Indole | 120-72-9 | 0.0298 | 0.5 |
| α-Terpineol | 98-55-5 | 0.0283 | 1.5 |
| Geranyl acetate | 105-87-3 | 0.0256 | 2.5 |
| Cymal | 103-95-7 | 0.00881 | 3.0 |
| Hydroxycitronellal | 107-75-5 | 0.00318 | 11.5 |
| Majantol | 103694-68-4 | 0.00224 | 8.5 |
| Hexyl cinnamic aldehyde | 101-86-0 | 0.000697 | 4.0 |
| iso gamma super | 68155-66-8 | 0.000565 | 12.50 |
| Sandalore | 65113-99-7 | 0.000625 | 18.75 |
| Habanolide | 111879-80-2 | 0.00000431 | 18.75 |

TABLE 6

| Ingredients | CAS Number | Vapor Pressure (Torr at 25° C.) | Parts (wt %) |
|---|---|---|---|
| Example 2 - Floral Gourmand Accord (Fragrance II - 0.20 wt % Low Volatile Fragrance Materials) | | | |
| Manzanate | 39255-32-8 | 2.910000 | 1.0 |
| Hexyl acetate | 142-92-7 | 1.390000 | 4.0 |
| Verdox™ | 88-41-5 | 0.103000 | 10.0 |
| Phenethyl alcohol | 60-12-8 | 0.074100 | 16.0 |
| Cymal | 103-95-7 | 0.008810 | 4.0 |
| Ethylmethylphenylglycidate | 77-83-8 | 0.005710 | 7.5 |
| Hydroxycitronellal | 107-75-5 | 0.003180 | 24.0 |
| Methyl Ionone | 7779-30-8 | 0.002860 | 22.5 |
| Gamma-Undecalactone (Ald C$^{14}$) | 104-67-6 | 0.002710 | 9.0 |
| Methyl laitone* | 94201-19-1 | 0.00872 | 0.2 |
| Triethyl citrate (TEC) | 77-93-0 | — | 1.8 |

*Supplied at 10% in TEC.

TABLE 7

| Ingredients | CAS Number | Vapor Pressure (Torr at 25° C.) | Parts (wt %) |
|---|---|---|---|
| Example 3 - Woody Accord (Fragrance III - 7.00 wt % Low Volatile Fragrance Materials) | | | |
| Vertenex | 32210-23-4 | 0.103000 | 7.0 |
| Koavone | 81786-73-4 | 0.027500 | 40.0 |
| Cedryl methyl ether | 19870-74-7 | 0.012800 | 5.0 |
| Synambran | 6790-58-5 | 0.009340 | 2.0 |
| Methyl Ionone | 7779-30-8 | 0.002860 | 6.0 |
| Kephalis | 36306-87-3 | 0.002690 | 20.0 |
| Cashmeran | 33704-61-9 | 0.002690 | 2.0 |
| Ambrocenide | 211299-54-6 | 0.001820 | 3.0 |
| Brahmanol | 72089-08-8 | 0.001540 | 8.0 |
| Sandalore ® | 65113-99-7 | 0.000625 | 7.0 |

TABLE 8

| Ingredients | CAS Number | Vapor Pressure (Torr at 25° C.) | Parts (wt %) |
|---|---|---|---|
| Example 4 - Fresh Male Accord (Fragrance IV - 13.51 wt % Low Volatile Fragrance Materials) | | | |
| d-Limonene | 5989-27-5 | 1.540000 | 10.0 |
| Dihydromyrcenol | 18479-58-8 | 0.166000 | 10.0 |
| Boisiris | 68845-00-1 | 0.013500 | 6.5 |
| Canthoxal | 5462-06-6 | 0.010200 | 8.0 |
| Helional | 1205-17-0 | 0.002700 | 10.0 |
| Kephalis | 36306-87-3 | 0.002690 | 20.0 |
| Majantol | 103694-68-4 | 0.002240 | 15.5 |
| Javanol ® | 198404-98-7 | 0.000902 | 5.0 |
| Galaxolide* | 1222-05-5 | 0.000414 | 7.5 |
| Isopropyl Myristate | 110-27-0 | — | 7.5 |

*Supplied at 50% in Isopropyl myristate.

TABLE 9

| Ingredients | CAS Number | Vapor Pressure (Torr at 25° C.) | Parts (wt %) |
|---|---|---|---|
| Example 5 - Sweet Dream 18 Fragrance (Fragrance V - 11.15 wt % Low Volatile Fragrance Materials) | | | |
| Prenyl acetate | 1191-16-8 | 3.99000000 | 0.100 |
| Manzanate | 39255-32-8 | 2.91000000 | 0.200 |
| Hexyl acetate | 142-92-7 | 1.39000000 | 0.700 |
| cis-3-Hexenyl acetate | 3681-71-8 | 1.22000000 | 0.200 |
| Benzaldehyde | 100-52-7 | 0.97400000 | 0.200 |
| Liffarome | 67633-96-9 | 0.72100000 | 0.150 |
| Hexyl isobutyrate | 2349-07-7 | 0.41300000 | 0.055 |
| Dihydromyrcenol | 18479-58-8 | 0.16600000 | 2.500 |
| Benzyl acetate | 140-11-4 | 0.16400000 | 0.700 |
| Linalyl acetate | 115-95-7 | 0.11600000 | 2.500 |
| Verdox | 88-41-5 | 0.10300000 | 4.000 |
| Phenethyl alcohol | 60-12-8 | 0.07410000 | 8.000 |
| Rossitol | 215231-33-7 | 0.02990000 | 1.500 |
| alpha-Terpineol | 98-55-5 | 0.02830000 | 1.500 |
| Geranyl acetate | 105-87-3 | 0.02560000 | 1.500 |
| Rhodinol | 141-25-3 | 0.01970000 | 0.700 |
| Givescone | 57934-97-1 | 0.01710000 | 0.700 |
| Methyl anthranilate | 134-20-3 | 0.01580000 | 0.050 |
| Ysamber K | 154171-77-4 | 0.01470000 | 1.000 |
| alpha-Ionone | 127-41-3 | 0.01440000 | 3.000 |
| Citronellyl acetate | 150-84-5 | 0.01370000 | 0.500 |
| cis-3-hexenyl-cis-3-hexenoate | 61444-38-0 | 0.01220000 | 0.200 |
| Cinnamic alcohol | 104-54-1 | 0.01170000 | 0.100 |
| delta-damascone | 57378-68-4 | 0.01020000 | 0.200 |
| Citronellyloxyacetaldehyde | 7492-67-3 | 0.00967000 | 0.100 |
| Cymal | 103-95-7 | 0.00881000 | 0.500 |
| Floralozone | 67634-15-5 | 0.00808000 | 0.100 |
| Ethylmethylphenylglycidate | 77-83-8 | 0.00571000 | 0.200 |
| Florosa Q | 63500-71-0 | 0.00557000 | 3.000 |
| Ethyl linalool | 10339-55-6 | 0.00520000 | 6.400 |

TABLE 9-continued

Example 5 - Sweet Dream 18 Fragrance (Fragrance V - 11.15 wt % Low Volatile Fragrance Materials)

| Ingredients | CAS Number | Vapor Pressure (Torr at 25° C.) | Parts (wt %) |
|---|---|---|---|
| Pivarose | 67662-96-8 | 0.00484000 | 2.500 |
| Hydroxycitronellal | 107-75-5 | 0.00318000 | 7.500 |
| Methyl Ionone | 7779-30-8 | 0.00286000 | 4.000 |
| gamma-Undecalactone | 104-67-6 | 0.00271000 | 0.500 |
| Kephalis | 36306-87-3 | 0.00269000 | 5.000 |
| Cashmeran | 33704-61-9 | 0.00269000 | 1.000 |
| Magnolan | 27606-09-3 | 0.00251000 | 3.000 |
| Majantol | 103694-68-4 | 0.00224000 | 6.900 |
| Brahmanol | 72089-08-8 | 0.00154000 | 3.000 |
| Coumarin | 91-64-5 | 0.00130000 | 0.500 |
| Glycolierral | 68901-32-6 | 0.00121000 | 0.100 |
| Raspberry ketone | 5471-51-2 | 0.00106000 | 0.100 |
| Top Mango base [3] | — | — | 0.500 |
| Cherry base [3] | — | — | 0.200 |
| Cassis base [3] | — | — | 0.300 |
| Bergamot Oil [4] | — | — | 6.000 |
| Prunella base [3] | — | — | 0.500 |
| Hexyl cinnamic aldehyde | 101-86-0 | 0.00069700 | 1.500 |
| Sandalore | 65113-99-7 | 0.00062500 | 3.000 |
| Dupical | 30168-23-1 | 0.00044100 | 0.005 |
| Galaxolide [1] | 1222-05-5 | 0.00041400 | 1.500 |
| Ebanol | 67801-20-1 | 0.00028100 | 2.000 |
| Helvetolide | 141773-73-1 | 0.00005790 | 2.000 |
| Warm Milk base [5] | — | — | 0.200 |
| Vanilla Absolute [2, 6] | — | — | 0.100 |
| Isopropyl Myristate | — | — | 1.500 |
| Dipropylene Glycol | — | — | 6.040 |
| Total | | | 100.00 |

[1] Supplied at 50% in IPM.
[2] Supplied at 50% in DiPG.
[3] Proprietary bases that contain a mixture of perfume raw materials, judged to be of high volatility for the purposes of calculating % of low volatility PRMs.
[4] Natural oils or extracts that contain a mixture of perfume raw materials, judged to be of high volatility for the purposes of calculating % of low volatility PRMs.
[5] Proprietary bases that contain a mixture of perfume raw materials, judged to be of low volatility for the purposes of calculating % of low volatility PRMs.
[6] Natural oils or extracts that contain a mixture of perfume raw materials, judged to be of low volatility for the purposes of calculating % of low volatility PRMs.

TABLE 10

Example 6 - Fresh Floral GF 6-7 Accord (Fragrance VI - 40.14 wt % Low Volatile Fragrance Materials)

| Ingredients | CAS Number | Vapor Pressure (Torr at 25° C.) | Parts (wt %) |
|---|---|---|---|
| Ligustral or Triplal | 68039-49-6 | 0.578000 | 0.15 |
| Benzyl acetate | 140-11-4 | 0.164000 | 0.31 |
| Verdox | 88-41-5 | 0.103000 | 5.38 |
| Phenethyl alcohol | 60-12-8 | 0.074100 | 1.54 |
| Indole | 120-72-9 | 0.029800 | 0.02 |
| Heliotropin | 120-57-0 | 0.010400 | 1.23 |
| gamma-Decalactone | 706-14-9 | 0.008520 | 0.38 |
| Florol | 63500-71-0 | 0.005570 | 15.38 |
| Ethyl linalool | 10339-55-6 | 0.005200 | 26.15 |
| Isoeugenol | 97-54-1 | 0.005190 | 0.08 |
| alpha-Irone | 79-69-6 | 0.004190 | 1.54 |
| Vanillin | 121-33-5 | 0.001940 | 6.15 |
| Dimethyl benzyl carbinyl butyrate | 10094-34-5 | 0.001680 | 1.54 |
| Methyl beta-naphthyl ketone | 93-08-3 | 0.000957 | 0.77 |
| Methyl dihydrojasmonate | 24851-98-7 | 0.000710 | 30.60 |
| Benzyl salicylate | 118-58-1 | 0.000175 | 7.69 |
| Polysantol | 107898-54-4 | 0.000117 | 0.77 |
| Lrg 201 | 4707-47-5 | 0.000029 | 0.31 |

Example 7

Compositions Comprising Fragrance Modulators

Compositions A, C, E, G, and L are examples of fine fragrance compositions, made with Fragrances I to V, respectively. They are prepared by admixture of the components described in Tables 11a, in the proportions indicated. In parallel, control Compositions B, D, F, H, and M, are prepared by replacing the non-odorous fragrance modulator, Glucam™ P-20, by the same amount of demineralized water. Additionally, Compositions I and N are examples of a fine fragrance composition comprising excessive levels of low volatile fragrance materials, and Compositions J and O are their corresponding controls, minus the non-odorous fragrance modulator, Glucam™ P-20. Composition K is an example of a fine fragrance composition with both modulator and co-modulator.

TABLE 11a

Fine Fragrance Compositions

| Ingredients | A | B | C | D | E | F | G | H | I | J | K | L | M | N | O |
|---|---|---|---|---|---|---|---|---|---|---|---|---|---|---|---|
| Fragrance I | 7.0 | 7.0 | — | — | — | — | — | — | — | — | 7.0 | — | — | — | — |
| Fragrance II | — | — | 7.0 | 7.0 | — | — | — | — | — | — | — | — | — | — | — |
| Fragrance III | — | — | — | — | 7.0 | 7.0 | — | — | — | — | — | — | — | — | — |
| Fragrance IV | — | — | — | — | — | — | 7.0 | 7.0 | — | — | — | — | — | — | — |
| Fragrance V | — | — | — | — | — | — | — | — | — | — | — | 7.0 | 7.0 | — | — |
| Fragrance VI | — | — | — | — | — | — | — | — | 8.45 | 8.45 | — | — | — | — | — |
| Fragrance VII | — | — | — | — | — | — | — | — | — | — | — | — | — | 8.0 | 8.0 |
| Ethanol | | | | | | | | 75.0 | | | | | | | |
| Glucam ™ P-20 | 15.0 | — | 15.0 | — | 15.0 | — | 15.0 | — | 15.0 | — | 7.5 | 15.0 | — | 15.0 | — |
| Isocetyl alcohol CERAPHYLICA | — | — | — | — | — | — | — | — | — | — | 7.5 | — | — | — | — |
| Demineralized water | | | | | | | | to 100 | | | | | | | |

[1] Wt % is relative to the total weight of the composition.

Compositions AA, BB, CC, DD, EE, FF, HH, II, and JJ are examples of fine fragrance compositions, made with Fragrances I, II and V the non-odorous fragrance modulators: Glucam™ P-10, Glucam™ E-10, and Glucam™ E-20, respectively. They are prepared by admixture of the components in Table 11b, in the proportions indicated. In parallel, Compositions GG and KK, are prepared by incorporating a non-odorous fragrance modulator and a co-modulator (Glucam™ P-10 and Isocetyl alcohol CERAPHYL ICA) or two non-odorous fragrance modulators (Glucam™ P-10, Glucam™ P-20), respectively.

TABLE 11b

Fine Fragrance Compositions

Composition (wt %)[1]

| Ingredients | AA | BB | CC | DD | EE | FF | GG | HH | II | JJ | KK |
|---|---|---|---|---|---|---|---|---|---|---|---|
| Fragrance I | 7.0 | 7.0 | 7.0 | — | — | — | 7.0 | — | — | — | 7.0 |
| Fragrance II | — | — | — | 7.0 | 7.0 | 7.0 | — | — | — | — | — |
| Fragrance V | — | — | — | — | — | — | — | 7.0 | 7.0 | 7.0 | — |
| Ethanol | | | | | 75.0 | | | | | | |
| Glucam™ P-20 | — | — | — | — | — | — | — | — | — | — | 7.5 |
| Glucam™ P-10 | 15 | — | — | 15 | — | — | 7.5 | 15 | — | — | 7.5 |
| Glucam™ E-10 | — | 15 | — | — | 15 | — | — | — | 15 | — | — |
| Glucam™ E-20 | — | — | 15 | — | — | 15 | — | — | — | 15 | — |
| Isocetyl alcohol CERAPHYL ICA | — | — | — | — | — | — | 7.5 | — | — | — | — |
| Demineralized water | | | | | to 100 | | | | | | |

[1] Wt % is relative to the total weight of the composition.

Compositions b and d are examples of compositions made with single perfume raw materials and the non-odorous modulators Simulsol SL 11W™ and Plantacare® 810 UP, respectively. They are prepared by admixture of the components in Table 11c, in the proportions indicated. In parallel, control Compositions a and c are prepared without a non-odorous modulator as a control.

TABLE 11c

Single Perfume Raw Material Compositions

Composition (wt %)[1]

| Ingredients | a | b | c | d |
|---|---|---|---|---|
| Phenethyl alcohol | 1.0 | 1.0 | — | — |
| Cymal | — | — | 1.0 | 1.0 |
| Simulsol SL11W™[2] | — | 2.7 | — | — |
| Plantacare® 810 UP[3] | — | — | — | 2.5 |
| Ethanol | | | 75 | |
| Demineralized water | | to 100 | | |

[1] Wt % is relative to the total weight of the composition.
[2] Added as a 55 wt % active solution in water.
[3] Added as a 62 wt % active solution in water.

Compositions P and Q are examples of body spray compositions. They are prepared by admixture of the components described in Table 12, in the proportions indicated.

TABLE 12

Body Spray Compositions

Compositions (wt %)[1]

| Ingredients | CAS Number | P | Q | PP | QQ |
|---|---|---|---|---|---|
| Denatured Ethanol | 64-17-5 | 39.70 | 59.45 | 39.70 | 39.70 |
| Water | 7732-18-5 | — | 0.75 | — | — |
| Dipropylene Glycol | 25265-71-8 | 15.00 | — | 15.00 | 15.00 |
| Isopropyl Myristate | 110-27-0 | 1.00 | — | 1.00 | 1.00 |

TABLE 12-continued

Body Spray Compositions

Compositions (wt %)[1]

| Ingredients | CAS Number | P | Q | PP | QQ |
|---|---|---|---|---|---|
| Zinc Phenosulphonate | 127-82-2 | 0.50 | — | 0.50 | 0.50 |
| Cavasol® W7 methylated Beta-cyclodextrin | 128446-36-6 | — | 1.00 | — | — |
| Fragrance[2] | — | 1.20 | 1.20 | 1.20 | 1.20 |
| Glucam™ P-20 | 61849-72-7 | 2.60 | 2.60 | — | — |
| Glucam™ P-10 | 61849-72-7 | — | — | 2.60 | — |
| Glucam™ E-20 | 68239-42-9 | — | — | — | 2.60 |
| Propane | 74-98-6 | 4.86 | — | 4.86 | 4.86 |
| Isobutane | 72-28-5 | 27.14 | — | 27.14 | 27.14 |
| 1,1-Difluoroethane (HFC-152a) | 75-37-6 | 8.00 | 35.00 | 8.00 | 8.00 |

[1] wt % relative to the total weight of the composition.
[2] Can be any Fragrances I, II, or V.

Composition R is an example of body lotion composition. It is prepared by admixture of the components described in Table 13, in the proportions indicated.

TABLE 13

Body Lotion Composition

Compositions (wt %)[1]

| Ingredients | CAS Number | R | S | T |
|---|---|---|---|---|
| Water | 7732-18-5 | qsp 100% | qsp 100% | qsp 100% |
| Trilon® B | 64-02-8 | 0.05 | 0.05 | 0.05 |

TABLE 13-continued

Body Lotion Composition

| Ingredients | CAS Number | Compositions (wt % [1]) | | |
|---|---|---|---|---|
| | | R | S | T |
| Carbopol ® ETD 2050 | 9003-01-4 | 0.2 | 0.2 | 0.2 |
| Pemulen ™ TR1 | 9063-87-0 | 0.2 | 0.2 | 0.2 |
| Nexbase ® 2008 | 68037-01-4 | 8 | 8 | 8 |
| Silicone V100 | 63148-62-9 | 6 | 6 | 6 |
| Glucam ™ P-20 | 61849-72-7 | 3 | — | — |
| Glucam ™ P-10 | 61849-72-7 | — | 3 | — |
| Glucam ™ E-20 | 68239-42-9 | — | — | 3 |
| Tris Amino ™ Ultra Pur | 102-71-6 | 0.4 | 0.4 | 0.4 |
| Fragrance [2] | — | 3 | 3 | 3 |
| Preservatives | — | qs | qs | qs |

[1] wt % relative to the total weight of the composition.
[2] Can be any Fragrances I, II, or V.

Example 8

Odour Test

Compositions disclosed in Table 11a are applied to glass slides in accordance with the protocol described in the Method Section and a panel of 9 expert panelists evaluated the perceived fragrance profile at initial time 0, then at various time points typically 1 hour, 2 hours, 3 hours, 4 hours and 6 hours post application.

(a) Compositions A vs. B:

Panellists are asked to score the compositions for the intensity of the fragrance on a scale of 1 to 5, wherein 1 represents a low fragrance intensity is detected and 5 represents a very strong fragrance intensity is detected. The results of the panel test are then averaged. FIG. 1 shows the effect of the fragrance modulator and reduced levels of low volatile fragrance materials for compositions A and B on fragrance intensity. Fragrance intensity is maintained for up to 6 hours in the presence of the modulator whilst it drops in the absence of the modulator. The modulator acts to maintain the continued evaporation over time of the perfume materials. The effect of the improved fragrance strength can be noticeable at 3 hours and 6 hours with an indication of a statistical difference at 6 hours after application on the slides as indicated graphically by the confidence intervals. Statistical analysis using the Sidak corrections for multiple comparisons confirm the statistically significant difference between the 2 products at 6 hours at 5% significance level ($p=0.0008$, i.e., $p<0.05$).

Figure 2:
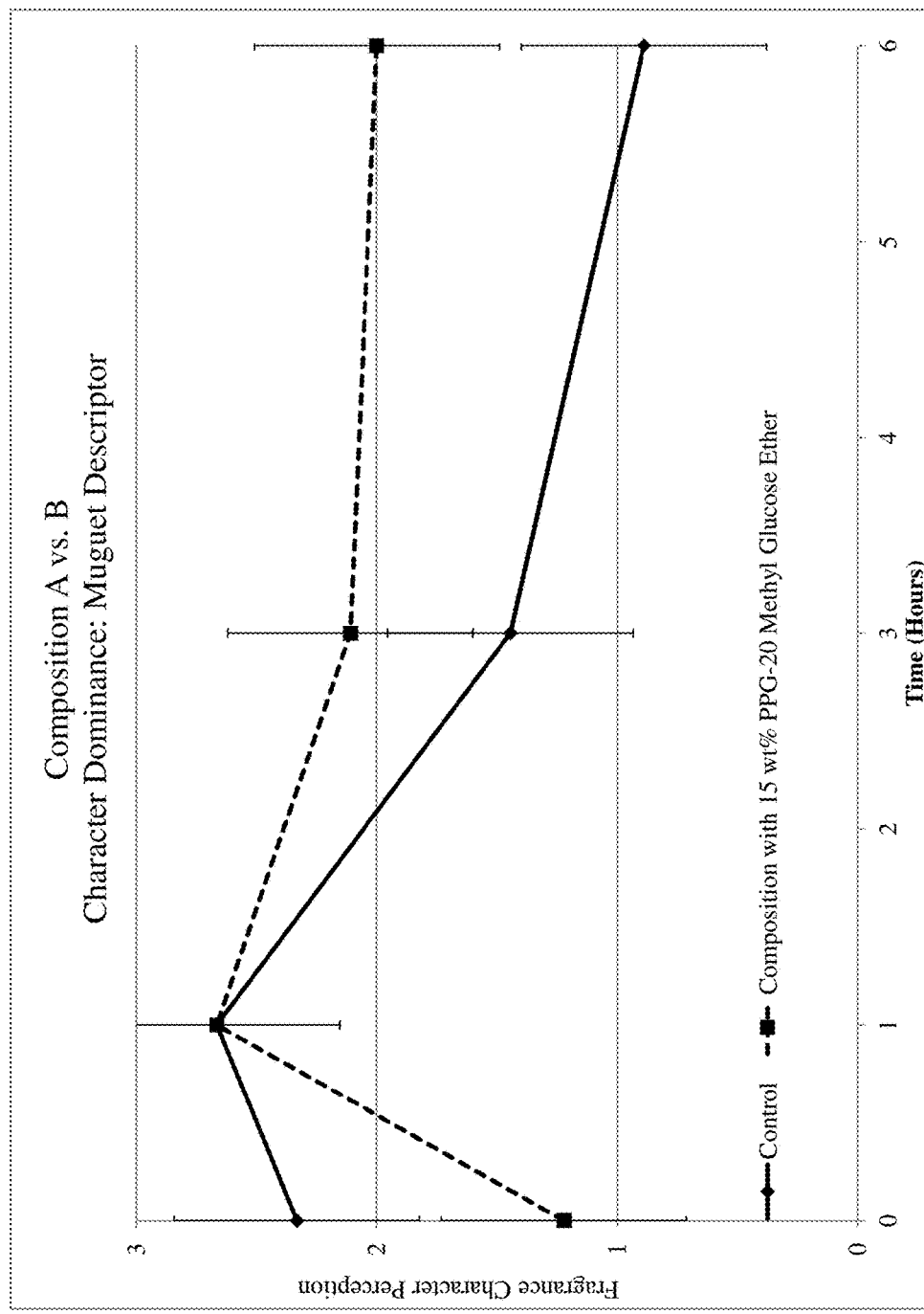
FIG. 2 provides the panel test results of perceived fragrance profile, particularly fragrance character dominance, of exemplary "Composition A" comprising 8.00 wt % of low volatile fragrance materials as compared to "Composition B", a control absent of a fragrance modulator (PPG-20 Methyl Glucose Ether), and as a function of time elapsed since application of the composition.

Panellists are also asked to score the composition for the dominance of the muguet character on a scale of 0 to 3 wherein 0 represents not detectable and 3 represents it being the dominant character. The results of the panel test are then averaged. FIG. 2 shows the effect of the fragrance modulator and reduced levels of low volatile fragrance materials for compositions A and B on muguet character dominance. The muguet character is reduced by the modulator at the initial time point but is then released over the remainder of the time for up to at least 6 hours. The effect of the improved fragrance character over time of the compositions are noticeable at 3 and 6 hours with an indication of a statistical difference at 6 hours after application on the slides as indicated by the confidence intervals. Statistical analysis using both the Sidak corrections for multiple comparisons confirm the statistically significant difference between the 2 products at 0 and 6 hours at 5% significance level ($p=0.0261$ respectively, i.e., $p<0.05$).

Figure 3:
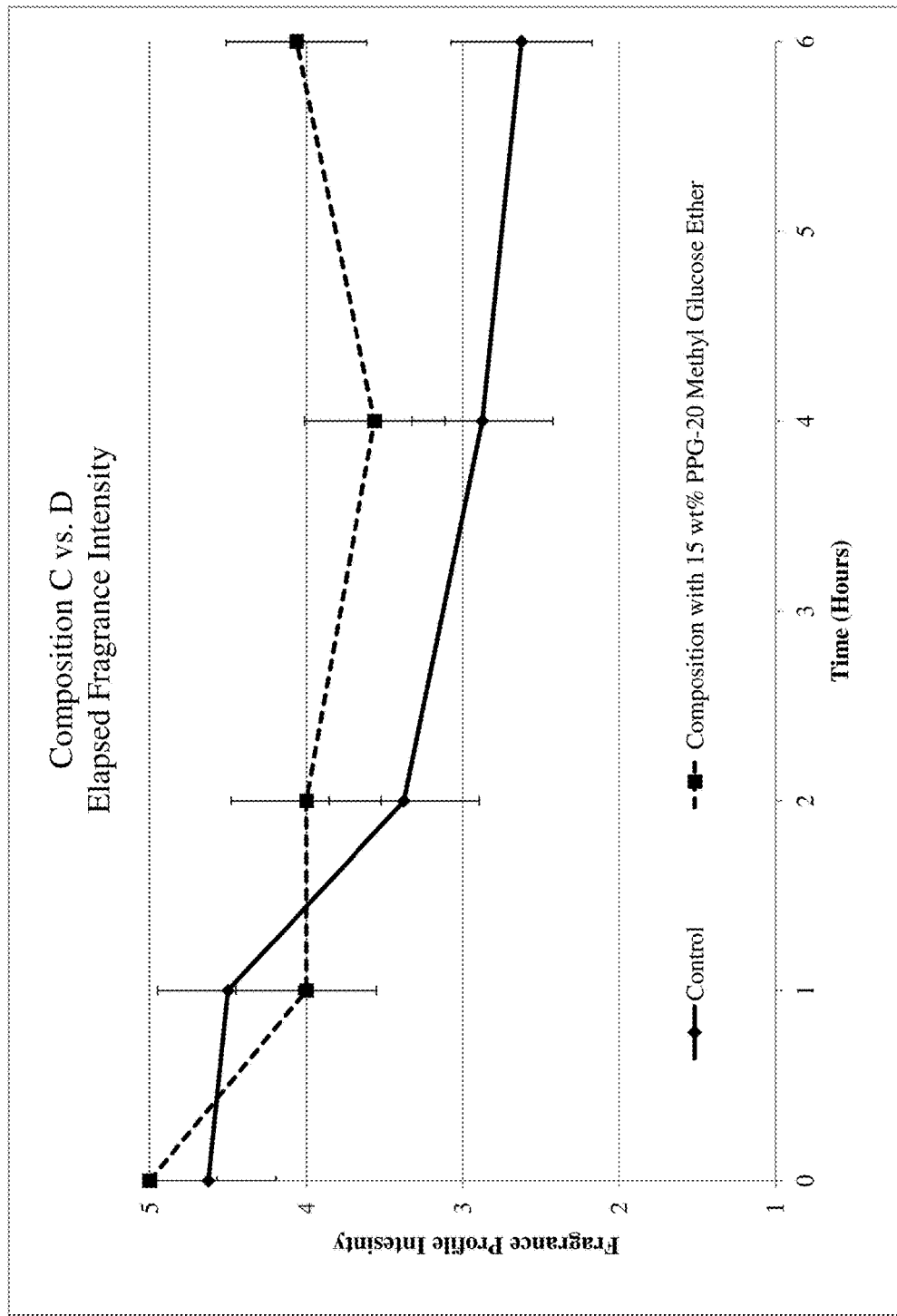
FIG. 3 provides the panel test results of perceived fragrance profile, particularly fragrance intensity, of exemplary "Composition C" comprising 0.20 wt % of low volatile fragrance materials as compared to "Composition D", a control absent of a fragrance modulator (PPG-20 Methyl Glucose Ether), and as a function of time elapsed since application of the composition.

(b) Compositions C vs. D:

Panellists are asked to score the compositions for the intensity of the fragrance on a scale of 1 to 5, wherein 1 represents a low fragrance intensity is detected and 5 represents a very strong fragrance intensity is detected. The results of the panel test are then averaged. FIG. 3 shows the effect of the fragrance modulator and reduced levels of low volatile fragrance materials for compositions C and D on fragrance intensity. Fragrance intensity is maintained for up to 6 hours in the presence of the modulator whilst it drops in the absence of the modulator. The modulator acts to maintain the continued evaporation over time of the perfume materials. The effect of the improved fragrance strength is noticeable at 2 and 4 hours and significant at 6 hours after application on the slides as indicated graphically by the confidence intervals. Statistical analysis using the Sidak corrections for multiple comparisons confirm the statistically significant difference between the 2 products at 4 hours at 5% significance level ($p=0.035$, i.e., $p<0.05$) and at 6 hours at 5% significance level ($p=<0.0001$, i.e., $p<0.05$).

Figure 4:
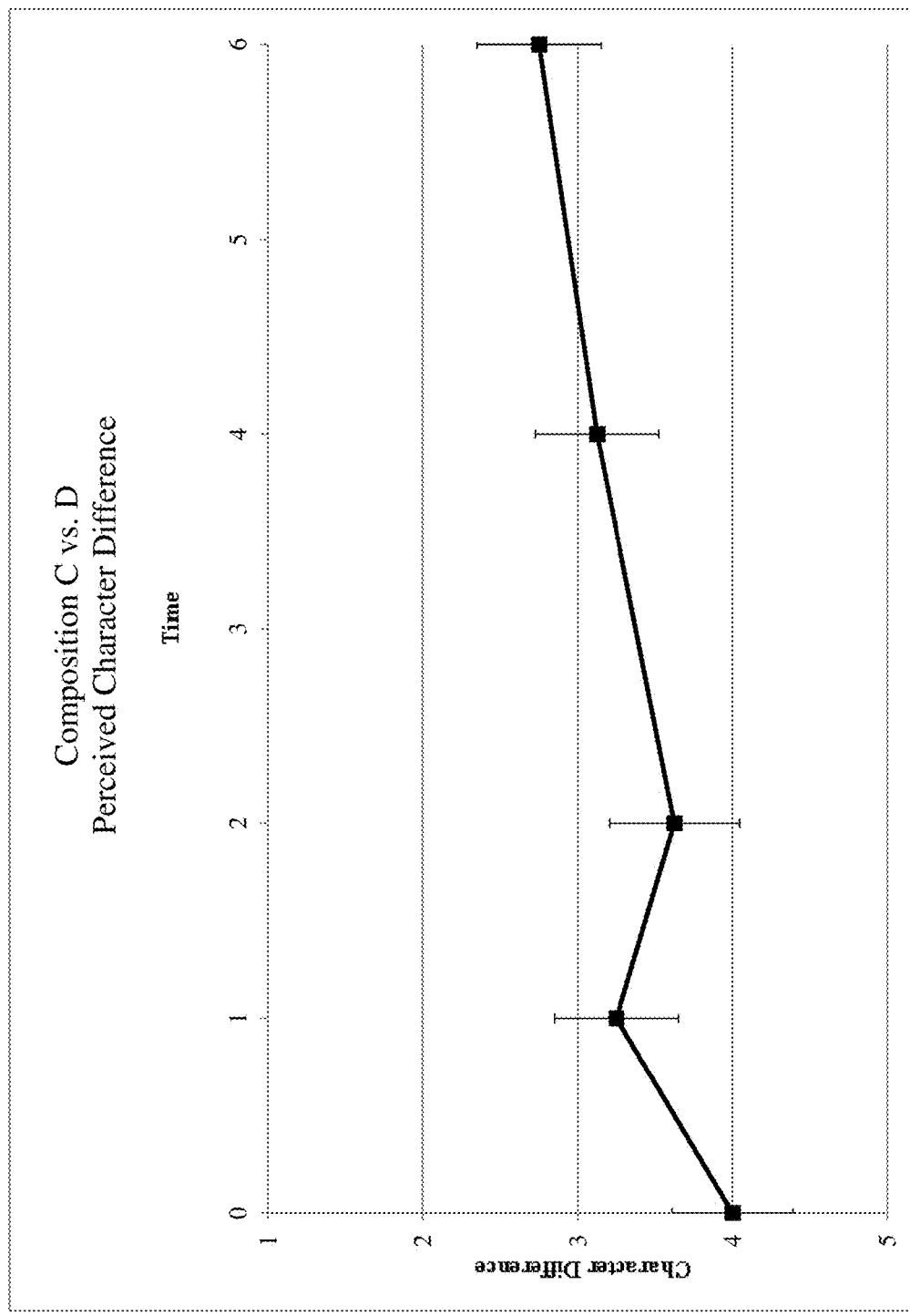
FIG. 4 provides the panel test results of perceived differences in the fragrance profile, particularly differences in the fragrance character, of exemplary "Composition C" comprising 0.20 wt % of low volatile fragrance materials as compared to "Composition D", a control absent of a fragrance modulator (PPG-20 Methyl Glucose Ether), and as a function of time elapsed since application of the composition.

Panellists are asked to score the compositions on a scale of 1 to 5, wherein 1 represents the perfume character remains unchanged and 5 represents a total change in the perfume character. The results of the panel test were averaged and plotted together with the confidence intervals. FIG. 4 shows the effect of the fragrance modulator and reduced levels of low volatile fragrance materials for compositions C and D. The presence of the modulator results in noticeable changes in perfume character. Statistical analysis using the Sidak corrections for multiple comparisons confirm the statistically significant difference between the 2 products at 1 hour ($p=0.002$, i.e., $p<0.05$), 4 hours ($p=0.0003$, i.e., $p<0.05$) and 6 hours ($p=<0.001$, i.e., $p<0.05$) at 5% significance level.

Similar effects are observed for compositions E to H, and L to M (data not shown).

(c) Compositions N and O

Figure 5:
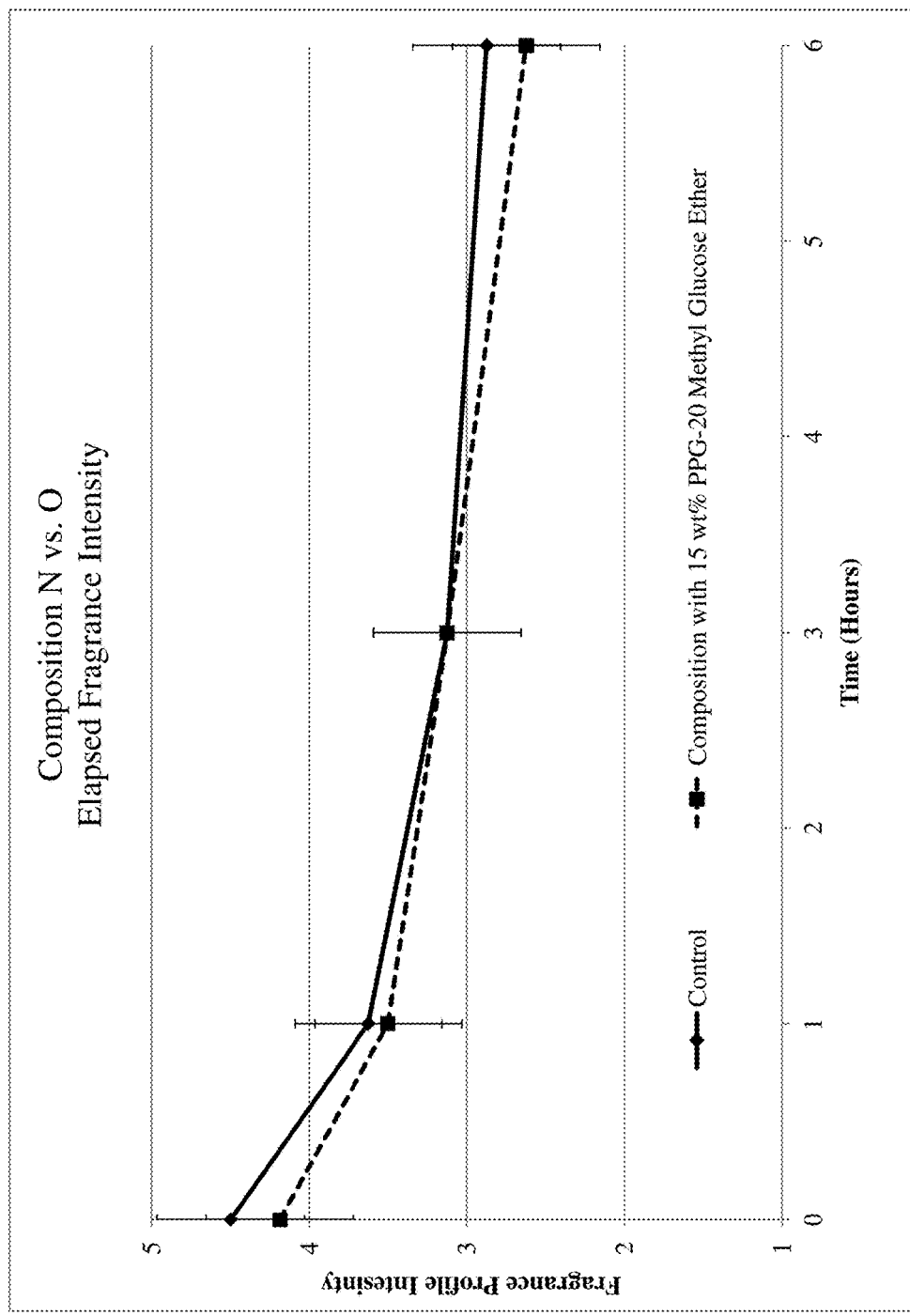
FIG. 5 provides the panel test results of perceived fragrance profile, particularly fragrance intensity, of exemplary "Composition N" comprising 54 wt % of low volatile fragrance materials as compared to "Composition O", a control absent of a fragrance modulator (PPG-20 Methyl Glucose Ether), and as a function of time elapsed since application of the composition.

Panellists are asked to score the compositions for the intensity of the fragrance on a scale of 1 to 5, wherein 1 represents a low fragrance intensity is detected and 5 represents a very strong fragrance intensity is detected. The results of the panel test are then averaged. FIG. 5 shows the effect of the fragrance modulator and excessive levels of low volatile fragrance materials for compositions N and O on fragrance intensity. Fragrance intensity is unaffected by the addition of the modulator. There are no statistical differences between the 2 products.

Figure 6:
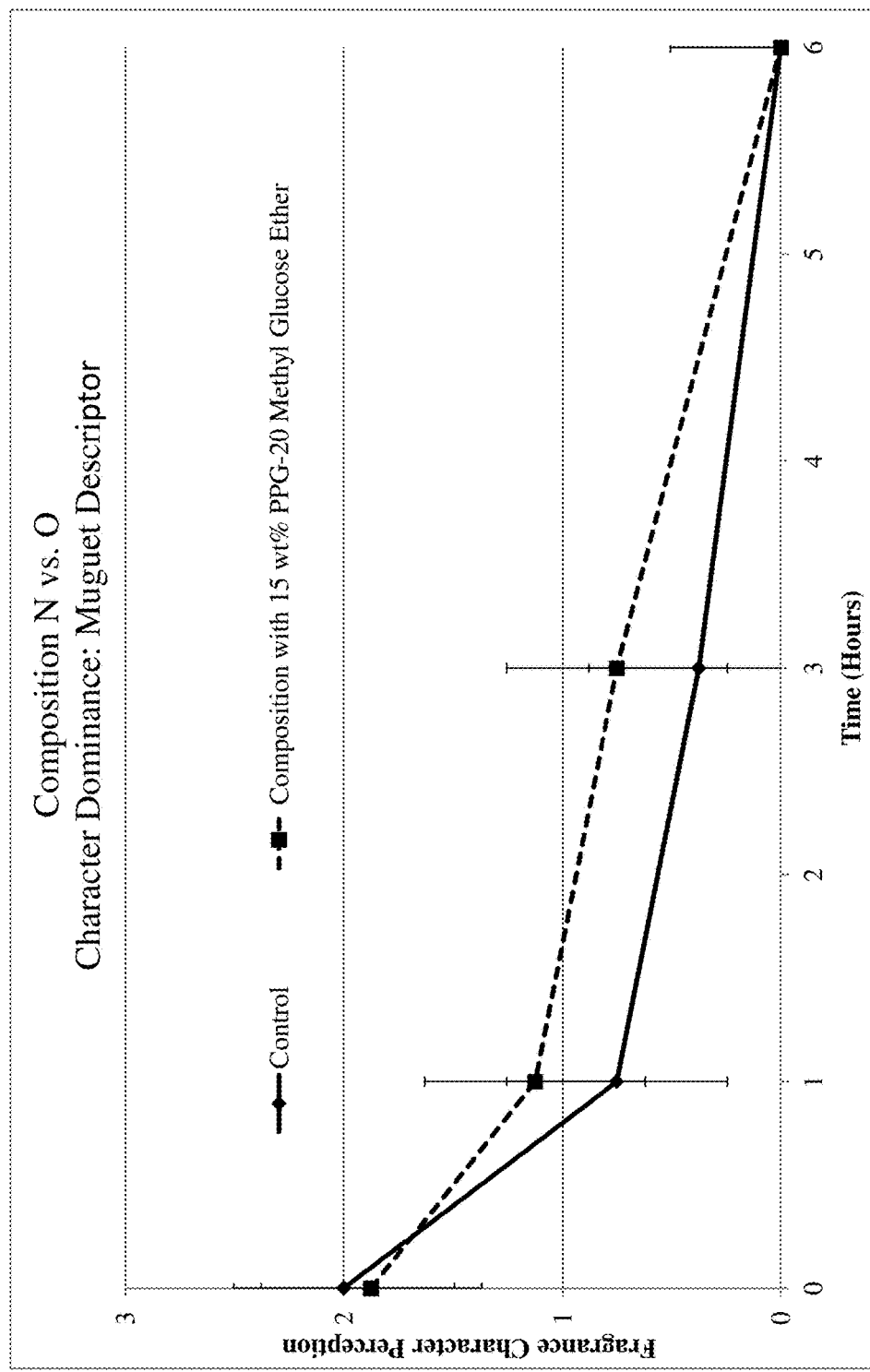
FIG. 6 provides the panel test results of perceived fragrance profile, particularly fragrance character dominance, of exemplary "Composition N" comprising 54 wt % of low volatile fragrance materials as compared to "Composition O", a control absent of a fragrance modulator (PPG-20 Methyl Glucose Ether), and as a function of time elapsed since application of the composition.

Panellists are also asked to score the composition for the dominance of the muguet character on a scale of 0 to 3 wherein 0 represents not detectable and 3 represents it being the dominant character. The results of the panel test are then averaged. FIG. 6 shows the effect of the fragrance modulator and excessive levels of low volatile fragrance materials for compositions N and O on muguet character dominance. The muguet character is perceived initially but then drops quickly over time. After 1 hour it is only slightly perceived and after 6 hours it is not present in either composition. Addition of the modulator does not result in prolonged release of the muguet character as was seen in compositions A and B. There are no statistical differences between the 2 products.

(d) Compositions I and J

Figure 7:
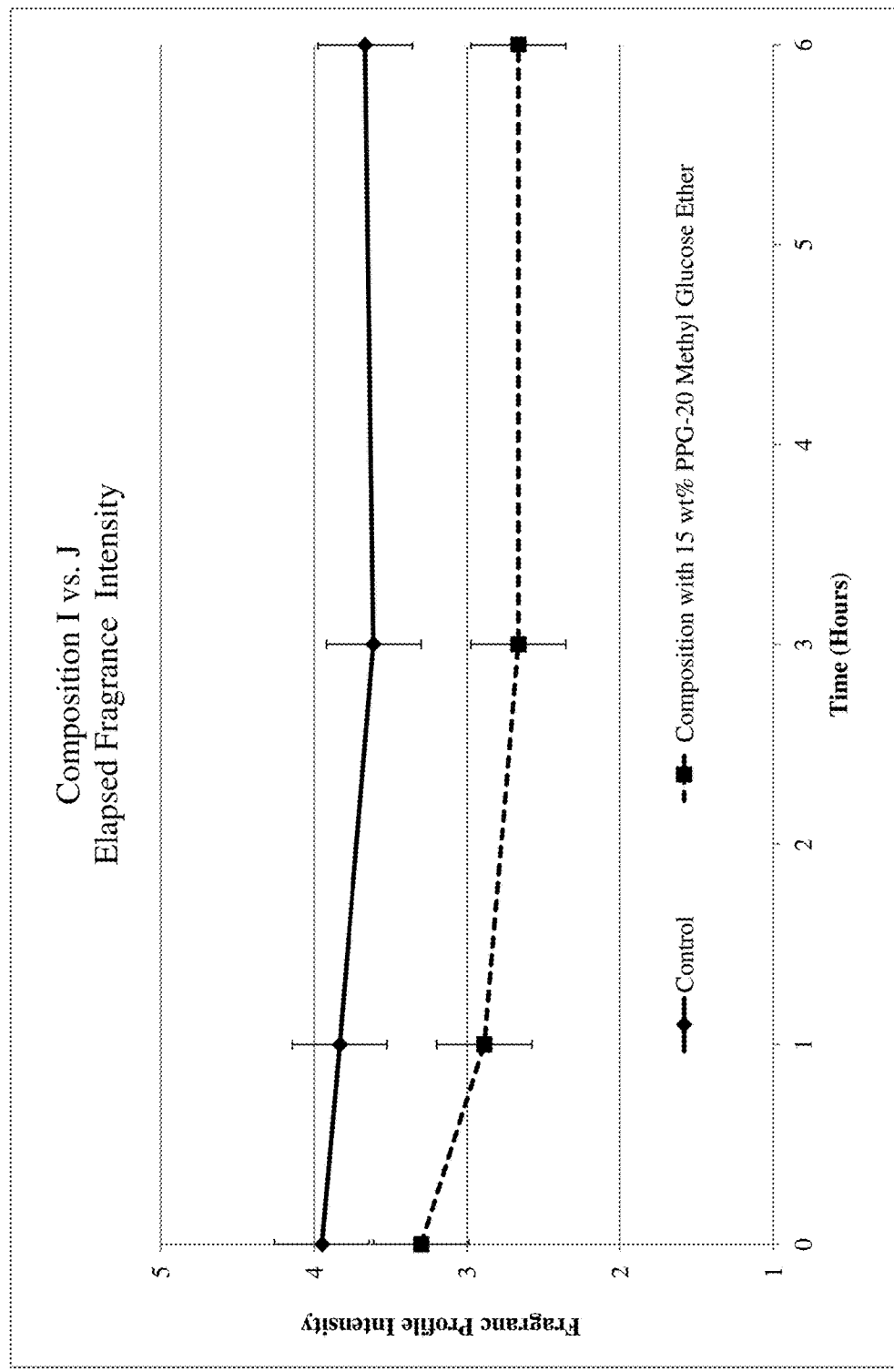
FIG. 7 provides the panel test results of perceived fragrance profile, particularly fragrance intensity, of "Composition I" wherein the fragrance component comprises 40.14 wt % of low volatile fragrance materials as compared to "Composition J", a control absent of a fragrance modulator (PPG-20 Methyl Glucose Ether), and as a function of time elapsed since application of the composition.

Panellists are asked to score the compositions for the intensity of the fragrance on a scale of 1 to 5, wherein 1 represents a low fragrance intensity is detected and 5 represents a very strong fragrance intensity is detected. The results of the panel test are then averaged. FIG. 7 shows the effect of the fragrance modulator in the presence of excessive levels of low volatile fragrance materials for compositions I and J. The effects of the modulator is negated in more traditional fragrance composition where excessive amounts of the low volatile fragrance materials are present. The fragrance appears to be suppressed with a loss of strength. This is noticeable at all time points and appears significant as indicated graphically by the confidence intervals. Statistical analysis using the Sidak corrections for multiple comparisons confirm the statistically significant difference between the 2 products at time 0 (p=0.0229, i.e., p<0.05), at 1 hour (p=0.0013, i.e., p<0.05), at 3 hours (p=0.0013, i.e., p<0.05) and at 6 hours (p=0.0003, i.e., p<0.05) at 5% significance level.

Compositions disclosed in Table 11c are applied to glass slides in accordance with the protocol described in the Method Section and a panel of 8 expert panelists evaluated the perceived fragrance profile at initial time 0, then at various time points typically 1 hour, 3 hours, 5 hours and 6 hours post application.

Figure 8:
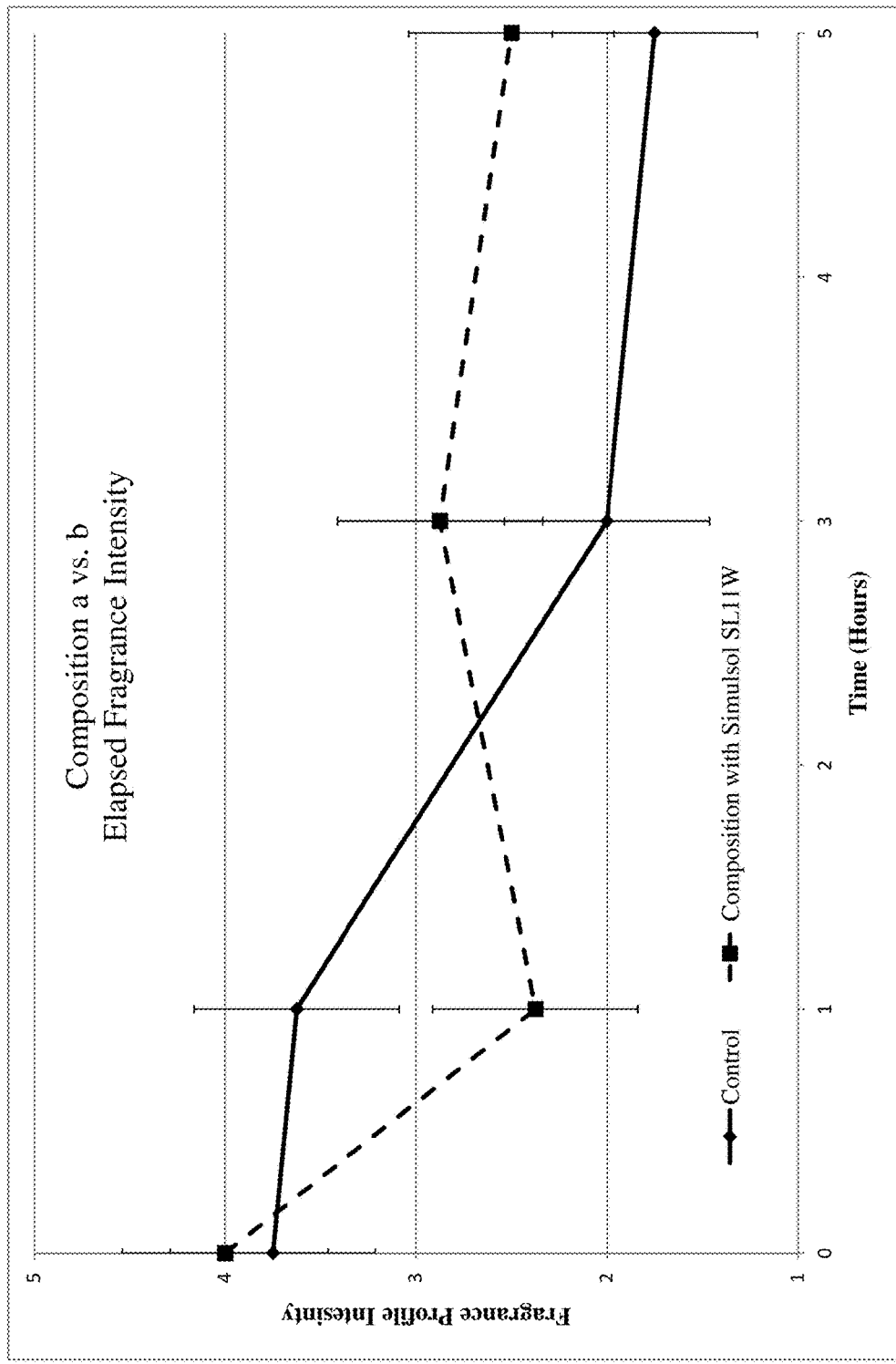
FIG. 8 provides the panel test results of perceived fragrance profile, particularly fragrance intensity, of "Composition b" wherein the fragrance component comprises 1.0 wt % of low volatile fragrance material as compared to "Composition a", a control composition absent of a fragrance modulator (Simulsol SL11W™), and as a function of time elapsed since application of the composition.

(e) Compositions a vs. b:

Panellists are asked to score the compositions for the intensity of the fragrance on a scale of 1 to 5, wherein 1 represents a low fragrance intensity is detected and 5 represents a very strong fragrance intensity is detected. The results of the panel test are then averaged. FIG. 8 shows the effect of the non-odorous fragrance modulator Simulsol SL11W™ on phenethyl alcohol. Addition of the non-odorous fragrance modulator maintains the intensity of the perfume raw material from 1 hour up to 5 hours whilst the control compositions, in the absence of the non-odorous fragrance modulator, drops in intensity over the 5 hours. The non-odourous fragrance modulator acts to maintain the continued evaporation over time of the perfume material. Statistical analysis using the Tukey correction for multiple comparisons confirm the statistically significant difference at 1 hour at 90% significance level (p=0.0933, i.e., p<0.10).

Figure 9:
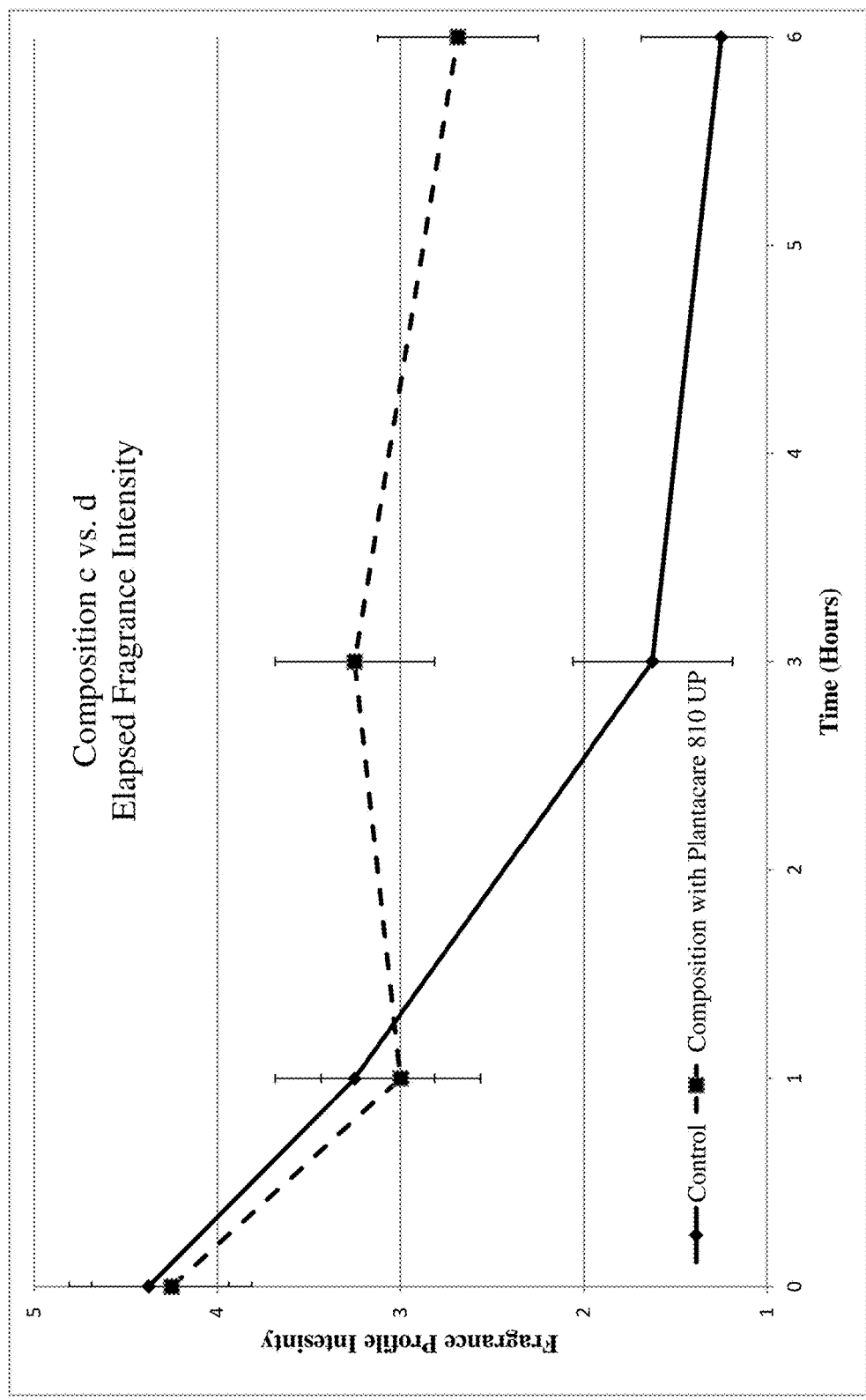
FIG. 9 provides the panel test results of perceived fragrance profile, particularly fragrance intensity, of "Composition d" wherein the fragrance component comprises 1.0 wt % of low volatile fragrance material as compared to "Composition c", a control composition absent of a fragrance modulator (Plantacare® 810 UP), and as a function of time elapsed since application of the composition.

(f) Compositions c vs. d:

Panellists are asked to score the compositions for the intensity of the fragrance on a scale of 1 to 5, wherein 1 represents a low fragrance intensity is detected and 5 represents a very strong fragrance intensity is detected. The results of the panel test are then averaged. FIG. 9 shows the effect of the fragrance modulator Plantacare® 810UP on Cymal. Addition of the modulator maintains the intensity of the perfume raw material from 1 hour up to 6 hours whilst the control, in the absence of the modulator, drops over the 6 hours. The modulator acts to maintain the continued evaporation over time of the perfume material. Statistical analysis using the Tukey correction for multiple comparisons confirms the statistically significant difference at 3 hours at 95% significance level (p=0.0002, i.e., p<0.05) and at 6 hours at 95% significance level (p 0.0022, i.e., p<0.05).

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
   (i) a fragrance component in an amount of about 0.04 wt % to about 30 wt %, relative to the total weight of the composition; and wherein:
      (a) the fragrance component comprises at least one low volatile fragrance material having a vapor pressure less than 0.001 Torr at 25° C.;
      (b) the low volatile fragrance material is present in an amount of about 0.1 wt % to about 30 wt %, relative to the total weight of the fragrance component; and
      (c) the fragrance component further comprising one or more volatile fragrance materials having a vapor pressure greater than or equal to 0.001 Torr at 25° C. and present in the amount of from about 70 wt % to about 99.9 wt %, by weight of the fragrance component; and
   (ii) at least one non-odorous alkoxylated glucoside fragrance modulator in an amount of from about 0.1 wt % to about 20 wt %, relative to the total weight of the composition.

2. The composition of claim 1, wherein the non-odorous fragrance modulator is selected from the group consisting of methyl glucoside polyol, ethyl glucoside polyol, propyl glucoside polyol, and combinations thereof.

3. The composition of claim 1, wherein the non-odorous fragrance modulator is selected from the group consisting of:
i) a compound of formula (I):

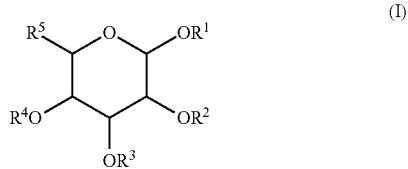

wherein:
$R^1$ is hydrogen, alkyl, alkenyl or alkynyl;
$R^2$ is selected from hydrogen, alkyl, alkenyl, alkynyl, $-[R^6R^7(R^8)O]_wR^9$, wherein w is from 1 to 10;
$R^3$ is selected from hydrogen, alkyl, alkenyl, alkynyl, $-[R^6R^7(R^8)O]_yR^9$, wherein y is from 1 to 10;
$R^4$ is selected from hydrogen, alkyl, alkenyl, alkynyl, $-[R^6R^7(R^8)O]_xR^9$, wherein x is from 1 to 10;
$R^5$ is selected from hydrogen, alkyl, alkenyl, alkynyl, $-R^6OR^9$, $-R^6O[R^6R^7(R^8)O]_zR^9$, wherein z is from 1 to 10;
each $R^6$ and $R^7$ are independently selected from alkylene, alkenylene, or alkynylene; and
each $R^8$ and $R^9$ is independently selected from hydrogen or alkyl,
(ii) a compound of formula (II):

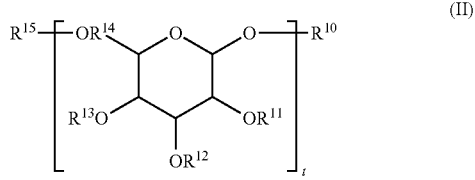

wherein:
$R^{10}$ is hydrogen, alkyl, alkenyl or alkynyl;
each $R^{11}$ is independently selected from hydrogen, alkyl, alkenyl, alkynyl;
each $R^{12}$ is independently selected from hydrogen, alkyl, alkenyl, or alkynyl;
each $R^{13}$ is independently selected from hydrogen, alkyl, alkenyl, or alkynyl;
each $R^{14}$ is selected from alkylene, alkenylene, or alkynylene; and
$R^{15}$ is hydrogen, alkyl, alkenyl or alkynyl;
wherein t is 5 or less; and
iii) combinations thereof.

4. The composition of claim 1, wherein the low volatile fragrance material is selected from the group consisting of: Cyclopentaneacetic acid, 3-oxo-2-(2Z)-2-penten-1-yl-, methyl ester, (1R,2R)—; 2-Buten-1-ol, 2-methyl-4-(2,2,3-trimethyl-3-cyclopenten-1-yl)-; Ethanone, 1-(2-naphthalenyl)-; 3-Decanone, 1-hydroxy-; Cyclopropanemethanol, 1-methyl-2-[(1,2,2-trimethylbicyclo[3.1.0]hex-3-yl)methyl]-; Benzaldehyde, 3-ethoxy-4-hydroxy-; 2H-1,5-Benzodioxepin-3(4H)-one, 7-methyl-; 2-Butanol, 1-[[2-(1,1-dimethylethyl)cyclohexyl]oxy]-; Spiro[5.5]undec-8-en-1-one, 2,2,7,9-tetramethyl-; Cyclopentaneacetic acid, 3-oxo-2-pentyl-, methyl ester, (1R,2R)-rel-; Cyclopentaneacetic acid, 3-oxo-2-pentyl-, methyl ester; Octanal, 2-(phenylmethylene)-; Cyclopentanecarboxylic acid, 2-hexyl-3-oxo-, methyl ester; 3-Cyclopentene-1-butanol, α,β,2,2,3-pentamethyl-; Cyclopentanone, 2-(3,7-dimethyl-2,6-octadien-1-yl)-; 1,6,10-Dodecatrien-3-ol, 3,7,11-trimethyl-; 2-Pentenenitrile, 3-methyl-5-phenyl-, (2Z)-; Benzenepropanenitrile, 4-ethyl-α,α-dimethyl-; 1H-3a,7-Methanoazulen-6-ol, octahydro-3,6,8,8-tetramethyl-, (3R,3aS,6R,7R,8aS)-; Ethanone, 1-(1,2,3,4,5,6,7,8-octahydro-2,3,8,8-tetramethyl-2-naphthalenyl)-; Propanoic acid, 2-methyl-, 4-formyl-2-methoxyphenyl ester; 1,6-Heptadien-3-one, 1-(2,6,6-trimethyl-2-cyclohexen-1-yl)-; Benzoic acid, 2-hydroxy-, hexyl ester; Benzoic acid, phenyl ester; Cyclohexanepropanol, 2,2,6-trimethyl-α-propyl-, (1R,6S)-; Cyclohexanepropanol, 2,2,6-trimethyl-α-propyl-; Benzoic acid, 2-hydroxy-, 3-methyl-2-buten-1-yl ester; 2H-1,5-Benzodioxepin-3(4H)-one, 7-(1-methylethyl)-; Butanal, 4-(octahydro-4,7-methano-5H-inden-5-ylidene)-; Cyclopenta[g]-2-benzopyran, 1,3,4,6,7,8-hexahydro-4,6,6,7,8,8-hexamethyl-; Cyclopentanone, 2-[2-(4-methyl-3-cyclohexen-1-yl)propyl]-; 2(3H)-Naphthalenone, 4,4a,5,6,7,8-hexahydro-4,4a-dimethyl-6-(1-methylethenyl)-, (4R,4aS,6R)-; 2-Propenoic acid, 3-phenyl-, pentyl ester; 4H-Pyran-4-one, 3-hydroxy-2-methyl-; 1-Propanol, 2-methyl-3-[(1,7,7-trimethylbicyclo[2.2.1]hept-2-yl)oxyl]-; 1-Naphthalenol, 1,2,3,4,4a,5,8,8a-octahydro-2,2,6,8-tetramethyl-; 2-Butenoic acid, 2-methyl-, (2E)-3,7-dimethyl-2,6-octadien-1-yl ester, (2E)-; 1,3-Dioxane, 2-(2,4-dimethyl-3-cyclohexen-1-yl)-5-methyl-5-(1-methylpropyl)-; Nonadecane; 4-Penten-2-ol, 3-methyl-5-(2,2,3-trimethyl-3-cyclopenten-1-yl)-; Propanoic acid, 2-methyl-, 2-methyl-4-oxo-4H-pyran-3-yl ester; 2-Buten-1-ol, 2-ethyl-4-(2,2,3-trimethyl-3-cyclopenten-1-yl)-; 1,6-Methanonaphthalen-1(2H)-ol, octahydro-4,8a,9,9-tetramethyl-, (1R,4S,4aS,6R,8aS)-; 2H-1, 5-Benzodioxepin-3(4H)-one, 7-(1,1-dimethylethyl)-; Benzoic acid, phenylmethyl ester; 8-Cyclohexadecen-1-one; Benzoic acid, 2-hydroxy-, (3Z)-3-hexen-1-yl ester; 4H-Pyran-4-one, 2-ethyl-3-hydroxy-; Cyclopentadecanone, 3-methyl-; Benzoic acid, 2-hydroxy-, phenylmethyl ester; 6,8-Nonadien-3-one, 2,4,4,7-tetramethyl-, oxime; Benzoic acid, 2-hydroxy-, cyclohexyl ester; Benzene, [2-(dimethoxymethyl)-1-hepten-1-yl]-; 3-Cyclopentene-1-butanol, β,2,2,3-tetramethyl-δ-methylene-; 4-Penten-1-one, 1-spiro[4.5]dec-7-en-7-yl-; Acetic acid, 2-(1-oxopropoxy)-, 1-(3,3-dimethylcyclohexyl) ethyl ester; 2-Penten-1-ol, 5-[(1R,3R,6S)-2,3-dimethyltricyclo[2.2.1.02,6]hept-3-yl]-2-methyl-, (2Z)-; 4-Penten-2-ol, 3,3-dimethyl-5-(2,2,3-trimethyl-3-cyclopenten-1-yl)-; 5,8-Methano-2H-1-benzopyran-2-one, 6-ethylideneoctahydro-; 4-Cyclopentadecen-1-one, (4Z)-; Ethanone, 1-[(3R,3aR,7R,8aS)-2,3,4,7,8,8a-hexahydro-3,6,8,8-tetramethyl-1H-3a,7-methanoazulen-5-yl]-; 1,3-Dioxolane, 2,4-dimethyl-2-(5,6,7,8-tetrahydro-5,5,8,8-tetramethyl-2-naphthalenyl)-; Oxacyclohexadecan-2-one; 1-Propanol, 2-[1-(3,3-dimethylcyclohexyl)ethoxy]-2-methyl-, 1-propanoate; 5-Cyclopentadecen-1-one, 3-methyl-; 2-Penten-1-ol, 2-methyl-5-[(1S,2R,4R)-2-methyl-3-methylenebicyclo[2.2.1]hept-2-yl]-, (2Z)-; 2H-1,5-Benzodioxepin-3(4H)-one, 7-(3-methylbutyl)-; Ethanone, 1-(2,6,10-trimethyl-2,5,9-cyclododecatrien-1-yl)-; 1H-3a,6-Methanoazulene-3--methanol, octahydro-7,7-dimethyl-8-methylene-, (3S,3aR,6R,8aS)-;Benzeneacetonitrile, α-cyclohexylidene-; Benzoic acid, 2-[(2-methylpentylidene)amino]-, methyl ester; Benzoic acid, 2-phenylethyl ester; 5-Cyclohexadecen-1-one; Cyclohexanol, 4-(1,7,7-trimethylbicyclo[2.2.1]hept-2-yl)-; 3-Cyclohexene-1-carboxaldehyde, 4-(4-hydroxy-4-methylpentyl)-; Ethanone, 1-(5,6,7,8-tetrahydro-3,5,5,6,8,8-hexamethyl-2-naphthalenyl)-; Ethanone, 1-(5,6,7,8-tetrahydro-3,5,5,6,8,8-hexamethyl-2-; 2-Cyclopentadecen-1-one, 3-methyl-;

Oxacycloheptadecan-2-one; Benzeneacetic acid, 4-methylphenyl ester; Benzeneacetic acid, 2-phenylethyl ester; Cyclododecaneethanol, β-methyl-; 2-Propenoic acid, 3-phenyl-, phenylmethyl ester; Benzoic acid, 2,4-dihydroxy-3,6-dimethyl-, methyl ester; Naphtho[2,1-b]furan-6(7H)-one, 8,9-dihydro-1,5,8-trimethyl-, (8R)-; Benzeneacetic acid, (4-methoxyphenyl)methyl ester; Benzene, 2-methoxy-1-(phenylmethoxy)-4-(1-propen-1-yl)-; Benzeneacetic acid, (2E)-3,7-dimethyl-2,6-octadien-1-yl ester; Oxacyclohexadec-12-en-2-one, (12E)-; Benzoic acid, 2-hydroxy-, 2-phenylethyl ester; 2-Propenoic acid, 3-phenyl-, 1-ethenyl-1,5-dimethyl-4-hexen-1-yl ester; Oxacycloheptadec-10-en-2-one; Oxacycloheptadec-8-en-2-one, (8Z)-; 1,7-Dioxacycloheptadecan-8-one; 7-Octen-2-ol, 8-(1H-indol-1-yl)-2,6-dimethyl-; 1,4-Dioxacyclohexadecane-5,16-dione; 1,4-Dioxacycloheptadecane-5,17-dione; Phenol, 4-[3-(benzoyloxy)-1-propen-1-yl]-2-methoxy-; Benzoic acid, 2-[(1-hydroxy-3-phenylbutyl)amino]-, methyl ester; and combinations thereof.

5. The composition of claim 1, wherein the volatile fragrance material is selected from the group consisting of: Formic acid, methyl ester; Methane, 1,1'-thiobis-; Acetic acid ethyl ester; Propanoic acid, ethyl ester; Acetic acid, 2-methylpropyl ester; Butanoic acid, ethyl ester; 1-Butanol; Butanoic acid, 2-methyl-, ethyl ester; 1-Butanol, 3-methyl-, 1-acetate; Butanoic acid, 2-methyl-, 1-methylethyl ester; 2-Heptanone; 2-Hexenal, (2E)-; 1-Butanol, 3-methyl-; 2-Buten-1-ol, 3-methyl-, 1-acetate; 1,3-Dioxolane-2-methanamine, N-methyl-; Bicyclo[3.1.1]hept-2-ene, 2,6,6-trimethyl-, (1R,5R)-; Bicyclo[2.2.1]heptane, 2,2-dimethyl-3-methylene-; 2-Butanethiol, 4-methoxy-2-methyl-; Pentanoic acid, 2-methyl-, ethyl ester; Bicyclo[3.1.0]hexane, 4-methylene-1-(1-methylethyl)-; Bicyclo[3.1.1]heptane, 6,6-dimethyl-2-methylene-; 1-Butanol, 3-methyl-, 1-propanoate; 1,6-Octadiene, 7-methyl-3-methylene-; Octanal; 2H-Pyran, 2-ethenyltetrahydro-2,6,6-trimethyl-; 2-Octanone; Hexanoic acid, ethyl ester; 2-Oxabicyclo[2.2.2]octane, 1,3,3-trimethyl-; Benzene, 1-methyl-4-(1-methylethyl)-; Benzene, 1-methoxy-4-methyl-; 1,3,6-Octatriene, 3,7-dimethyl-; Cyclohexene, 1-methyl-4-(1-methylethenyl)-; Cyclohexene, 1-methyl-4-(1-methylethenyl)-, (4R)-; 3-Octanone; Undecanal, 2-methyl-; Acetic acid, hexyl ester; 5-Hepten-2-one, 6-methyl-; 2-Hepten-4-one, 5-methyl-; 3-Hexen-1-ol, 1-acetate, (3Z)-; 3-Hexen-1-ol, 1-acetate; Propanoic acid, 2-hydroxy-, ethyl ester; Butanoic acid, 2-methylbutyl ester; Butanoic acid, 3-methylbutyl ester; 1,4-Cyclohexadiene, 1-methyl-4-(1-methylethyl)-; Thiazole, 2-(2-methylpropyl)-; 3-Hexen-1-ol, (3Z)-; Benzaldehyde; Butanoic acid, 3-oxo-, ethyl ester; 2-Hexen-1-ol, (2E)-; 2-Hexen-1-ol, (2Z)-; Cyclohexane, 3-ethoxy-1,1,5-trimethyl-, cis-(9CI); 2-Pentanone, 4-mercapto-4-methyl-; 2,4,6-Octatriene, 2,6-dimethyl-, (4E,6E)-; Oxirane, 2,2-dimethyl-3-(3-methyl-2,4-pentadien-1-yl)-; 4,7-Octadienoic acid, methyl ester, (4E)-; Carbonic acid, (3Z)-3-hexen-1-yl methyl ester; Hexanoic acid, 2-propen-1-yl ester; 5-Heptenal, 2,6-dimethyl-; Heptanoic acid, ethyl ester; 3-Cyclohexene-1-carboxaldehyde, 2,4-dimethyl-; Benzene, (2,2-dimethoxyethyl)-; 2H-Pyran, tetrahydro-4-methyl-2-(2-methyl-1-propen-1-yl)-; 3-Nonanone; Benzonitrile; 3-Octanol; 1-Hexanol, 3,5,5-trimethyl-, 1-acetate; 4-Heptanol, 2,6-dimethyl-, 4-acetate; Hexanoic acid, 2-methylpropyl ester; Propanoic acid, 2-methyl-, hexyl ester; Cyclohexanecarboxylic acid, 1,4-dimethyl-, methyl ester, trans-; Benzeneacetaldehyde; Butanoic acid, 3-hydroxy-, ethyl ester; Propanedioic acid, 1,3-diethyl ester; Benzoic acid, methyl ester; 1,3,5-Undecatriene; 4-Decenal, (4E)-; 1,3-Dioxane, 2-butyl-4,4,6-trimethyl-; 2-Heptanol, 2,6-dimethyl-; Ethanone, 1-phenyl-; Benzeneacetaldehyde, α-methyl-; Propanoic acid, 2-methyl-, 1,3-dimethyl-3-buten-1-yl ester; 2,6-Nonadienal, (2E,6Z)-; Pyrazine, 2-methoxy-3-(2-methylpropyl)-; Formic acid, phenylmethyl ester; Benzene, 1-methoxy-4-propyl-; Cyclohexanone, 5-methyl-2-(1-methylethyl)-, (2R,5R)-rel-; Cyclohexanone, 5-methyl-2-(1-methylethyl)-, (2R,5S)-rel-; 2-Nonenal; Cyclohexanone, 2-ethyl-4,4-dimethyl-; Benzene, 1,4-dimethoxy-; Benzene, 1-(ethoxymethyl)-2-methoxy-; Bicyclo[2.2.1]heptan-2-one, 1,7,7-trimethyl-; 2-Hexene, 6,6-dimethoxy-2,5,5-trimethyl-; Decanal; Benzenepropanal, β-methyl-; Benzenemethanol, α-methyl-, 1-acetate; Acetic acid, nonyl ester; Ethanone, 1-(4-methylphenyl)-; 2H-Pyran, 6-butyl-3,6-dihydro-2,4-dimethyl-; Propanoic acid, 2-methyl-, (3Z)-3-hexen-1-yl ester; Benzoic acid, ethyl ester; 3-Octanol, 3,7-dimethyl-, 3-acetate; 1-Hexanol, 5-methyl-2-(1-methylethyl)-, 1-acetate; Cyclohexanol, 3,3,5-trimethyl-, (1R,5R)-rel-; 2-Hexenal, 5-methyl-2-(1-methylethyl)-; 7-Octen-2-ol, 2,6-dimethyl-; Acetic acid, phenylmethyl ester; Cyclohexanone, 2-(1-methylpropyl)-; 3-Octen-1-ol, (3Z)-; Heptanoic acid, 2-propen-1-yl ester; Benzenemethanol; Butanoic acid, 2-methyl-, hexyl ester; 2(3H)-Furanone, 5-ethyldihydro-; Cyclohexaneethanol, 1-acetate; 2-Nonenoic acid, methyl ester; Butanoic acid, (3Z)-3-hexen-1-yl ester; 2-Octynoic acid, methyl ester; 1,3-Oxathiane, 2-methyl-4-propyl-, (2R,4S)-rel-; Heptanal, 6-methoxy-2,6-dimethyl-; Bicyclo[2.2.1]heptan-2-ol, 1,3,3-trimethyl-, 2-acetate; 1,6-Octadien-3-ol, 3,7-dimethyl-, 3-acetate; 2-Octanol, 2,6-dimethyl-; 1-Octanol; 3-Cyclohexene-1-methanethiol, α,α,4-trimethyl-; Cyclohexanemethanol, α,α,4-trimethyl-, 1-acetate; Cyclohexanol, 2-(1,1-dimethylethyl)-, 1-acetate; Cyclohexanol, 4-(1,1-dimethylethyl)-, 1-acetate; Pyrazine, 2-methoxy-3-(1-methylpropyl)-; Cyclohexanol, 5-methyl-2-(1-methylethenyl)-, (1R,2S,5R)-; 2-Undecanone; Benzenepropanol, α,α-dimethyl-; Bicyclo[2.2.1]heptan-2-ol, 1,7,7-trimethyl-, 2-acetate, (1R,2R,4R)-rel-; 1,6-Octadien-3-ol, 3,7-dimethyl-; Benzeneacetic acid, ethyl ester; Benzeneethanol, α,α-dimethyl-; Cyclopropanecarboxylic acid, (3Z)-3-hexen-1-yl ester; 3-Cyclohexene-1-methanol, 3,5-dimethyl-, 1-acetate; Undecanal; Ethanone, 1-(3-cycloocten-1-yl)-; Cyclohexanone, 4-(1,1-dimethylethyl)-; 6-Nonen-1-ol, (6Z)-; Benzene, (2-butoxyethyl)-; Bicyclo[3.1.1]hept-3-en-2-one, 4,6,6-trimethyl-; Cyclohexanecarboxylic acid, 2,2,6-trimethyl-, ethyl ester, (1R,6S)-rel-; Benzeneethanol; 2,6-Octadienal, 3,7-dimethyl-, (2Z)-; 2,6-Octadienal, 3,7-dimethyl-; Cyclohexanol, 5-methyl-2-(1-methylethyl)-, 1-acetate, (1R,2S,5R)-rel-; Benzoic acid, 2-hydroxy-, methyl ester; Benzene, 1-methoxy-4-(1E)-1-propen-1-yl-; 2,6-Octadiene, 1,1-dimethoxy-3,7-dimethyl-; Cyclohexanemethanol, a,3,3-trimethyl-, 1-formate; 2-Decenal, (2E)-; 3-Cyclopentene-1-acetonitrile, 2,2,3-trimethyl-; 2-Cyclohexen-1-one, 2-methyl-5-(1-methylethenyl)-, (5R)-; Cyclohexanone, 4-(1,1-dimethylpropyl)-; 6,10-Dioxaspiro[4.5]decane, 8,8-dimethyl-7-(1-methylethyl)-; 2-Cyclohexen-1-one, 3-methyl-5-propyl-; Benzonitrile, 4-(1-methylethyl)-; 2,6-Nonadienenitrile; Butanoic acid, 2-methyl-, (3Z)-3-hexen-1-yl ester; Benzene, 1-(cyclopropylmethyl)-4-methoxy-; 2-Nonynoic acid, methyl ester; Acetic acid, 2-phenylethyl ester; Cyclohexanol, 2-(1,1-dimethylethyl)-; 2,6-Nonadien-1-ol; Propanoic acid, 2-methyl-, phenylmethyl ester; Bicyclo[2.2.1]heptan-2-ol, 1,2,3,3-tetramethyl-, (1R,2R,4S)-rel-; Benzaldehyde, 4-(1-methylethyl)-; 2,5-Octadien-4-one, 5,6,7-trimethyl-, (2E)-; 3-Cyclohexen-1-ol, 4-methyl-1-(1-methylethyl)-; 3-Cyclohexene-1-methanol, 2,4,6-trimethyl-; Pentanoic acid, (3Z)-3-hexen-1-yl ester; Bicyclo[2.2.1]heptan-2-ol, 1,7,7-trimethyl-, 2-propanoate, (1R,2R,4R)-rel-; Benzene, 1-methyl-4-(1-methylethyl)-2-

(1-propen-1-yl)-; 3-Cyclohexene-1-propanal, β,4-dimethyl-; 1-Hexanol, 5-methyl-2-(1-methylethyl)-, (2R)-; 3-Heptanone, 5-methyl-, oxime; 2(3H)-Furanone, 5-butyldihydro-; 1-Nonanol; Acetic acid, 2-(3-methylbutoxy)-, 2-propen-1-yl ester; Bicyclo[2.2.1]heptan-2-ol, 1,7,7-trimethyl-, (1S,2R,4S)-; Bicyclo[2.2.1]heptan-2-ol, 1,7,7-trimethyl-, (1R,2R,4R)-rel-; Cyclohexanol, 2-(1,1-dimethylpropyl)-, 1-acetate; 3-Cyclohexene-1-methanol, α,α,4-trimethyl-, 1-acetate; Cyclohexanemethanol, α,α,4-trimethyl-; 10-Undecenal; 2,4-Cyclohexadiene-1-carboxylic acid, 2,6,6-trimethyl-, ethyl ester; 1-Octanol, 3,7-dimethyl-; Furan, tetrahydro-2,4-dimethyl-4-phenyl-; Benzene, [2-(3-methylbutoxy)ethyl]-; Butanoic acid, phenylmethyl ester; Benzoic acid, 2-hydroxy-, ethyl ester; Cyclohexanol, 4-(1,1-dimethylethyl)-; 1,6-Octadien-3-ol, 3,7-dimethyl-, 3-formate; Dodec anal; 3,6-Nonadien-1-ol, (3Z,6Z)-; 3,6-Nonadien-1-ol; Decanenitrile; Cyclohexanol, 5-methyl-2-(1-methylethyl)-, (1R,2S,5R)-; Propanoic acid, 2-methyl-, 4-methylphenyl ester; Propanoic acid, 2-methyl-, (1R,2S,4R)-1,7,7-trimethylbicyclo[2.2.1]hept-2-yl ester, rel-; Acetaldehyde, 2-(4-methylphenoxy)-; 2-Butenoic acid, 2-methyl-, (3Z)-3-hexen-1-yl ester, (2E)-; Bicyclo[3.1.1]hept-2-ene-2-propanal, 6,6-dimethyl-; 2-Nonanol, 6,8-dimethyl-; Cyclohexanol, 1-methyl-3-(2-methylpropyl)-; 1H-Indole; 2-Undecenal; 2H-Pyran-2-one, 4,6-dimethyl-; 3-Cyclohexene-1-methanol, α,α,4-trimethyl-; 3-Hepten-2-one, 3,4,5,6,6-pentamethyl-, (3Z)-; 2(3H)-Furanone, 5-butyldihydro-4-methyl-; 7-Octen-2-ol, 2,6-dimethyl-, 2-acetate; 2-Propenal, 3-phenyl-; 1,6-Octadien-3-ol, 3,7-dimethyl-, 3-propanoate; 1,6-Nonadien-3-ol, 3,7-dimethyl-, 3-acetate; Cyclopentanone, 2,2,5-trimethyl-5-pentyl-; 2,6-Octadien-1-ol, 3,7-dimethyl-, 1-acetate, (2Z)-; 2,6-Octadien-1-ol, 3,7-dimethyl-, 1-acetate, (2E)-; Undecane, 1,1-dimethoxy-2-methyl-; Benzenemethanol, α-methylene-, 1-acetate; Benzaldehyde, 4-methoxy-; Cyclohexanol, 5-methyl-2-(1-methylethenyl)-, 1-acetate, (1R,2S,5R)-; 6-Octenenitrile, 3,7-dimethyl-; 6-Octen-2-ol, 2,6-dimethyl-; Benzene, 1,1'-oxybis-; Benzoic acid, butyl ester; 5,8-Methano-2H-1-benzopyran, 6-ethylideneoctahydro-; Cyclohexanepropanol, α,α-dimethyl-; Benzenepropanal, β-methyl-3-(1-methylethyl)-; Benzenemethanol, 4-methoxy-, 1-acetate; Phenol, 2-ethoxy-4-methyl-; Benzene, [2-(1-propoxyethoxy)ethyl]-; 7-Octen-1-ol, 3,7-dimethyl-; Bicyclo[4.3.1]decane, 3-methoxy-7,7-dimethyl-10-methylene-; Propanoic acid, 2-(1,1-dimethylpropoxy)-, propyl ester, (2S)-; Benzoic acid, 2-(methylamino)-, methyl ester; 6-Octen-1-ol, 3,7-dimethyl-, (3S)-; 7-Octen-2-ol, 2-methyl-6-methylene-; 4,6-Octadien-3-ol, 3,7-dimethyl-; 5-Oxatricyclo[8.2.0.04,6]dodecane, 4,9,12,12-tetramethyl-; 2-Cyclohexene-1-carboxylic acid, 2-ethyl-6,6-dimethyl-, ethyl ester; 3-Buten-2-one, 4-(2,6,6-trimethyl-1-cyclohexen-1-yl)-, (3E)-; 4,7-Methano-1H-inden-5-ol, octahydro-, 5-acetate; Benzoic acid, 2-amino-, methyl ester; Spiro[1,3-dioxolane-2,8'(5'H)-[2H-2,4a]methanonaphthalene], hexahydro-1',1',5',5'-tetramethyl-, (2'S,4'aS,8'aS)- (9CI); Spiro[1,3-dioxolane-2,8'(5'H)-[2H-2,4a]methanonaphthalene], hexahydro-1',1',5',5'-tetramethyl-; 3-Buten-2-one, 4-(2,6,6-trimethyl-2-cyclohexen-1-yl)-, (3E)-; Benzeneethanol, α,α-dimethyl-, 1-acetate; 4,7-Methano-1H-inden-5-ol, 3a,4,5,6,7,7a-hexahydro-, 5-acetate; 6-Octen-1-ol, 3,7-dimethyl-, 1-acetate; 2H-Pyran, tetrahydro-2-methyl-4-methylene-6-phenyl-; Bicyclo[3.3.1]nonane, 2-ethoxy-2,6,6-trimethyl-9-methylene-; 2,6-Octadien-1-ol, 3,7-dimethyl-, (2E)-; Bicyclo[7.2.0]undec-4-ene, 4,11,11-trimethyl-8-methylene-, (1R,4E,9S)-; 1H-3a,7-Methanoazulene, octahydro-6-methoxy-3,6,8,8-tetramethyl-, (3R,3aS,6S,7R,8aS)-; Bicyclo[7.2.0]undec-4-ene, 4,11,11-trimethyl-8-methylene-, (1R,4E,9S)-; 1H-Inden-1-one, 2,3-dihydro-2,3,3-trimethyl-; 2-Propanol, 1,1'-oxybis-; 2-Octanol, 7-methoxy-3,7-dimethyl-; 4,9-Decadienal, 4,8-dimethyl-; Benzoic Acid; 3-Hexenoic acid, (3Z)-3-hexen-1-yl ester, (3Z)-; Bicyclo[2.2.1]hept-5-ene-2-carboxylic acid, 3-(1-methylethyl)-, ethyl ester, (1R,2S,3S,4S)-rel-; 2-Propen-1-ol, 3-phenyl-; Propanoic acid, 2-methyl-, 1-ethenyl-1,5-dimethyl-4-hexen-1-yl ester; Ethanol, 2-phenoxy-, 1-propanoate; 2-Propenoic acid, 3-phenyl-, methyl ester; Benzenepropanal, 2-ethyl-α,α-dimethyl-; Propanoic acid, decyl ester; Benzene, 1,2-dimethoxy-4-(1-propen-1-yl)-; 3-Decen-5-ol, 4-methyl-; Phenol, 2-methoxy-4-(2-propen-1-yl)-; 1-Propanone, 1-[2-methyl-5-(1-methylethyl)-2-cyclohexen-1-yl]-; 1,3-Benzodioxole-5-carboxaldehyde; 2-Dodecenal; 2-Dodecenal, (2E)-; Benzenepropanal, 4-methoxy-α-methyl-; 1,4-Cyclohexanedicarboxylic acid, 1,4-dimethyl ester; 2-Buten-1-one, 1-(2,6,6-trimethyl-3-cyclohexen-1-yl)-; 2-Butanone, 4-(2,6,6-trimethyl-1-cyclohexen-1-yl)-; 2-Propenenitrile, 3-phenyl-, (2E)-; Propanoic acid, 2-methyl-, 2-phenylethyl ester; 2-Cyclopenten-1-one, 3-methyl-2-(2Z)-2-penten-1-yl-; Acetaldehyde, 2-[(3,7-dimethyl-6-octen-1-yl)oxy]-; 1-Cyclohexene-1-ethanol, 4-(1-methylethyl)-, 1-formate; 2,4-Decadienoic acid, ethyl ester, (2E,4Z)-; 2-Propen-1-ol, 3-phenyl-, 1-acetate; Naphtho[2,1-b]furan, dodecahydro-3a,6,6,9a-tetramethyl-, (3aR,5aS,9aS,9bR)-; Benzenepropanal, 4-(1,1-dimethylethyl)-; Naphtho[2,1-b]furan, dodecahydro-3a,6,6,9a-tetramethyl-; 1,4-Methanonaphthalen-5(1H)-one, 4,4a,6,7,8,8a-hexahydro-; Dodecanoic acid, 12-hydroxy-, λ-lactone (6CI,7CI); 1,12-; Cyclohexanepropanoic acid, 2-propen-1-yl ester; 2(3H)-Furanone, 5-hexyldihydro-5-methyl-; 2,6-Nonadienenitrile, 3,7-dimethyl-; 10-Undecenoic acid, ethyl ester; Benzenepropanal, α-methyl-4-(1-methylethyl)-; 1-Oxaspiro[4.5]decan-2-one, 8-methyl-; 2(3H)-Furanone, dihydro-5-pentyl-; 2(3H)-Furanone, 5-hexyldihydro-; 2-Buten-1-one, 1-(2,6,6-trimethyl-2-cyclohexen-1-yl)-, (2E)-; 2-Buten-1-one, 1-(2,4,4-trimethyl-2-cyclohexen-1-yl)-, (2E)-; 2H-Pyran-2-one, tetrahydro-6-pentyl-; Benzenepropanal, 4-ethyl-α,α-dimethyl-; 1,3-Benzodioxole, 5-(diethoxymethyl)-; 4-Penten-1-one, 1-(5,5-dimethyl-1-cyclohexen-1-yl)-; Bicyclo[3.1.1]hept-2-ene-2-ethanol, 6,6-dimethyl-, 2-acetate; 2-Propenoic acid, 3-phenyl-, ethyl ester; 1,3-Dioxane, 2,4,6-trimethyl-4-phenyl-; Cyclododecane, (methoxymethoxy)-; Bicyclo[3.1.1]hept-2-ene-2-propanal, α,α,6,6-tetramethyl-; Benzeneacetonitrile, 4-(1,1-dimethylethyl)-; 2-Buten-1-one, 1-(2,6,6-trimethyl-1-cyclohexen-1-yl)-; 1,4-Methanonaphthalen-6(2H)-one, octahydro-7-methyl-; Bicyclo[3.2.1]octan-8-one, 1,5-dimethyl-, oxime; Benzenepentanol, γ-methyl-; Cyclohexene, 4-(1,5-dimethyl-4-hexen-1-ylidene)-1-methyl-; Phenol, 2-methoxy-4-propyl-; Benzoic acid, 2-hydroxy-, 2-methylpropyl ester; 2H-1-Benzopyran-2-one, octahydro-; Cyclohexanone, 2-(1-mercapto-1-methylethyl)-5-methyl-; 2-Oxiranecarboxylic acid, 3-methyl-3-phenyl-, ethyl ester; 3-Cyclohexene-1-carboxaldehyde, 4-(4-methyl-3-penten-1-yl)-; Propanoic acid, 2-methyl-, 2-phenoxyethyl ester; Indeno[1,2-d]-1,3-dioxin, 4,4a,5,9b-tetrahydro-; 2H-Pyran-4-ol, tetrahydro-4-methyl-2-(2-methylpropyl)-; Cyclohexanebutanal, α,2,6,6-tetramethyl-; 1,6-Nonadien-3-ol, 3,7-dimethyl-; 3-Buten-2-one, 4-(2,2,6-trimethyl-7-oxabicyclo[4.1.0]hept-1-yl)-; Phenol, 2-methoxy-4-(1-propen-1-yl)-; 2(3H)-Furanone, 5-hexyldihydro-4-methyl-; 1-Penten-3-one, 1-(2,6,6-trimethyl-2-cyclohexen-1-yl)-; 2-Buten-1-one, 1-(2,6,6-trimethyl-1,3-cyclohexadien-1-yl)-; 2-Cyclopenten-1-one, 2-hydroxy-3-methyl-; Propanoic acid, 2,2-dimethyl-, 2-phenylethyl ester; Dodecanenitrile; 6-Octen-1-ol, 3,7-dimethyl-, 1-propanoate; Benzenepentanal, β-methyl-; Acetic acid, 2-phenoxy-, 2-propen-1-yl ester; Benzenepropanal, 4-(1,1-dimethylethyl)-α-methyl-; 4,7-Methano-1H-indene-2-carboxaldehyde, octahydro-5-methoxy-; Pentitol, 1,5-anhydro-2,4-dideoxy-2-pentyl-, 3-acetate; Cyclododecane, (ethoxymethoxy)-; 3-Buten-2-one, 4-(2,5,6,6-tetramethyl-2- cyclohexen-1-yl)-; Quinoline, 6-(1-methylpropyl)-; Carbonic acid, 4-cycloocten-1-yl methyl ester; 1H-Indene-5-propanal, 2,3-dihydro-3,3-dimethyl-; Ethanone, 1-(3-methyl-2-benzofuranyl)-; 3-Cyclohexene-1-carboxaldehyde, 1-methyl-3-(4-methyl-3-penten-1-yl)-; 6-Oxabicyclo[3.2.1]octane, 5-methyl-1-(2,2,3-trimethyl-3-cyclopenten-1-yl)-; 2H-Pyran-2-one, tetrahydro-6-(3-penten-1-yl)-; 2,4,7-Decatrienoic acid, ethyl ester; Butanoic acid, 3-methyl-, 2-phenylethyl ester; Spiro[1,4-methanonaphthalene-2(1H),2'-oxirane], 3,4,4a,5,8,8a-hexahydro-3',7-dimethyl-; Ethanol, 2-[[(1R,2R,4R)-1,7,7-trimethylbicyclo [2.2.1]hept-2-yl]oxy]-, rel-; Phenol, 2-methoxy-4-(1-propen-1-yl)-, 1-acetate; 2H-Indeno[4,5-b]furan, decahydro-2,2,6,6,7,8,8-heptamethyl-; Acetic acid, 2-(cyclohexyloxy)-, 2-propen-1-yl ester; Octanal, 7-hydroxy-3,7-dimethyl-; Naphtho[2,1-b]furan, 9b-ethyldodecahydro-3a,7, 7-trimethyl-; 1,6-Heptadien-3-one, 2-cyclohexyl-; 5-Thiazoleethanol, 4-methyl-; 1-Penten-3-one, 1-(2,6,6-trimethyl-2-cyclohexen-1-yl)-; 3-Buten-2-one, 3-methyl-4-(2,6,6-trimethyl-2-cyclohexen-1-yl)-; 1,4-Cyclohexanedicarboxylic acid, 1,4-diethyl ester; 2(3H)-Furanone, 5-heptyldihydro-; 1,3-Benzodioxole-5-propanal, α-methyl-; 4H-Inden-4-one, 1,2,3,5,6,7-hexahydro-1,1,2,3,3-pentamethyl-; Cyclohexanone, 4-(1-ethoxyethenyl)-3,3,5,5-tetramethyl-; Benzenepropanenitrile, α-ethenyl-α-methyl-; 9-Undecenal, 2,6,10-trimethyl-; Pyridine, 2-(3-phenylpropyl)-; Indeno[1,2-d]-1,3-dioxin, 4,4a,5,9b-tetrahydro-2,4-dimethyl-; Propanoic acid, 2-methyl-, 3a,4,5,6,7,7a-hexahydro-4,7-methano-1H-inden-5-yl ester; 1-Naphthalenol, 1,2,3,4, 4a,7,8,8a-octahydro-2,4a,5,8a-tetramethyl-, 1-formate; Benzenepropanol, β,β,3-trimethyl-; 2-Cyclohexen-1-one, 4-(2-buten-1-ylidene)-3,5,5-trimethyl-; 3-Hexen-1-ol, 1-benzoate, (3Z)-; Benzaldehyde, 4-hydroxy-3-methoxy-; 1H-3a,7-Methanoazulen-6-ol, octahydro-3,6,8,8-tetramethyl-, 6-acetate, (3R,3aS,6R,7R,8aS)-; 4,7-Methano-1H-inden-6-ol, 3a,4,5,6,7,7a-hexahydro-8,8-dimethyl-, 6-propanoate; 2-Oxiranecarboxylic acid, 3-phenyl-, ethyl ester; 4H-4a,9-Methanoazuleno[5,6-d]-1,3-dioxole, octahydro-2, 2,5,8,8,9a-hexamethyl-, (4aR,5R,7aS,9R)-; Butanoic acid, 1,1-dimethyl-2-phenylethyl ester; Cyclododeca[c]furan, 1,3, 3a,4,5,6,7,8,9,10,11,13a-dodecahydro-; Benzenebutanenitrile, α,α,γ-trimethyl-; 2-Butanone, 4-(1,3-benzodioxol-5-yl)-; Benzoic acid, 4-hydroxy-3-methoxy-, methyl ester; 3-Cyclopentene-1-butanol, β,2,2,3-tetramethyl-2-Methyl-4-(2,2,3-trimethyl-3-cyclopenten-1-yl)butanol; 2-Butenal, 2-methyl-4-(2,6,6-trimethyl-1-cyclohexen-1-yl)-; 2-Naphthalenol, decahydro-2,5,5-trimethyl-; 1,7-Octanediol, 3,7-dimethyl-; 2H-1-Benzopyran-2-one; 1,3-Dioxolane, 2-[6-methyl-8-(1-methylethyl)bicyclo[2.2.2]oct-5-en-2-yl]-; Propanoic acid, 2,2-dimethyl-, 3a,4,5,6,7,7a-hexahydro-4,7-methano-1H-inden-6-yl ester; Butanoic acid, (2E)-3,7-dimethyl-2,6-octadien-1-yl ester; 2-Butanone, 4-(4-hydroxyphenyl)-; 10-Undecenoic acid, butyl ester; and combinations thereof.

6. The composition of claim 1, wherein the volatile fragrance material is selected from the group consisting of:
  (i) a high volatile fragrance material having a vapor pressure greater than 0.1 Torr at 25° C.;
  (ii) a moderate volatile fragrance material having a vapor pressure in the range of 0.1 Torr at 25° C. to 0.001 Torr at 25° C.; and
  (iii) combinations thereof.

7. The composition of claim 1, further comprising ethanol present in the amount of about 50 wt % to about 80 wt %, relative to the total weight of the composition.

8. The composition of claim 1, further comprising one or more non-odorous fragrance co-modulators selected from the group consisting of:
  (i) Isocetyl alcohol;
  (ii) PPG-3 myristyl ether;
  (iii) Neopentyl glycol diethylhexanoate; and
  (iv) mixtures thereof;
  wherein the one or more non-odorous fragrance co-modulators are present in the amount of about 0.05 wt % to about 10 wt %, relative to the total weight of the composition.

9. The composition of claim 8, wherein the non-odorous fragrance modulators are formed of at least 50 wt % of a non-odorous fragrance modulator, relative to the combined weight of the non-odorous fragrance modulators and the non-odorous fragrance co-modulators.

10. The composition according to claim 8, further comprising one or more non-odorous fragrance co-modulators selected from the group consisting of Isocetyl alcohol, PPG-3 myristyl ether, Neopentyl glycol diethylhexanoate, and a mixture thereof, in the amount of from about 0.5 wt % to about 6 wt %, relative to the total weight of the composition.

11. The composition according claim 1, wherein the composition is in the form of a perfume, an eau de toilette, an eau de parfum, a cologne, a body splash, or a body spray.

12. A method to enhance the fragrance profile of a floral aroma, comprising bringing into contact or mixing at least one non-odorous fragrance modulator with at least one low volatile fragrance material according to a composition as defined in claim 1.

13. The method of claim 12, wherein the floral aroma is selected from the group consisting of a lavender-type note, a rose-type note, a lily of the valley-type note, a muguet-type note, a jasmine-type note, a *magnolia*-type note, a cyclamen-type note, a hyacinth-type note, a lilac-type note, an orange blossom-type note, a cherry blossom-type note, a peony-type note, a lotus-type note, a linden blossom-type note, an osmanthus-type note, a lilac-type note, a heliotrope-type note, a violet-type note, an orris-type note, a tiare-type note, and combinations thereof.

14. A method for producing a consumer product comprising bringing into contact or mixing into the product an organoleptically active quantity of a fragrance composition according to claim 1.

15. A perfuming consumer product or article comprising a fragrance composition according to claim 1, wherein the perfuming consumer product is selected from the group consisting of a fabric care product, an air care product, or a home care product.

16. A method of modifying or enhancing the odour properties of a body surface, comprising contacting or treating the body surface with a composition according to claim 1.

17. A composition comprising:
  (i) from about 50 wt % to about 80 wt % of ethanol, relative to the weight of the compisition;
  (ii) from about 0.1 wt % to about 20 wt %, relative to the weight of the composition, of at least one non-odorous fragrance modulator selected from the group consisting of methyl glucoside polyol, ethyl glucoside polyol, and propyl glucoside polyol; and
  (iii) a fragrance component;
  wherein wt % of the non-odorous fragrance modulator is greater than the wt % of the fragrance component.

* * * * *